United States Patent [19]

Johnson

[11] Patent Number: 4,662,222

[45] Date of Patent: May 5, 1987

[54] APPARATUS AND METHOD FOR ACOUSTIC IMAGING USING INVERSE SCATTERING TECHNIQUES

[76] Inventor: Steven A. Johnson, 1155 East 300 South, #8, Salt Lake City, Utah 84102

[21] Appl. No.: 684,801

[22] Filed: Dec. 21, 1984

[51] Int. Cl.⁴ .......................................... G01N 29/04
[52] U.S. Cl. ...................................... 73/602; 73/607; 128/660
[58] Field of Search ................. 73/602, 607, 626, 596; 128/660

[56] References Cited

U.S. PATENT DOCUMENTS

| 4,222,274 | 9/1980 | Johnson | 73/607 |
| 4,317,369 | 3/1982 | Johnson | 73/607 |
| 4,594,662 | 6/1986 | Devaney | 73/602 |

OTHER PUBLICATIONS

De Figueiredo, Rui J.P., "Approximation-Theoretic Methods for Nonlinear Deconvolution and Inversion", Information Sciences, vol. 31, No. 3, pp. 209–213 (1983).
Johnson, S. A. et al., "Acoustic Inverse Scattering Solutions by Moment Methods and Backpropagation", Conference on Inverse Scattering: Theory and Application, SIAM, Philadelphia (1983).
Johnson, S. A. et al., "Inverse Scattering Solutions by a Sinc Basis, Multiple Source, Moment Method—Part I: Theory", Ultrasonic Imaging, vol. 5, pp. 361–375.
Johnson, S. A. et al., "Inverse Scattering Solutions by a Sinc Basis, Multiple Source, Moment Method—Part II: Numerical Evaluations", Ultrasonic Imaging, vol. 5, pp. 376–392.
Johnson, Steven A. et al., "Ultrasound Tomography by Galerkin or Moment Methods", Lecture Notes in Medical Informatics, vol. 23, pp. 254–275 (1984).
Johnson, S. A. et al., "Fast Iterative Algorithms for Inverse Scattering Solutions of the Helmholtz and Riccati Wave Equations", Acoustical Imaging, vol. 13, pp. 75–87, Ed. M. Kaven, R. K. Mueller, and J. F. Greenleaf, Plenum Press (1984).
Johnson, S. A. et al., "Inverse Scattering Solutions by a Sinc Basis, Multiple Source, Moment Method—Part III: Fast Algorithms", Ultrasonic Imaging, vol. 6, pp. 103–116, Academic Press (1984).
Tarantola, A., "Inversion of Seismic Reflection Data in the Acoustic Approximation", Geophysics, vol. 49, No. 8, pp. 1259–1266 (1984).
Berkhout, A. J. et al., "The Relationship Between Multi-Dimensional Linearized Inversion and Seismic Migration", Abstract of presentation made at 54th Annual Meeting and Exposition of the Society of Exploration Geophysicists held at Atlanta, Ga. on Dec. 2–6, 1984.
Carrion, Philip M. et al., "A Method for Computation (List continued on next page.)

Primary Examiner—Anthony V. Ciarlante
Attorney, Agent, or Firm—Workman, Nydegger & Jensen

[57] ABSTRACT

An apparatus and method for reconstructing an acoustic image of an object using a central processing unit programmed to process data derived from acoustic energy that has been transmitted at multiple frequencies and scattered by the object. Electronic signals are propagated at multiple frequencies and transduced into acoustic energy waves which are propagated toward an object. Transducer receivers detect the acoustic energy waves after they have been scattered by the object and the detected acoustic energy waves are then electronically processed and input into a high-speed digital computer which may comprise a central processing unit and/or a central processing unit in combination with an array processor. Data is also prepared and input to the computer representing the incident field and the computer then reconstructs a high-quality image of the scanned object so as to produce an image having high spacial resolution and including actual internal viscous and elastic properties of the object through the use of new inverse scattering techniques used in the data processing steps.

38 Claims, 35 Drawing Figures

FIG. 4A

OTHER PUBLICATIONS of Velocity Profiles by Inversion of Large-Offset Records, Geophysics, vol. 49, No. 8, pp. 1249-1258 (1984).

Cheng, Guan and Shimon Coen, "The Relationship between Born Inversion, Rytov Inversion, and Migration for Both CMP Stacked and Slant Stacked Data, Abstract of presentation made at 54th Annual Meeting & Exposition of the Society of Exploration Geophysicists, Atlanta, 12/2-6/84.

Foster, Douglas J. et al., "Linear Inversion Applied to Real Seismic Data", Abstract of presentation made at the 54th Annual Meeting & Exposition of the Society of Exploration Geophysicists, Atlanta, 12/2-6/84.

Gauthier, O. et al., "Nonlinear Inversion of Seismic Reflection Data", Abstract of presentation made at the 54th Annual Meeting & Exposition of the Society of Exploration Geophysicists held at Atlanta, Dec. 2-6, 1984.

Goutsias et al., "A 2-D Stochastic Earth Model for Seismic Inversion", Abstract of presentation made at the 54th Annual Meeting and Exposition of the Society of Exploration Geophysicists held at Atlanta, Ga., Dec. 2-6, 1984.

Greenleaf, James F., "Computer Tomography from Ultrasound Scattered by Biological Tissues, American Mathematical Society—Symposium of Inverse Problems, (1983).

Hanson, Douglas W., "Multiparameter Seismic Inversion of Noisy Data", Abstract of presentation made at the 54th Annual Meeting and Exposition of the Society of Exploration Geophysicists held at Atlanta, Ga., Dec. 2-6, 1984.

Harkrider, David G., "Synthetics and Theoretical Seismology", Reviews of Geophysics and Space Physics, vol. 21, No. 6, pp. 1299-1308 (1983).

Kaman, E. J., "Detailed Inversion of Reservoir Data by Constrained Parameter Estimation and Resolution Analysis," Abstract of presentation made at 54th Annual Meeting and Exposition of the Society of Exploration Georphysicists at Atlanta, Ga., Dec. 2-6, 1984.

Lailly, P., "Migration Methods: Practical but Efficient Solutions to the Seismic Inverse Problem," Inverse Problems of Acoustic and Elastic Waves, pp. 182-214.

La Bras, L. et al., "Presentation of a Born Inversion for Multioffset Reflection Data: Tests on Synthetic Seismograms," Abstract of presentation made at 54th Annual Meeting and Exposition of the Society of Exploration Geophysicists at Atlanta, Ga., Dec. 2-6, 1984.

Lines, Larry R. et al., "Inversion with a Grain of Salt," Abstract of presentation made at 54th Annual Meeting and Exposition of the Society of Exploration Geophysicists at Atlanta, Ga., Dec. 2-6, 1984.

Macdonald, Calum et al., "Nonlinear Seismic Inversion", Abstract of presentation made at 54th Annual Meeting and Exposition of the Society of exploration Geophysicists at Atlanta, Ga., Dec. 2-6, 1984.

McClary, W. Keith, "Fast Seismic Inversion", Geophysics, vol. 48, No. 10, pp. 1371-1372 (1983).

Morley, Lawrence C., "Invertibility of Elastic Layered Earth Parameters from Precritical P-Wave Reflection Amplitudes", Abstract of presentation at 54th Annual Meeting and Exposition of the Society of Exploration Georphysicists at Atlanta, Ga., Dec. 2-6, 1984.

Nercessian, A., "Linearized Inversion of Multioffset Seismic Reflection Data," Abstract of presentation at 54th Annual Meeting and Exposition of the Society of Exploration Geophysicists at Atlanta, Ga., Dec. 2-6, 1984.

Sigalov, Ya. B. et al., "On the Solution of the Two-Dimensional Inverse Dynamic Problem of Seismometry by the Finite-Difference Method, Part 1." Geophysical Journal, vol. 5, No. 4, pp. 508-521 (1984).

Tarantola, A. et al., "Generalized Nonlinear Inverse Problems Solved Using the Lease Squares Criterion," Review of Geophysics and Space Physics, vol. 20, No. 2, pp. 219-232 (1982).

Tarantola, A. et al., "Inverse Problems: Quest of Information", J. Geophysics, vol. 50, No. 3, pp. 159-170 (1982).

Tarantola, A., "Linearized Inversion of Seismic Reflection Data," Geophysical Prospecting, vol. 30, pp. 98-1015 (1984).

VerWest, B. J. et al., "Prestack Inversion of Plane-Layered Viscoacoustic Earth Parameters," Abstract of presentation at 54th Annual Meeting and Exposition of the Society of the Exploration Geophysicist at Atlanta, Ga., Dec. 2-6, 1984.

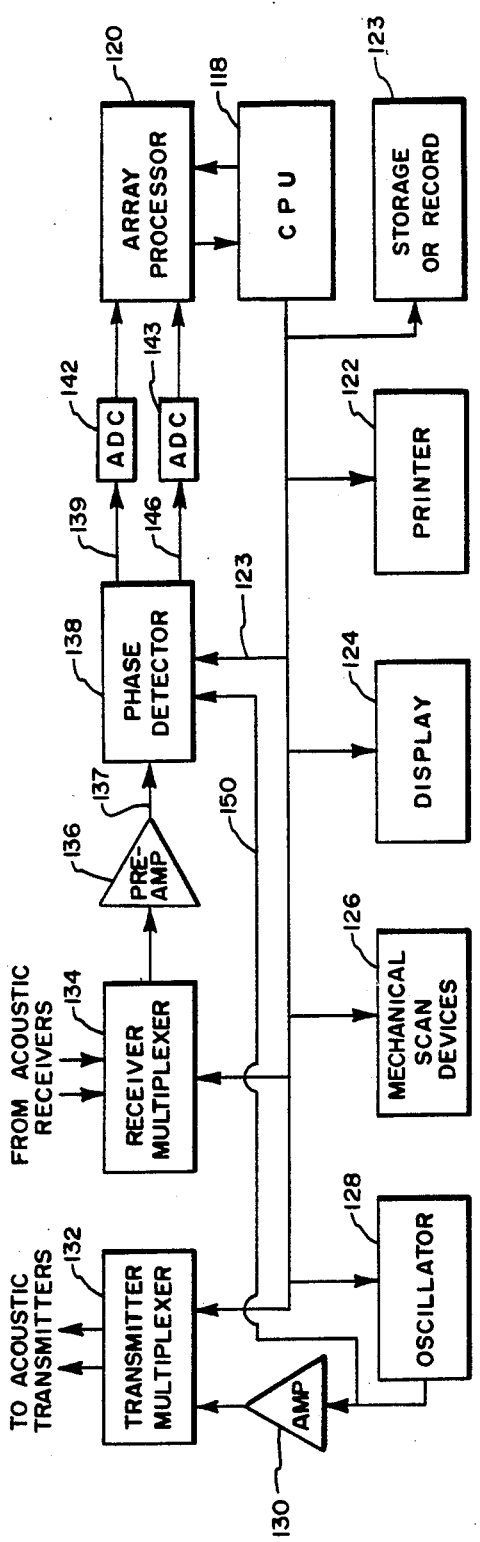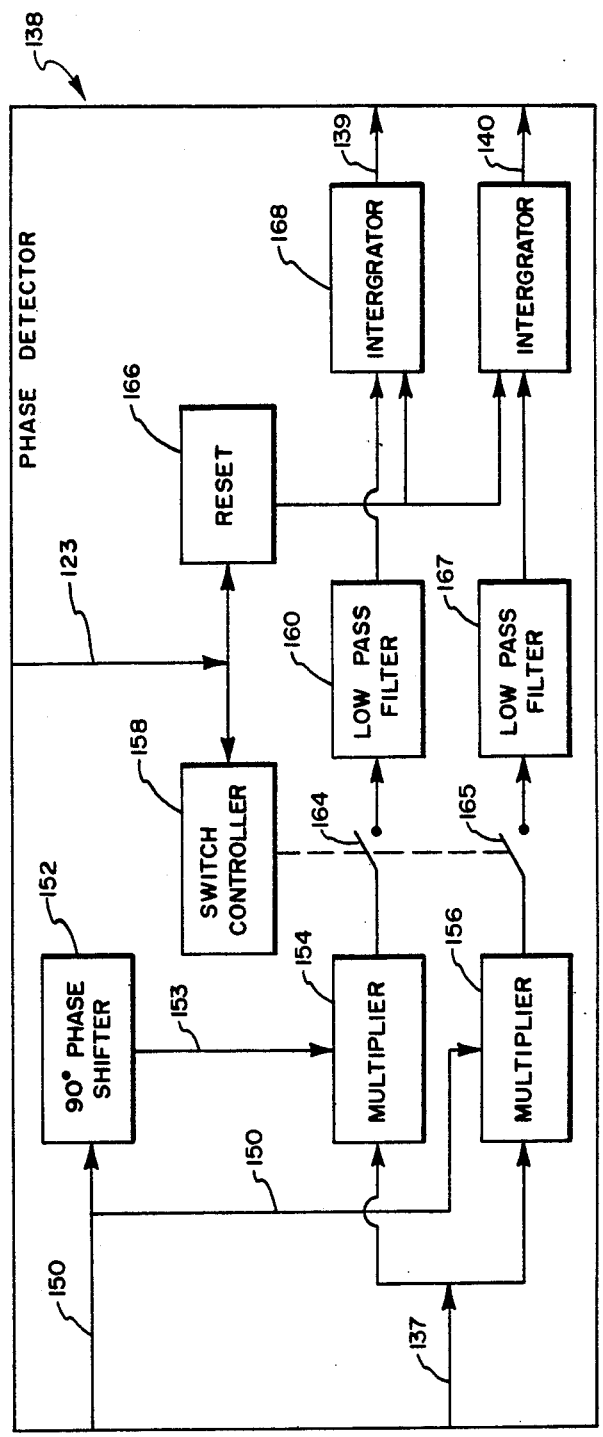

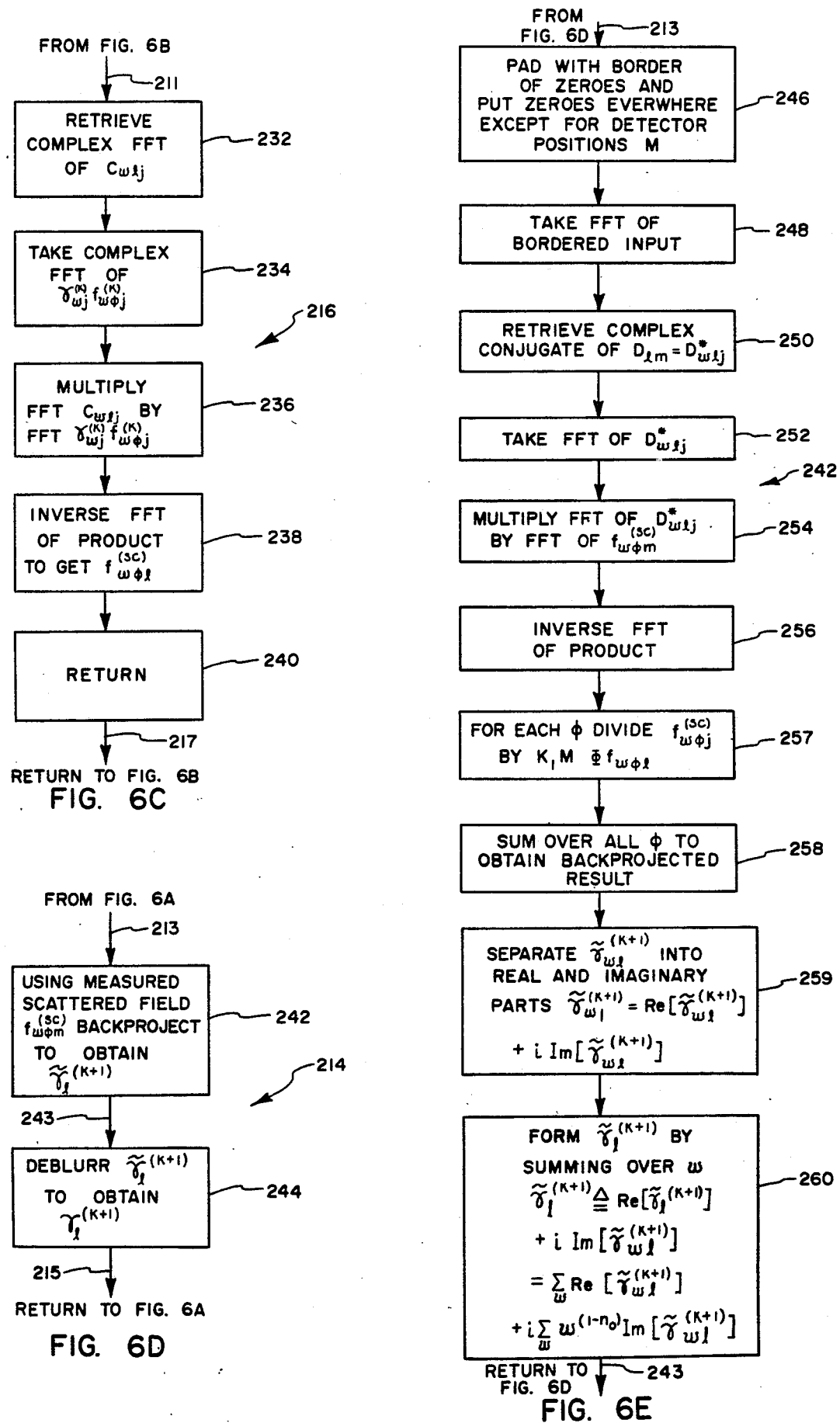

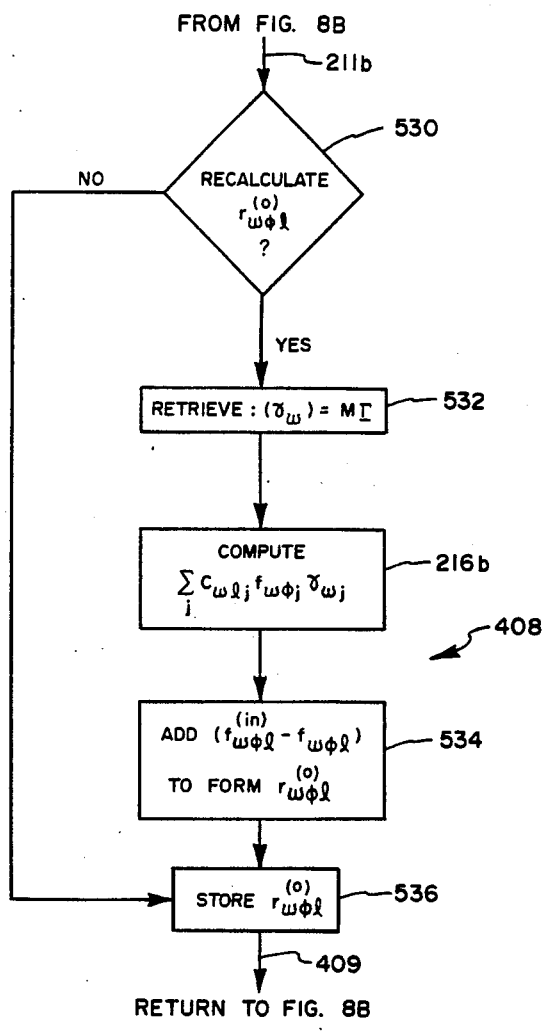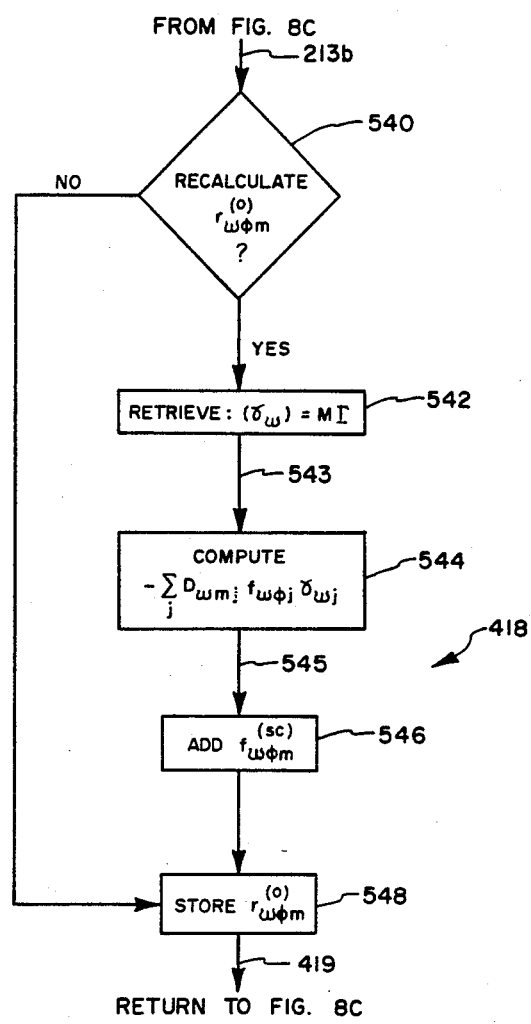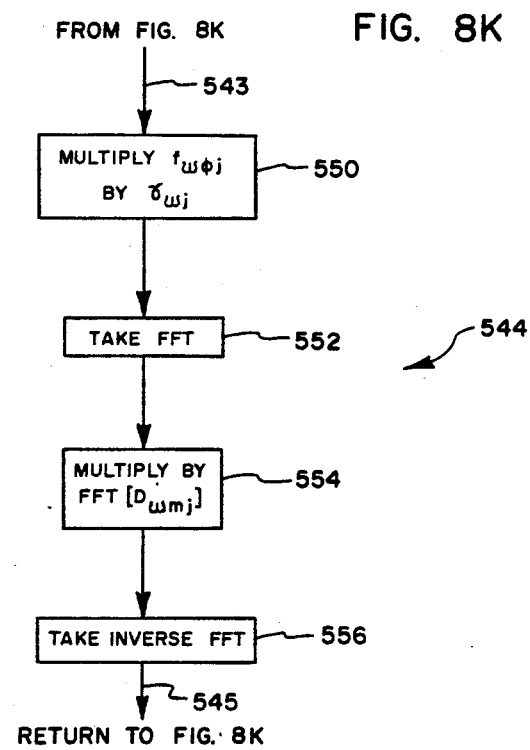

APPARATUS AND METHOD FOR ACOUSTIC IMAGING USING INVERSE SCATTERING TECHNIQUES

BACKGROUND

1. Field of the Invention

The present invention relates to an apparatus and method for acoustic imaging, which is defined herein to mean electronic reconstruction and display of the size, shape, and internal elastic and viscous properties (e.g., density, acoustic speed, and acoustic energy absorption) of an object or material. More particularly, the present invention relates to an apparatus and method for acoustic imaging using inverse scattering techniques.

2. The Prior Art

It has long been known that acoustic waves in the frequency range of a fraction of a cycle per second up to hundreds of millions of cycles per second and higher can be propagated through many solids and liquids. Acoustic energy waves may be partially reflected and partially transmitted at the interface between two media of different elastic properties. The product of material density and sonic wave velocity is known as the acoustic impedance, and the amount of reflection which occurs at the interface between two media is dependent upon the angle of incidence and the amount of change in the acoustic impedance from one medium to the other. This concept of reflection from layers may be generalized to reflection from small regions of arbitrary shape. If the regions of differing impedance are of the order of a wavelength or smaller, the reflection is no longer specular, but diffuse. In this case, the more general term of scattering is used to include both specular and diffuse reradiation of energy. It is also seen that scattering is produced not only by fluctuations in impedance, but also by fluctuations in speed of sound, compressibility, density, and absorption. The net property of an object which describes this phenomenon is called the scattering potential.

These principles have been used for imaging reflecting bodies within a propagation medium. In terms of scattering theory, the direct or forward scattering problem is concerned with a determination of the scattered energy or fields when the value and distribution of the elastic or electromagnetic properties of the body (i.e., scattering potentia) or the distribution of the particles doing the scattering are known. The inverse scattering problem consists in the use of scattered electromagnetic and/or acoustic waves to determine the internal material properties (i.e., scattering potential) of objects from the information contained in the incident and scattered fields. In other words, as defined herein, acoustic imaging using inverse scattering techniques is intended to mean electronic reconstruction and display of the size, shape, and unique distribution of material elastic and viscous properties of an object scanned with acoustic energy, i.e., reconstruction of that scattering potential which, for a given incident field and for a given wave equation, would replicate a given measurement of the scattered field for any source location.

Acoustic imaging through the use of inverse scattering techniques has been a much studied problem in fields which are as diverse as seismic geophysical surveying, nondestructive testing, sonar, and medical imaging. Such inverse scattering techniques would be of particular interest because of the ability to provide accurate quantitative as well as qualitative image values when using such techniques. However, the use of complete inverse scattering techniques in acoustic imaging is generally considered to be so difficult that it has been common to employ methods which lead merely to approximations rather than actual image values. For example, one approach used in holographic imaging and seismic imaging is to "back propagate" the detector field measurement into the object, usually assuming as a model a homogeneous or a one-dimensional layered distribution of wave propagation speed. The images obtained are images of the source of the scattered fields, and thus only indirectly provide an indication of internal structure of material properties. Many of such techniques are described in the *Acoustical Imaging* series, volumes 1-13, published by Plenum Press, Inc.

In the case of medical diagnostic imaging, quantitative tissue characterization based on approximate or theoretically incomplete inverse scattering techniques are now being investigated for inclusion on clinical pulse echo scanners, also known as B-scanners. However, tissue characterization using such scanners is based on 180 degree backscattering from structural and statistical properties of tissues and not on determining absolute tissue properties, per se. The statistical properties of tissues, e.g., texture or the spatial Fourier transform, are often correlated with the state of health or disease and are therefore valuable, but they are not easy to measure quantitatively using present incomplete or approximate inverse scattering techniques. thus, while it is possible with the present state of the art to obtain some quantitative information about tissue properties from B-scans, it is not possible to obtain absolute mechanical properties of such tissues.

In summary, prior art apparatus and methods which have been used to date do not take into account such problems as multiple orders of scattering compensation for refraction, frequency dependent effects of density on scattering properties of the object, changes in acoustic absorption based on changes in frequency of the acoustic energy, or boundary value measurements of the incident field, scattered field, and scattering properties of the object. All of these problems may significantly affect image quality. Yet the prior art has largely ignored these problems by using approximations or assumptions which avoid having to account for such problems when reconstructing the image. Accordingly, it would be an important advance in the state of the art to be able to provide acoustic imaging using inverse scattering techniques which provide an image of the actual material properties of an object (and not just the internal fields) without use of perturbation or other drastic approximations, such as the well-known ray optics, single scattering, Born, or Rytov approximations. Such an apparatus and method are described and claimed herein.

BRIEF SUMMARY AND OBJECTS OF THE INVENTION

The apparatus and method of the present invention provide high-quality images with high-spatial resolution of an object, including the actual internal viscous and elastic properties of the object, derived from acoustic energy propagated through the object and scattered by it. The apparatus and method include means for sending and receiving acoustic energy waves and for reconstructing the image using state-of-the-art electronics to optimize the system's speed and resolution capability. Improvements to resolution quality of the reconstructed image, including accurate quantitative imaging of the actual internal elastic and viscous properties of the object (e.g. density, acoustic speed, and acoustic absorption), are achieved using high-speed computer-aided data analysis baded on new inverse scattering techniques.

It is therefore a primary object of the present invention to provide an improved apparatus and method for acoustic imaging.

Another primary object of the present invention is to provide an apparatus and method for reconstructing acoustic images of the actual internal material properties of an object using inverse scattering techniques, but without degrading image quality through the use of often effectively drastic approximations, such as geometrical or ray acoustic approximations or perturbation theories that include the Born or Rytov approximations.

Another object of the present invention is to provide an apparatus and method for improving the spatial resolution of an image derived from scattered acoustic energy by more accurately taking into account refraction and diffraction effects.

A further object of the present invention is to provide an apparatus and method which is capable of providing high-spatial resolution of elastic and viscous material properties from scattered energy, even though the detected energy has undergone multiple scattering events.

Still another important object of the present invention is to provide an apparatus and method which is capable of providing improved spatial resolution and actual quantitative material properties of an object reconstructed from scattered acoustic energy, but which is still capable of high-speed reconstruction of the images of these properties.

A further object of the present invention is to provide an apparatus and method for obtaining quantitative images of high-quality and high-spatial resolution of multiple elastic and viscous material properties in geometries where the source or receiver locations do not completely circumscribe the object or where the solid angles defined by the source or receivers with respect to the body are small.

A further object of the present invention is to provide quantitative images of speed of sound and attenuation that can be used to correct more conventional images, such as B-scan or synthetic focus for blurring due to refractive and attenuation effects.

These and other objects and features of the present invention will become more fully apparent from the following description and appended claims taken in conjunction with the accompanying drawings.

BRIEF DESCRIPTION OF THE DRAWINGS

FIGS. 4A-4B are schematic diagrams illustrating one embodiment of an electronic system that may be used to implement the apparatus and method of the present invention.

FIGS. 6A-6F are schematic flow diagrams which illustrate an example of one presently preferred method by which the electronic systems of FIGS. 4 and 5 are able to rapidly develop a reconstruction of the image of an object from scattered acoustic energy using inverse scattering techniques.

FIGS. 8A-8L schematically illustrate still another method for implementing inverse scattering techniques using the systems of FIGS. 4 or 5.

Reference is now made to the figures wherein like parts are designated with like numerals throughout.

DETAILED DESCRIPTION

The apparatus and method of the present invention holds promise for many useful applications in various fields, including seismic surveying, nondestructive testing, sonar, and medical ultrasound imaging, to name just a few. For purposes of illustrating the utility of the present invention, the detailed description which follows will describe the apparatus and method of the invention in the context of a system for use in performing ultrasound imaging of human organs, such as the breast. However, it will be appreciated that the present invention as claimed herein may be used in other fields, and is not intended to be limited solely to medical acoustic imaging.

1. The Scanner and Transducer Configuration

Figure 1:
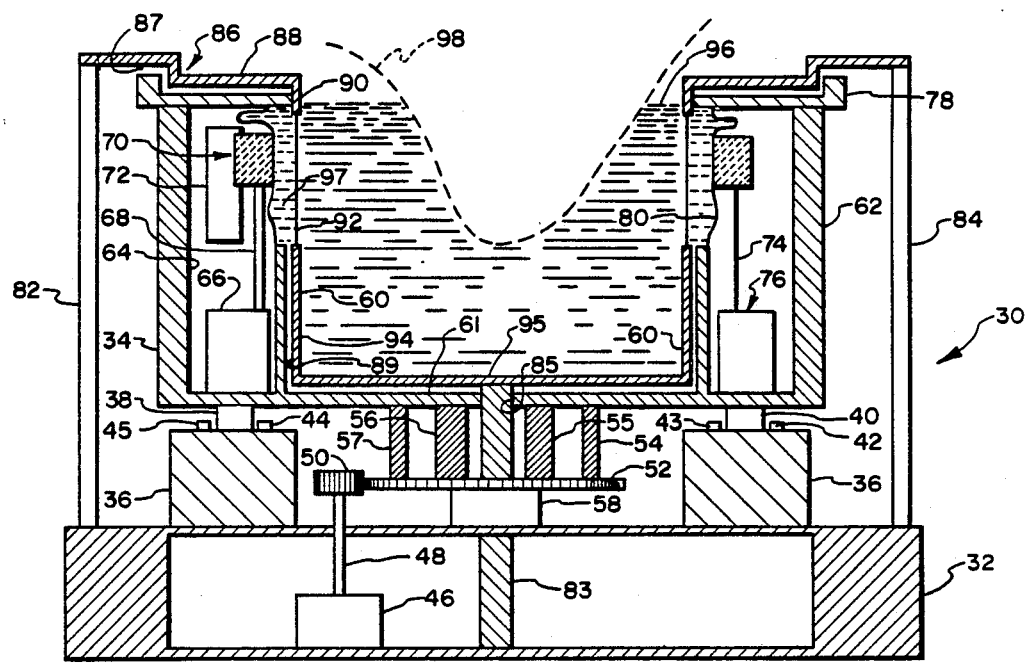
FIG. 1 is a side-elevational view shown partially in cross section which schematically illustrates an acoustic scanner which may be used with the apparatus and method of the present invention.

Reference is first made to FIG. 1 which generally illustrates one type of scanner which may be used to implement the apparatus and method of the present invention for purposes of medical ultrasound imaging of a human breast or other organs. As shown in FIG. 1, the scanning apparatus generally designated at 30 includes a fixed base 32. Wheels 38 and 40 are attached to the underside of a movable carriage base 34. Small shoulders 42-45 formed on the upper surface of cylindrical pedestal 36 define a track along which the wheels 38 and 40 are guided.

A stepping motor 46 mounted within the fixed base 32 is joined by a shaft 48 to a small pinion gear 50. Pinion gear 50 engages a large drive gear 52. Pillars 54-57 are rigidly joined at one end to the top of drive gear 52 and at the opposite end to the underside of movable carriage base 34. Bearing block 58 supports drive gear 52 and movable carriage base 34.

Stepping motor 46 may be operated to turn the drive gear 52 which in turn will cause the movable carriage base 34 to rotate on top of the cylindrical pillar 6 within the tracks defined by shoulders 42–45. As hereinafter more fully described, rotation of the movable carriage base 34 may be employed to insure that an object is fully scanned from every possible angle.

With continued reference to FIG. 1, it will be seen that movable carriage base 34 has an inner cylindrical wall 60 and an outer cylindrical wall 62. The outer wall 62 and inner cylindrical wall 60 of movable carriage base 34 define a generally cylindrical chamber 64. Vertical drive motor 66 is mounted within chamber 64 and is connected by a shaft 68 to a circular ring of transducer arrays generally designated at 70. Vertical drive motor 66 permits the circular ring of transducer arrays 70 to be vertically adjusted. Slide bracket 72 is mounted within the chamber 64 and serves to slidably guide the ring of transducer arrays 70 when it is vertically adjusted.

The ring of transducer arrays 70 is electrically connected through line 74 to components of an electronic system which may be housed in part within the chamber 64, as schematically indicated at 76. As hereinafter more fully described, the electronic system is used to control transmission and reception of acoustic signals so as to enable reconstruction therefrom of an image of the object being scanned.

Circular bracket 78 is attached to the top of the outer wall 62 of movable carriage base 34. A flexible, transparent window 80 extends between circular bracket 78 and the inner cylindrical wall 60 so as to enclose the transducer arrays 70 and stepping motor 66 within the chamber 64. The length of flexible window 80 is greater than the distance between bracket 78 and inner cylindrical wall 60. Window 80 thus serves as a flexible yet water-tight seal which permits vertical motion of the transducer arrays 70 for purposes of vertical focusing. Acoustically transparent window 80 may be made of any suitable material, such as plastic or rubber.

A stationary water tank generally designated 86 is adapted to fit within the movable carriage base 34. Water tank 86 consists of a fixed top plate 88 rigidly attached to vertical support bars 82 and 84. Support bars 82 and 84 are mounted on the fixed based 32. The length of support bars 82 and 84 is chosen such that the fixed top plate 88 of water tank 86 will be slightly suspended above the bracket 78 of movable carriage 34. Thus, a space 87 is provided between bracket 78 and fixed top plate 88. Additionally, a space 89 will be provided between side 94 and bottom 95 of water tank 86 and cylindrical wall 60 and bottom 61 of movable carriage 34. A third support bar 83 extends through a central hole (not shown) provided in block 58 and drive gear 52. Support bar 83 also extends through a water-tight opening 84 provided in the bottom 61 of movable carriage 34. Support bar 83 thus helps to support water tank 86 in spaced relation from movable carriage 34. Since water tank 86 is suspended in spaced relation from movable carriage base 34, water tank 86 will remain stationary as movable carriage 34 is rotated. As hereinafter more fully described, rotation of the carriage 34 permits the transducer arrays 70 to scan the object 98 from every possible position around the object 98.

Fixed top plate 88 has a short downwardly extending lip 90 which extends over the end of circular bracket 78. A rubber-covered window 92 extends between the lip 90 and side 94 of the water tank. Window 92 encloses within space 89, water 977, or some other suitable acoustic medium so as to acoustically couple the transducer array 70 to the water 96 contained in tank 86. The rubber-covered window 92 also permits acoustic energy signals to be transmitted therethrough by the transducer arrays 70 and insures that the patient will be protected in the event window 92 should be broken.

The scanning apparatus generally described above may be employed to scan various part os the human anatomy as, for example, a patient's breast, as schematically illustrated at 98.

Figure 2:
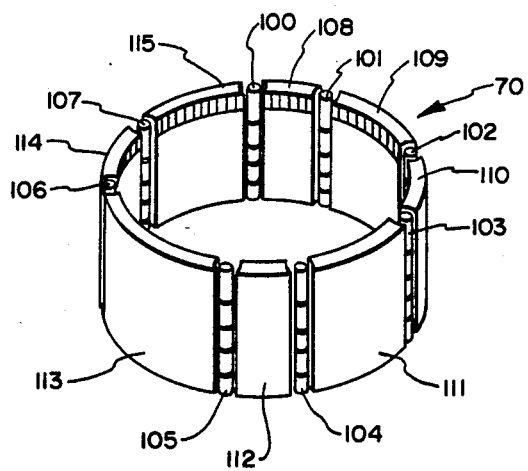
FIG. 2 is a perspective view illustrating one type of configuration which may be used for the transducer arrays employed in the scanner of FIG. 1.
Figure 3:
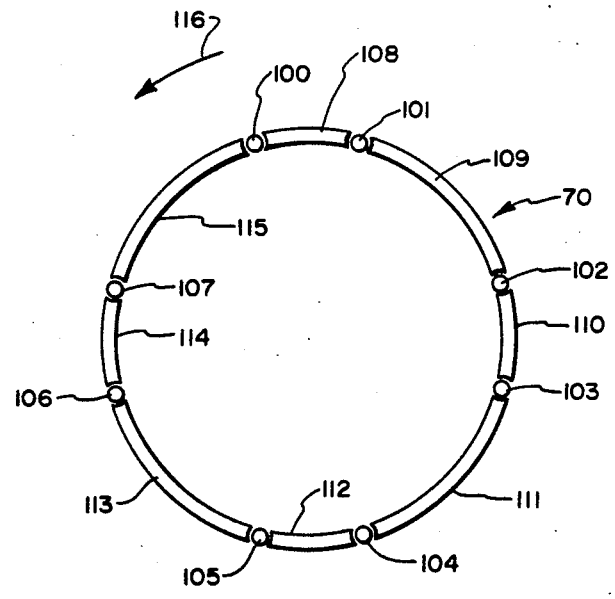
FIG. 3 is a top view of the transducer arrays shown in FIG. 2.

Reference is next made to FIGS. 2–3. FIG. 2 generally illustrates one suitable type of transducer configuration for the transducer arrays of FIG. 1. As shown in FIG. 2, the transducer configuration consists of eight transmitter arrays 100–107 and eight corresponding receiver arrays 108–115. The transmitter array 100–107 are thin, cylindrically-shaped transducer arrays which provide point-source or line-source segment transmission of acoustic energy. The receiver arrays 108–115 are arcuately shaped arrays which are interposed between each pair of transmitter arrays 100–107. For purposes hereinafter more fully described, every other receiver array (e.g.. receiver arrays 108, 110, 112 and 114) has a shortened arcuate length.

Each of the transducer arrays 100–115 may be any of several well-known types of transducers. For example, transducers 100–115 may be piezoelectric transducers which produce ultrasound energy signals directly from high-frequency electrical voltages applied to the transducer. Alternatively, the transducer arrays 100–115 may be magnetostrictive transducers having a magnetic coil (not shown) which receives the electrical oscillations and converts them into magnetic oscillations which are then applied to the magnetostrictive material to produce ultrasound energy signals.

With continued reference to FIG. 1, it will be seen that the transducer arrays 100–115 are arranged so as to form a cylindrical ring of arrays which encircles the object 98. By encircling the object with the transducer arrays 100–115, the arrays 110–115 may be quickly commutated by either mechanical methods, electronic methods or by a combination of both methods so as to completely scan the object in a much shorter time. In the illustrated embodiment, commutation is achieved by both mechanical rotation by stepping motor 46 and by electronic triggering of transmitter arrays 100–117 in sequence, as described more fully below.

Commutation of the transmitter arrays 100–107 permits acoustic energy to be transmitted from every possible position about the object, thus insuring that the data received (i.e. scattered acoustic energy) is complete. Commutation of the receiver arrays 108–115 insures that all spaces between receiver arrays 108–115 (known as "sound holes") will be covered, thus providing for accurate collection of all acoustic energy that is transmitted through or scattered by the object 98. However, commutation of the receiver arrays 108–115 is not necessary where transmitter arrays 100–107 are also used to receive acoustic signals. The circular configuration of transducer arrays 100–115 permits certain parts of the body to be scanned which would otherwise be inaccessible because of bones or other obstructions of the tissue.

The method for commutating the arrays 100-115 is best understood by reference to FIG. 3. First, each of the transmitter arrays 100-107 is sequentially triggered so as to transmit acoustic energy. Immediately after each transmitter array 100-107 is triggered, arrays 108-115 receive acoustic energy signals that have been either transmitted through or scattered by the object being scanned. Once this procedure has been followed for each of the transmitter arrays 100-107, the ring of arrays 70 is then mechanically rotated counterclockwise through a small angle, as schematically represented by arrow 116. The mechanical rotation is achieved by the stepping motor 46 (see FIG. 1) which rotates the movable carriage base 34, as described above.

After rotation of the arrays 100-115 to a second position, each of the transmitter arrays 100-107 is again sequentially triggered and data are again collected through receiver arrays 108-115. This procedure is repeated until acoustic energy has been transmitted at each possible point about the object.

Where the arrays 100-107 are used only for transmitting acoustic energy, a second series of rotations must then be effected to cover the sound holes between each pair of receiver arrays 108-115. For example, by rotating transmitter array 101 to the position occupied by the transmitter array 100, receiver arrays 109, 111, 113 and 115 will, because of their longer arcuate length, cover the spaces previously occupied by transmitter arrays 101, 103, 105 and 107. This procedure is repeated until all sound holes have been covered.

It should be noted that for a fixed circumference by decreasing the length of each array and increasing the number of arrays, electronic commutation may be used to reduce the angle through which the ring of transducer arrays must be rotated to achieve complete collection of both echo and transmission data.

It should also be noted that, in principle, no mechanical rotation of the array of detectors is necessary if every element is small enough and can be made to act as either a receiver or transmitter. Such an arrangement is more expensive than the technique illustrated in FIGS. 1, 2, and 3.

2. The Electronic System

Reference is next made to FIGS. 4A-4B which schematically illustrate an electronic system which may be used to implement the apparatus and method of the present invention. As hereinafter more fully described, the electronic system generates the acoustic energy that is propagated through and scattered by the object 98. The electronic system thereafter detects and processes the acoustic energy signals that are scattered by and transmitted through the object 98, and then communicates the processed signals to a computer (CPU) which interprets the signals and outputs the result in the form of a visual display or printed output.

In the transmission mode, CPU 118 causes an oscillator 128 to output a waveform which is amplified by a power amplifier 130 before being sent through multiplexer 132 to one of the transmitters. CPU 118 controls the multiplexer 132 so as to sequence each transmitter array 100-107 used to generate the acoustic energy propagated through the acoustic medium and object. If desired, after it is amplified, the waveform can also be input to an impedance matching transformer (not shown) and to a series of RC or RLC networks connected in parallel across the transmitter arrays 100-107 as illustrated and described in U.S. Pat. No. 4,222,274 (hereinafter the Johnson '274 patent), which is incorporated herein by reference. The impedance matching transformer may be used to achieve maximum power transfer while the RC or RLD networks may be used to distribute power across each transmitter array 100-107 in a way that decreases the side lobes in the transmitted signal.

Each of the acoustic receivers 108-115 (FIG. 2) are connected through a multiplexer 134 which is also controlled by CPU 118. In the receive mode, the detected signals may also be input through a delay line (not shown) to an analog adder and time variable gain circuit (not shown) to vertically focus the signals and to compensate for signal attenuation, as shown and described in the Johnson '274 patent. CPU 118 causes multiplexer 134 to sequence in turn each of the acoustic receivers 108-115 so as to gather transmitted or scattered acoustic energy around the entire circumference of the object. From receiver multiplexer 134, detected acoustic energy signals are amplified by a preamplifier 136 which may be used to logarithmically amplify the detected signal to reduce storage space required for each signal after it is digitized. The amplified signal is then processed by a phase detector 138.

The operation and components of phase detector 138 are best illustrated in FIG. 4B. As there shown, phase detector 138 receives the amplified signal as schematically represented by line 137 on which the signal is input to multipliers 154 and 156. The signal generated by oscillator 128 is input as shown at line 150 to one of the multipliers 156, and the signal from oscillator 128 is also shifted 90 degrees by the phase shifter 152 and then input as shown at line 153 to the other multiplier 154. Thus, each signal detected at the acoustic receivers is multiplied at multiplier 154 by a signal which is 90 degrees out of phase with the signal which is used to multiply the detected signal at the other multiplier 156. During the receive mode, the switch controller 158 and reset 166 are controlled as shown at line 123 by CPU 118 so that controller 158 closes each switch 164 and 165 after integrators 168 and 170 are reset. The resulting signals from multipliers 154 and 156 are then filtered by low-pass filters 160 and 162 and integrated by integrators 168 and 170. The integrated signals are then output, as shown at lines 139 and 140 to the analog to digital converters (ADCs) 142 and 143 (see FIG. 4A). The two signals which are output by phase detector 138 electronically represent the real and imaginary mathematical components of the acoustic signals which are detected at the acoustic receivers 108-115.

Once the received signals have been digitized, they are input and stored in the memory of an array processor 120. Alternately, a parallel processor or other special purpose high-speed computational device may be used for even higher computational speed. As hereinafter more fully described, CPU 118 in combination with the array processor 120 are programmed to then reconstruct the acoustic image using inverse scattering techniques, several alternatives of which are described more fully in Examples 1-3 of section 3 below. Once the acoustic image is reconstructed, it may be output either visually at a display 124 or in printed form at printer 122, or stored on a disc or other storage medium 123. Mechanical scan devices represented at 126 correspond to the motors 46 and 66 (FIG. 1) for controlling commutation and vertical positioning at the transmitter and receiver arrays 100-107 and 108-115, and are controlled by CPU 118.

Figure 4E:
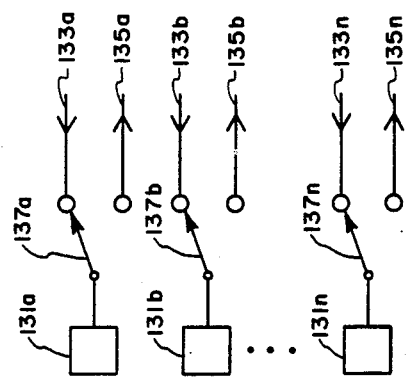
FIG. 4E is an electrical schematic diagram showing how the elements in FIGS. 4C and 4D may be switched to act as either a transmitter or receiver by use of an active switch.
Figure 4F:
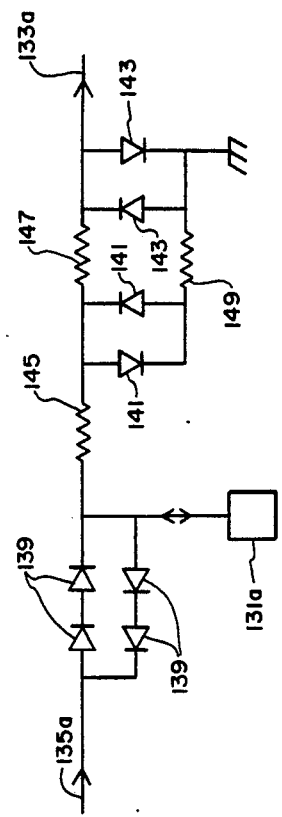
FIG. 4F illustrates how a passive network may be used to allow each element of an array to be used for both transmitting and receiving.
Figure 4C:
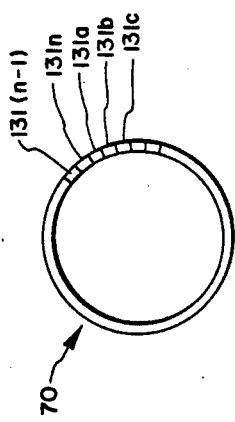
FIG. 4C is a schematic illustration of a circular transducer array showing a method of electronically multiplexing the array elements to eliminate the need for mechanical rotation.
Figure 4D:
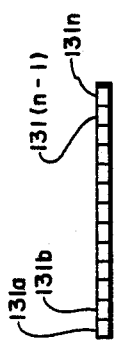
FIG. 4D is a further illustration of pure electronic multiplexing of a linear transducer array.

Reference is next made to FIGS. 4C–4F which schematically illustrate how electronic multiplexing may be used to eliminate the need for mechanical rotation, thus further enhancing system performance. In particular, FIG. 4C shows n transducer elements 131a through 131n of a circular array closely spaced to form a continuous array surrounding the body. The array is shown as a one-dimensional structure, but clearly could be a two-dimensional structure as in FIG. 2. FIG. 4D illustrates the n elements 131a through 131n arranged in a linear fashion. It is also clear that a planar or checkerboard two-dimensional array of elements could be used.

Such one-dimensional and two-dimensional arrays of receivers and transmitters have a direct application to advanced medical imaging instruments where motion of the array is undesirable or in seismic exploration in which such movements are difficult. FIG. 4E illustrates how each element 131a through 131n may be switched to either a transmitter circuit or a receiver circuit. Here, for example, element 131a is switched by switch 137a to either a transmitter circuit 133a or a receiver circuit 135a. FIG. 4F shows how a passive network of diodes and resistors may be used to allow a single element to act as either a transmitter or a receiver, or in both capacities. For example, in the transmit mode, diodes 139 are driven into conduction by transmit signal on line 135a. With two silicon diodes in series in each parallel leg, the voltage drop is a few volts. Thus, for an applied transmit signal of 20 volts or more, only a small percentage of signal power is lost across diodes 139. Diodes 139 are arranged in a series parallel network so that either polarity of signal is passed to transducer element 131a with negligible loss. In the transmit mode, resistors 145, 147, and 149 and diodes 141 and 143 prevent excessive and harmful voltage from appearing at output 133a that leads to the preamplifier multiplexer, or analog-to-digital circuits that follow. In operation, resistor 145, diode 141, and resistor 149 act as a voltage divider for the large transmit voltage present at the transducer element 131a. Diodes 141 are arranged with opposing polarity to provide a path for any polarity of signal above their turn on voltage of about 0.7 to 1.0 volts. The values of resistors 145 and 149 are typically so that the impedance of resistor 145 is greater than or equal to that of the internal impedance of transducer element 131a. Resistor 149 is chosen to be some fraction of resistor 145, such as one-fifth. Resistor (resistor 147) typically is chosen to be about equal to the resistance of resistor 149. Thus, during transmission, the voltage appearing at output 133a is only the conduction voltage drop across diodes 143.

In the receiving mode, signals received at transducer element 131a are typically less than one diode voltage drop (about 0.7 volt) and thus are isolated from transmitter 135a, since point 135a is a ground and diodes 139 are not conducting. Diodes 141 and 143 are not conducting and therefore output 133a is not shunted. Thus, the preamplifier following 133a would only see an impedance of resistor 145 plus resistor 147 plus that of the transducer element 131a. In practice, resistor 145 plus resistor 147 can be made about equal to or less than the impedance of transducer element 131a to minimize signal loss. It is clear that the principles illustrated in FIGS. 4C–4F may also be applied in the case of wide bandwidth signal transmission as described further below in connection with FIGS. 5A–5B.

Figure 5A:
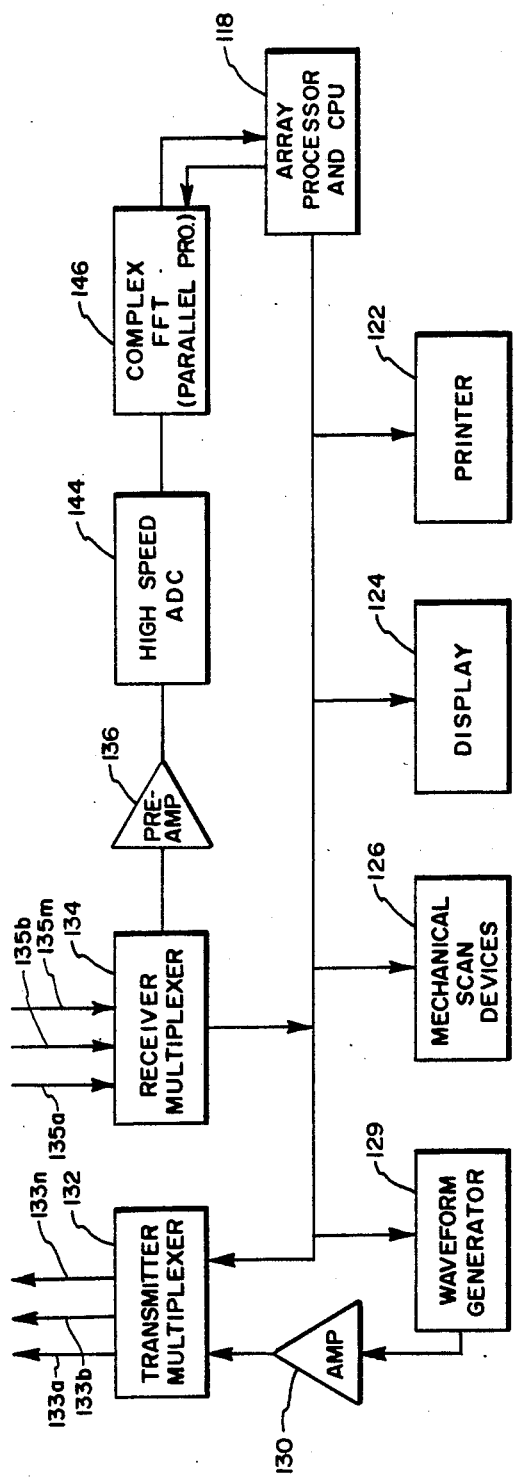
FIGS. 5A-5B are schematic diagrams illustrating another embodiment of an electronic system that may be used to implement the apparatus and method of the present invention.
Figure 5B:
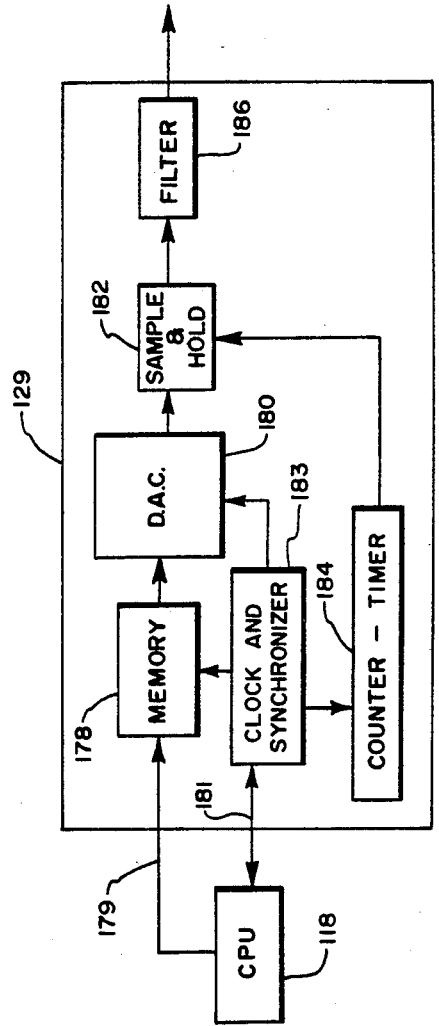

FIGS. 5A and 5B schematically illustrate another electronic system which can be used to implement the apparatus and method of the present invention. In FIG. 5A, oscillator 128 has been replaced by waveform generator 129 that can produce repetitive narrow bandwidth signals or a wide bandwidth signal. The advantages of using a suitable wide bandwidth signal is that in one transmit-receive event, information at all frequencies of interest may be collected. Typically, it will be preferable to scan the object under consideration with signals having several different frequencies. This may be especially true in cases where it is not possible to encircle the object with a ring of transducer arrays, as in the case of seismic imaging. Moreover, by using multiple frequencies, it will typically be possible to obtain more data for use in reconstructing the image. The lowest frequency used for the signal must be such that the wavelength of the signal is not significantly larger than the object to be imaged. The highest frequency must be such that the acoustic signal may be propagated through the object without being absorbed to such an extent as to render detection of the scattered signal impossible or impractical. Thus, depending upon the absorption properties and size of the object which is to be scanned, use of multiple frequencies within the range indicated will typically enhance the ability to more accurately reconstruct the image of the object.

The use of multiple frequencies or signals containing many frequencies also has the advantage of obtaining data that may be used to accurately reconstruct frequency dependent material properties, such as the Taylor series expansion coefficients of absorption as described in section 4 below.

In the electronic system of FIG. 4A, in order to scan the object using multiple frequencies, the frequency of oscillator 128 must be changed several times at each transmitter position. This increases the time involved in transmitting and detecting the scattered acoustic energy from which the image is reconstructed. In the electronic system of FIG. 5, a special waveform is used which inherently includes multiple frequencies within it. The type of waveform generated by waveform generator 129 may be the well-known Tanaka-Iinuma kernel or the Ramachandran and Lakshiminaraynan kernel, as illustrated and described in the Johnson '274 patent. Swept frequency signals such as the well-known frequency modulated chirp or other types of waveforms could also be used to provide acceptable results.

As shown in FIG. 5B, the waveform generator 129 basically comprises five elements. An electronic memory device 178 is connected to the CPU 118 through read-and-write lines 179 and 181. CPU 118 determines the numerical value for a series of discrete points on the selected waveform. These numerical values are stored in binary form in memory device 178. Each of the discrete values stored in the memory device 178 is then sent to a digital to analog converter (DAC) 180. DAC 180 then transforms each of these digital values into a corresponding analog pulse which is then input to a sample and hold circuit 182. Sample and hold circuits, such as that schematically illustrated at 182, are well-known in the art and operate to hold each analog signal for a predetermined period of time. Counter-timer 184 is used to control the amount of time that each signal is held by the sample and hold circuit 182. Clock and synchronizer 183 is triggered by computer 118 and advances the memory address in memory 178, synchronizes the DAC 180, and controls the sample and hold 182.

With each clock pulse from counter-times 184, the sample and hold circuit 182 retrieves one of the analog signals from DAC 180 and then holds the value of that signal for the duration of the clock pulse. Sample and hold circuit 182 thus outputs the approximate shape of the desired waveform which is then input to a low pass filter circuit 186 which is used to smooth the shape of the waveform before amplification and transmission through multiplexer 132 to one of the transmitters.

The electronic system of FIG. 5A also differs from the system shown in FIG. 4A in that the amplified analog signals output by the preamplifier 136 are digitized by a high-speed analog-to-digital converter 144 rather than being input to a phase detector. The digitized signals are then transformed by a complex fast Fourier transform (hereinafter "FFT") operation provided by a parallel processor 146 prior to being input and stored in the memory of the CPU 118. As described further in section 3 below, CPU 118 then reconstructs the image using a novel inverse scattering technique. Use of array processor 120 with CPU 118 in FIG. 4A and parallel processor 146 with CPU 118 in FIG. 5A is arbitrary and in principle either array processor 120 or parallel processor 146 or special purpose hard wired computational hardware could also be used in either FIG. 4A or 5A to accomplish the image reconstruction, as described further in sections 3.

3. The Method of Image Reconstruction Using Inverse Scattering Techniques

In order to reconstruct the acoustic image of an object which has been scanned with acoustic energy, it is first necessary to acquire a complete set of signals which have been scattered and transmitted through the object. As previously described, this may be accomplished in the illustrated embodiment by encircling the object 98 (see FIG. 1) with a ring of transducer arrays 70 (see FIGS. 2-3). Each transmitter array 100-107 is sequentially triggered in a first position so as to propagate a series of acoustic signals at multiple frequencies. After each transmitter array 100-107 is triggered, receiver arrays 108-115 are used to receive the scattered acoustic energy. The ring of transducer arrays 70 is then mechanically or electronically commutated as described previously and the process is then repeated. The ring of transducer arrays 70 is commutated as many times as needed in order to transmit acoustic signals at multiple frequencies from each point around the object. In other words, data are transmitted at multiple frequencies and received at each position around the object 98 so as to insure a complete set of both echo and transmission data.

After the scattered acoustic energy signals have been detected by the receiver arrays, the signals are processed, as described above in connection with FIGS. 4 and 5, in order to develop an electronic analog that represents the real and imaginary components of each signal and in order to digitize each analog signal prior to its input to the CPU 118. CPU 118 is programmed to reconstruct the acoustic image of the object using novel inverse scattering techniques. The resulting acoustic image thus contains information which can be used to display not only the size and shape of the object, but also the internal material properties at each scattering point within the object. These properties, including tissue density, absorption, and speed of sound, can be used to provide a much more accurate overall picture which shows not only the size and shape of the object, but also the state at each scattering point within the object. This additional information can be highly useful in helping to more accurately diagnose the state of the tissue in the case of medical ultrasound imaging, or in providing much additional useful information in other fields such as seismic surveying or the like.

To better understand the data processing steps used to implement the inverse scattering techniques used in reconstructing an acoustic image in accordance with the present invention, it is helpful to examine the implementation of the data processing steps using several different examples. Accordingly, reference is next made to a description of several presently preferred examples for implementing the data processing techniques, although it should be understood that the apparatus and method of the present invention are not necessarily limited to the examples which follow.

EXAMPLE 1

Image Reconstruction in the Case of Simple Scattering Potentials for Single and Multiple Frequency Data In this example, a model is described for reconstructing an image from the special scattering potential given by $\gamma = 1 - c_o^2/c(\underline{x}) + i2\alpha(x)c_o^2[\omega c(\underline{x})]$, where $\alpha(x) = \alpha_o \omega^{n_o}$. This scattering potential does not include the effect of inhomogeneous density variations (i.e., frequency dependent absorption), but it does include the effect of a single term of frequency dependent absorption. In many materials, $n_o = 1$, i.e., $\alpha(x) = \alpha_o \omega$, is a good approximation to the frequency dependence of absorption.

Two important equations for modeling the propagation of sound through an inhomogeneous fluid-like body immersed in a homogeneous fluid bath are the Helmholtz wave equation (the inhomogeneous form) and the Riccati wave equation. These equations are often used to model the scattering of sound by such a body and are related by the transform $p(\underline{x}) = p_o(\underline{x})e^{w(x)}$ and are given, respectively, by $$\nabla^2 p(\underline{x}) + k_o^2 p(\underline{x}) = k_o^2 \gamma(x) p(\underline{x}) \tag{1a}$$

$$\nabla^2 \omega(\underline{x}) + \nabla\omega(\underline{x})\cdot\nabla\omega(\underline{x}) + 2\nabla\ln p_o(\underline{x})\cdot\nabla\omega(\underline{x}) - k_o^2 \gamma(\underline{x}) = 0 \tag{1b}$$

where $k_o^2 = \omega^2/c_o^2$, $c_o^2$ is a constant speed of sound (usually taken in the fluid bath), $\omega$ is constant angular frequency, $p(\underline{x})$ is acoustic pressure, and $p_o(\underline{x})$ is acoustic pressure in the incident field. Here, $\gamma$ is the scattering potential given by $$\gamma = 1 - c_o^2/c^2(\underline{x}) + i2c_o^2\alpha(\underline{x})/[\omega c(\underline{x})] \tag{2a}$$

where $c(\underline{x})$ is the speed of sound in the body. Here, $\alpha$ contains absorption information and is essentially equal to the linear absorption coefficient for weak scattering, e.g., in soft tissues. The equations above may be modified to include variations in density $\rho$ within the body, but such generalization leads to more complicated equations. Fortunately, they can be transformed to a form equivalent to equation (1a), except $p$ in equation (1a) is now replaced by $p(x)[\rho(x)]^{\frac{1}{2}}$, where $\rho(x)$ is the density. Since the scattered field is usually measured in the homogeneous bath or in material where $\rho$ is a known constant, equations (1a) and (1b) may still be used to find a new and more complete scattering potential $\gamma[c(\underline{x}), \rho(\underline{x}), \alpha(\underline{x}), \omega]$. This more complete scattering potential containing density is given by $$\gamma = 1 - c_o^2/c^2(x) + i2c_o^2\alpha(x)/[\omega c(x)] + [c_o^2/\omega^2]\rho^{\frac{1}{2}}\nabla^2\rho^{-\frac{1}{2}}. \tag{2b}$$

A model for determining the scattering potential given by equation (2b) is described in Example 2 below.

Although equations (1a) and (1b) are equivalent as related by the above transform, they have different mathematical properties and physical interpretations. If p is the total pressure field and if $p_o$, the incident pressure field, is defined to be the field in the absence of the body, then w/i can be given a physical interpretation and is the complex phase difference between the total field and the incident field. The quantity $w/ik_o$ has dimensions of length and may be considered to be like an optical path length. The quantity $w/ik_oc_o=w/i\omega$ has units of time and may be considered to be an average time of arrival of the scattered field. For complex objects, these intuitive interpretations may become difficult to visualize or use, but the simple idea of the real part of w/i being a phase shift and the imaginary part of w being the ratio of the moduli of incident and the total fields is still valid. For ultrasound computed tomography (often abbreviated UCT) in soft tissues, the scattering potential $\gamma$ is usually small, e.g., $[|\gamma| \leq 0.1]$ is typical, and the change in p per wavelength due to attenuation is small; therefore, w is a more slowly changing function than p. This may reduce the sampling frequency to represent w or lead to greater accuracy in determining w at a given sampling frequency. Thus, for UCT, linearizing equation (1b), i.e., the Rytov approximation, produces superior images as opposed to linearizing equation (1a), i.e., the Born approximation.

Historically, equations (1a) and (1b) have been used to provide UCT images only when modified by certain approximations, such as those of Born or Rytov. Such approximation solutions are described by Wolf[1], Mueller et al.[2] and Norton et al.[3] As noted above, the results achieved by using such approximations do not lead to reconstruction of an acoustic image that accurately represents the actual internal material properties of the object. However, in the method employed in this invention, the Born or Rytov approximations are not used and yet the resulting acoustic image contains all orders of scattering information.

[1]Wolf, E., "Three-Dimensional Structure Determination of Semitransparent Objects from Holographic Data," *Optics Commun.* 1, 153-156 (1969).
[2]Mueller, R. K., Kaveh, M., and Wade, G., "Reconstructive Tomography and Applications to Ultrasonics," *Proc. IEEE* 67, 567-587 (1979).
[3]Norton, S. J. and Linzer, M., "Ultrasonic Reflectivity Imaging in Three Dimensions; Exact Inverse Scattering Solutions for Plane, Cylindrical, and Spherical Apertures," *IEEE Trans. Biomed. Engineering* BME-28, 202-220 (1981).

The following explanation of notation is given to facilitate obtaining an understanding of the invention. The scattering potential $\gamma$ changes from point to point within an object or body as well as changing with frequency of the incident field. Thus, $\gamma_{\omega j}$ means $\gamma_\omega(\underline{x}_j)$ or the scattering potential at pixel j or point j for incident field at frequency $\omega$. $\gamma_{10\tau}$ then means the set of all values of $\gamma_{\omega j}$ at all j and also may be considered to be the vector composed of all values of j, i.e., $\gamma_\omega = \{\gamma_{\omega j}\}$. Likewise, $\gamma$ is a vector composed of samples at all $\underline{x}_j$ and at all frequencies, i.e., $\gamma = \{\gamma_\omega\} = \{\{\gamma_{\omega j}\}\}$. To emphasize the vector nature of a variable, a bar is placed underneath said variable, e.g., $\underline{\gamma} = \{\gamma_\omega\} = \{\{\gamma_{\omega j}\}\}$ above, the curly brackets { } are placed around a vector component, e.g., $\{\gamma_\omega\}$, to indicate that the complete set of components, i.e., a vector, is called for. The same notation will apply to other variables, e.g., the fields $f_{\omega\phi j}$, as well.

In the case of the Helmholtz equation (1a), let f represent some field such as p or $[p\rho^{\frac{1}{2}}]$. Then the Helmholtz wave equation (1a) in f may be transposed to an integral equation with built in boundary conditions, as follows:

$$f_{\omega\phi}^{(sc)}(\underline{x}) \triangleq f_{\omega\phi}(\underline{x}) - f_{\omega\phi}^{(in)}(\underline{x}) \qquad (3)$$
$$= -\int k_o^2 \gamma_\omega(\underline{x}') f_{\omega\phi}(\underline{x}') g(|\underline{x}-\underline{x}'|) d^Q\underline{x}'$$

Here the symbol $\triangleq$ means "equal by definition" or "identical to by definition." Here $f_{\omega\phi}^{(sc)}$ is the scattered field, $f_{\omega\phi}^{(in)}$ is the incident field, $\phi$ is the source location, $\omega$ is the frequency, and $g(\cdot)$ is the outward-going-wave Green's function. Q is the dimension of the space. Equation (3) may be transformed into a system of algebraic equations by expanding the product $k_o^2\gamma_\omega(\underline{x}')f_{\omega\phi}(\underline{x}')$ from equation (3) by a set of basis functions. The result is a set of detector or measurements equations given by $$f_{\omega\phi m}^{(sc)} = \sum_{j=1}^{N} \gamma_{\omega j} f_{\omega\phi j} D_{\omega m j} \triangleq P[\underline{\gamma}]. \qquad (4)$$

$$m = 1, \ldots, M$$
$$\phi = 1, \ldots, \Phi$$
$$\omega = 1, \ldots, \Omega$$

and a set of field constraint equations inside the body at point l given by $$f_{\omega\phi l}^{(sc)} \triangleq f_{\omega\phi l} - f_{\omega\phi l}^{(in)} = \sum_{j=1}^{N} \gamma_{\omega j} f_{\omega\phi j} C_{\omega l j} \qquad (5)$$

where $f_{\omega\phi l} = f_{\omega\phi}(\underline{x}_l)$ and $f_{\omega\phi l}^{(in)} = f_{\omega\phi}^{(in)}(\underline{x}_l)$ are the actual values of the field scattered at a point $\underline{x}_l$ in the object, and $f_{\omega\phi m}^{(sc)}$ is the detected field at points $\underline{x}_m$. Although $C_{\omega l j} = D_{\omega l j}$, a separate symbol $D_{\omega m j}$ is used to correspond to measurment point $\underline{x}_m$ on a detector. $C_{\omega m j}$ and $D_{\omega m j}$ are constants given by $$C_{\omega\mu j} \triangleq \int \psi_j(\underline{x}' - \underline{x}_j') g_\omega(|\underline{x}'-\underline{x}|) d^\alpha\underline{x}' \qquad (6a)$$

The functions $\psi_j(\underline{x}') \triangleq \psi(\underline{x}' - \underline{x}_j')$ belong to a basis set $\{\psi_j(\underline{x}')\}$.

A convenient basis set for calculation is the sinc basis set which for a space of dimension Q is given by $$\psi_j(\underline{x}') = \prod_{q=1}^{Q} \sin[\pi(x_q' - n_{qj}h)/h]/[\pi(x_q' - n_{qj}h)/h] \qquad (6b)$$

where $\underline{x}'$ is the column vector that locates the continuously variable point given by the coordinates $(x_1', x_2', \ldots, x_Q')$, i.e., $$\underline{x}' = [x_1', x_2', \ldots, x_Q']^T \qquad (6c)$$

and where j represents a vector $\underline{x}_j'$ located at fixed coordinates $(n_{1j}h, n_{2j}h, \ldots, n_{Qj}h)$, i.e., $$\underline{x}_j' = [n_{1j}h, n_{2j}h, \ldots, n_{Qj}h]^T \qquad (6d)$$

Equations (4) and (5) must be solved as a set. However, this does not preclude using a method of alternately solving equation (4) for $\{\gamma_{\omega j}\}$ with $\{f_{\omega\phi j}\}$ fixed and then solving equation (5) for $\{f_{\omega\phi j}\}$ with $\{\gamma_{\omega j}\}$ fixed. In principal, it does not matter which equation is solved first to start the iteration. In Examples 1, 2, and 3 that follow, the convention is followed by solving for $\{f_{\omega\phi j}\}$ first and for $\{\gamma_{\omega j}\}$ second for each iterative cycle.

If the scattering potential $\gamma_{\omega j}$ is small enough (which is the case for medical ultrasonic and seismic imaging), a fixed point method may be used to solve equation (5) with $\gamma$ fixed by the following iterative scheme:

$$f_{\omega\phi l}^{(k+1)} = \beta\left[f_{\omega\phi l}^{(in)} + \sum_{j=1}^{N} C_{\omega l j} f_{\omega\phi j}^{(k)} \gamma_{\omega j}^{(n)}\right] + (1-\beta)f_{\omega\phi l}^{(k)} \quad (7a)$$

$$0 < \beta \leq 1$$

Here, $\gamma_{\omega j}^{(n)}$ is a trial guess for $\gamma_{\omega j}$, and $f_{\omega\phi j}^{(k)}$ is the k-th guess for f. If the spectral radius of the matrix $[\beta c_{\omega l j}\gamma_{\omega j}+(1-\beta)\delta_{lj}]$ is less than unity, equation (7) will converge. A nearly optimum $\beta$ is found by a search method. For medical ultrasound or seismic work, a value of $\beta=1$ should work in most cases.

It is useful to define the residual of an equation, such as equation (5), as the value of the right-hand side minus the value of the left-hand side. For example, here the residual for the field equations may be written $$r_{\omega\phi l}^{(fld)} = f_{\omega\phi l}^{(k)} - \left[f_{\omega\phi l}^{(in)} + \sum_{j=1}^{N} C_{\omega l j} f_{\omega\phi j}^{(k)}\gamma_{\omega j}^{(n)}\right] \quad (7b)$$

It is useful to consider $\{r_{\omega\phi l}^{(fld)}\}$ as a column vector with components $r_{\omega\phi l}^{(fld)}$. Then the norm of $\{r_{\omega\phi l}^{(fld)}\}$ may be defined according to standard numerical analysis practice. A useful norm is the "two norm" defined by $\|\{x_i\}\|_2 = (\Sigma |x_i|^2)^{\frac{1}{2}}$. This norm is often written in abbreviated notion as $$\|x_i\| = \left(\sum_i |x_i|^2\right)^{\frac{1}{2}}.$$

A generalization is possible to the p norm given by $$\|x_i\|_p = \left(\sum_i |x_i|^p\right)^{1/p}.$$

For the purposes of this example, the one norm or two norm are more useful. Convergence of equation (5) may then be verified by examining the norm of the residual r of equation (7b). A similar concept is described further below in the iterative scheme for testing of convergence of equation (18).

The sum in equation (7) is a convolution of $C_{\omega\mu j}$ with $\gamma_{\omega j}f_{\omega\phi j}$, since $C_{\omega\mu j}$ is a function of $|\underline{x}_\mu - \underline{x}_j'|$ by inspection of equation (6). The convolution in equation (6) may be performed in a relatively fast operation by use of the convolution theorem and using a fast Fourier transform (FFT) operation. Several iterations of equation (7) with fixed $\gamma_{\omega j}^{(n)}$ will lead to a best fit of the internal field of $f_{\omega\phi}$ to a particular $\gamma_{\omega j}^{(n)}$. But it is not necessarily correct and must be updated. This suggests that $f_{\omega\phi l}$ be updated for a given fixed $\gamma_{\omega j}^{(n)}$ and then $\gamma_{\omega j}^{(n)}$ is updated while holding fixed the new value of $f_{\omega\phi l}$; the process is repeated until convergence is acceptable. The information for updating $\gamma_{\omega j}^{(n)}$ must come from equation (4), since equation (5) has already been used, and since, clearly, the information from the scattered field measurements must be incorporated into the process. This process also advantageously gives the solution for the internal field $f_{\omega\phi l}$, even though the ultimate result to be obtained is the scattering potential.

To solve equation (4) for $\gamma_{\omega j}$ at a fixed value of $f_{\omega\phi j}$ and $\omega$, the idea of backprojection is used. In x-ray computed tomography (x-ray CT), the concept of backprojection has been a powerful tool for image reconstruction from projections. Backprojecting x-ray CT data directly produces an image which is a blurred version of the original object. The original object may be recovered by convolving with a deblurring function. The backprojection operation spreads the detector density values along the x-ray paths back to the detector. The sum of this operation for all source positions is the backprojected image.

The concept of backprojection as used in x-ray CT does not translate exactly in the case of finding $\gamma_{\omega j}$ by backprojecting the measured values of $f_{\omega\phi m}^{(sc)}$ from the detector measurement set $\{m, \phi, \omega\}$, since there are no explicit ray paths in equation (4). However, an analogy can be found. Equation (4) is a sum over all scattering points in the body, each of which radiate an outward going spherical wave whose initial modulus and phase at point j are given by the product $e_\omega f_{\omega\phi j}$, and whose complex phase at detector m is given by multiplying this product by the Green's function-like propagation coefficient $D_{\omega mj}$.

Therefore, the step that is analogous to backprojection into a picture element ("pixel") would be to reradiate the detected signal at each detector m with a phase corresponding to the negative of the shift in scattering from pixel l to detector m. Thus, the round trip phase shift from pixel l to detector m and back to pixel l would be zero (for signals received at all m that originated at pixel l), and the sum over all m into l would add constructively. Backprojecting signals from all m into pixel l that did not originate at from pixel l would not result in a zero phase shift and therefore would result in destructive interference. Two formulas that may be used would be to multiply $f_{\omega\phi m}^{(s)}$ by $D_{\omega ml}^*$ (here, the star symbol * indicates taking complex conjugate) and sum over m, $\phi$ and $\omega$, or to divide $f_{\omega\phi m}^{(sc)}$ by $D_{\omega ml}$ and sum over m, $\phi$ and $\omega$. The renormalization of amplitude is different in each case. Either of these formulas still does not complete the analogy of backprojection in a logical sense, since actually the influence of the product $\gamma f_\phi$, not $\gamma$ alone, is backprojected. Thus, for each $\phi$, backprojection, as defined above, produces a blurred image of $\gamma f_\phi$. Also, if $\gamma$ is frequency dependent, which it usually is, then summing over $\omega$ may not produce the best image. Thus, the above general scheme must be modified as, for example, described next.

Backprojection of $\gamma$ can be achieved by dividing the backprojected image of $f_\phi\gamma$ by $f_\phi$ for each $\phi$, and then summing all such modified images over $\phi$. Using the $D_{\omega ml}^*$ form, the backprojection process is summarized by a formula for $\gamma$, here defined to be the backprojected approximation of the scattering potential $\gamma_\omega$, as follows:

$$\bar{\gamma}_{\omega l}^{(k)} = k_{\omega l}\sum_{\phi=1}^{\Phi}(1/f_{\omega\phi l}^{(k)})\sum_{m=1}^{M}D_{\omega ml}^*f_{\omega\phi m}^{(sc)} \stackrel{\Delta}{=} B[f_{\omega\phi m}^{(sc)}] \quad (8a)$$

Here, $k_l$ is a normalizing factor taken to be $2n/\Phi$, and B is the backprojection operator. The sum over m already has a renormalization factor built into the $D^*$, so K does not depend on M. If the frequency dependence of $\gamma$ is of a sufficiently simple and special form, then the spatial resolution of $\gamma$ can be further improved by extending the backprojection operation to include summing over $\omega$. For example, if $\gamma$ is given by equation (2a) and if $\alpha = \alpha_o \omega^{no}$, then $\gamma$, as given by the following formula, will have improved spatial resolution and will still be quantitatively accurate.

$$\tilde{\gamma}_l = \sum_{\omega=1}^{\Omega} Re[\tilde{\gamma}_\omega l] + i \sum_{\omega=1}^{\Omega} \omega^{(1-no)} Im[\tilde{\gamma}_\omega l] \triangleq B[f_{\omega\phi m}^{(sc)}], \quad (8b)$$

Note that equation (8b) is a special case of equation (8a).

The closeness of approximation to $\gamma_\omega$ by $\tilde{\gamma}_\omega$ for single frequency data has been investigated by considering the much simplified problem of a single weak scattering point at $\underline{x}_s$ (so that the Born approximation is valid), with plane wave sources radiating sequentially from all angles and a circular ring detector at a very large radius (where the asymptotic form of Green's function is valid). In this case, for a single frequency, $\tilde{\gamma}_\omega$ obtained from the integral form of equation (8a) may be evaluated analytically and is found to be proportional to $J_o^2(k_o^2|\underline{x}-\underline{x}_s|)$, where $J_o$ is the well-known zero order Bessel function. For the three-dimensional case of a spherical detector of a very large radius, $\tilde{\gamma}_\omega$ is proportional to $\text{sinc}^2(k_o^2|\underline{x}-\underline{x}_s|)$. For larger objects, stronger scattering, or other detector configurations, the blurring in $\tilde{\gamma}_\omega$ will be different from the above examples and not necessarily convolutional. If equation (8b) is applied, then an even sharper point response function is obtained.

The above image of $\gamma^{(k)}$, given by equation (8b), must be deblurred to find $\gamma^{(k)}$ by adding to the correction obtained by operating with previously defined $B[\cdot]$ on the difference of the true scattered field $f_{\omega\phi}^{(sc)}$ and the predicted scattered field $\underline{P}[\gamma^{(k)}]$. Here $$P[\gamma_{\omega\phi j}] = \sum_j D_{\omega m j} f_{\omega\phi j} \gamma_{\omega j}$$

is a "projection" (actually scattering) operator. This deblurring operation may be written for a single frequency $$\gamma_\omega^{(k)(1)} = B[f_{\omega\phi}^{(sc)} - P\gamma_\omega^{(k)(0)}] + \gamma_\omega^{(k)(0)} \quad (9)$$

where $\gamma_\omega^{(k)(0)}$ is defined to be $\gamma_\omega^{(k)}$ from equation (8a). Of course, the operation of deblurring may be repeated and the general iteration formula, using operator notation upon reordering, is $$\gamma^{(k)(n+1)} = Bf_\phi(sc) + [I - BP]\gamma(n) \quad (10)$$

This process converges only if $[I-BP]$ has positive eigenvalues which lie within the unit circle. Another formula which always converges for appropriate $\gamma$, since $(BP)^\dagger BP$ has no negative eigenvalues, is given by $$\gamma^{(k)(n+1)} = K_1(BP)^\dagger Bf_\phi^{(sc)} + [I - K_1(BP)^\dagger BP]\gamma^{(k)(n)} \quad (11)$$

Here, the dagger symbol indicates taking the complex conjugate transpose. Optimum convergence of equation (11) occurs when the underrelaxation parameter $K_1$ is given by $K_1 = 2/(\lambda_{max} + \lambda_{min})$, where $\lambda_{max}$ and $\lambda_{min}$ are the maximum and minimum eigenvalues, respectively, of $(BP)^\dagger BP$. Although equation (11) always converges, it may actually converge more slowly than equation (10) because the eigenvalues of $(BP)^\dagger BP$ are less tightly clustered than those of $BP$. Thus, if $BP$ has no negative eigenvalues, the following formula may converge faster than either of equations (10) or (11):

$$\gamma^{(k)(n+1)} = K_2 B f_\phi^{(sc)} + [I - K_2 BP]\gamma^{(k)(n)} \quad (12)$$

Here, the best value of the underrelaxation parameter $K_2$ is two times the reciprocal of the sum of the largest and smallest eigenvalue of $(BP)$.

The convolution operation $Bf_{\omega\phi}^{(sc)}$ can be done by FFT only if $f_{\omega\phi}^{(sc)}$ is defined on a rectangular grid containing field points or is interpolated onto such a rectangular grid. Even the more complicated equation (11) may be computed by FFT by noting that $(BP)^\dagger = P^\dagger B^\dagger$ and performing the $B^\dagger$ and $P^\dagger$ convolutions sequentially.

Insofar as the possibility of $f_{\omega\phi}^{(k)}$ vanishing at some pixel $\underline{x}_l$ is concerned, for medical ultrasound tomography or seismic imaging, by using a small enough value of $\omega$, this is unlikely; but in such cases, a modification of equation (8a) is suggested, which still may be valid:

$$\tilde{\gamma}_{\omega l}^{(k)} = K_l \sum_{\phi=1}^{\Phi} \left( f_{\omega\phi l}^{(k)*} / \sum_{\theta=1}^{\Phi} f_{\omega\phi}^{(k)} \right) \sum_{m=1}^{M} D_{\omega m l}^* f_{\omega\phi m}^{(sc)} \quad (13)$$

$$\triangleq B[f_{\omega\phi m}^{(sc)}]$$

It is instructive to insert the scattered field from a single scattering point, $f_{\omega\phi m}^{(sc)} = \sum_j \delta_{sj} f_{\omega\phi j} D_{\omega m j}$ into either equation (8) or equation (13) and verify that a sharply peaked distribution of $\gamma$ values occurs around pixel $s$ (here, $\delta_{sj} = 1$ for $s=j$ and 0 for $s \ne j$). Equation 13 suggests setting $K_l = \sum_m D_{\omega m l}^* D_{\omega m l}$. In practice, any $K_l$ is made workable by the correct choice of $K_1$ or $K_2$ in equation (11) or equation (12).

The foregoing description is based on the use of the Helmholtz wave equation (1a) to model the scattered acoustic energy propagated through an object. As noted above, the Riccati wave equation (1b) could also be used for purposes of the model. The Helmholtz partial differential equation (1a) may be transformed to the Riccati partial differential equation (1b), as described above. By use of Green's theorem, equation (1b) may be transformed to the following integral equation:

$$w_{\omega\phi}(x) = -k_o^2 \int \gamma_\omega(x') G_{\omega\phi}(x-x') d^Q x' - \int [\nabla w(x')] \cdot \nabla w(x')] G_{\omega\phi}(x-x') d^Q x' \quad (14)$$

For incident plane waves, $e^{ik(\phi) \cdot \underline{x}}$, $G = e^{ik_o(\phi) \cdot (\underline{x} - \underline{x}') \cdot g(\underline{x} - \underline{x}')}$, where $g$ is the same as in equation (3).

By the method of moments, $w_{\omega\phi}$ and $\nabla w_\phi \cdot \nabla w_\phi$ may be expanded in special sinc basis functions $\{\psi_j\}$, and upon substituting the basis expansions of $w_{\omega\phi}$, $\gamma_\omega$, and $\nabla w_{\omega\phi} \cdot \nabla w_{\omega\phi}$ into equation (14), interchanging integration and summation, and evaluating $\underline{x}$ at rectangular node points, the following algebraic equations are obtained, respectively, for points $\underline{x}_m$ on the detector and for points $\underline{x}_m$ in the Q-dimensional support window containing nonzero values of $\gamma_\omega$:

$$W_{\omega\phi m} + \sum_{j=1}^{N} D'_{\omega\phi m j} (\nabla w_{\omega\phi} \cdot \nabla w_{\omega\phi})_j \triangleq W'_{\omega\phi m} = \quad (15)$$

$$-\sum_{j=1}^{N} k_o^2 D'_{\omega\phi m j} \quad \begin{array}{l} m = 1, \ldots, M \\ \phi = -1, \ldots, \Phi \end{array}$$

$$W_{\omega\phi l} = -k_o^2 \sum_{j=1}^{N} D'_{\omega\phi l j} \gamma_{\omega j} - \quad (16)$$

$$\sum_{j=1}^{N} D'_{\omega\phi l j} (\nabla w_{\omega\phi} \cdot \nabla w_{\omega\phi})_j \quad \begin{array}{l} l = 1, \ldots, N \\ \phi = 1, \ldots, \Phi \end{array}$$

The constants $D_{\omega\phi mj}'$ and $D_{\omega\phi lj}'$ in equations (15) and (16) are obtained from $$D_{\omega\phi\mu j}' = \int \psi_j(x') G_{\omega\phi}(x_\mu - x') d^Q x' \qquad (17)$$

Here, $W_{\omega\phi m}$ is defined to be the measured value of $w_{\omega\phi m}$ at detector point $x_m$. Also, here $\gamma_{\omega j}$, $w_{\omega\phi j}$, and $(\nabla w_{\omega\phi} \cdot \nabla w_{\omega\phi})_j$ are the respective values of $\gamma_\omega$, $w_{\omega\phi}$, and $\nabla w_{\omega\phi} \cdot \nabla w_{\omega\phi}$ at point $x_j$. Equations (15) and (16) are the detector and field equations analogous, respectively, to equations (4) and (5). Inspection of equations (15-17) and the definition of $G_{\omega\phi}$ show that the sums in equations (15) and (16) are convolutions and can thus be done using an FFT operation.

Having described one example which illustrates two alternative mathematical or physical models which may be used to model scattered acoustic energy and to process data so as to reconstruct an acoustic image using inverse scattering theory, reference is next made to FIGS. 6A-6F which schematically illustrates a flow diagram for programming the CPU 118 and array processor 120 or parallel processor 146 in order to enable CPU 118 or said combination to control the electronic system of FIGS. 4 or 5 and the apparatus of FIGS. 1-3 in accordance with one presently preferred method of the invention. It should also be understood that special purpose computational hardware should be constructed to incorporate the flow diagrams of FIGS. 6A-6F. The flow diagrams of FIGS. 6A-6F are merely illustrative of one presently preferred method for programming CPU 118 using the Helmholtz wave equation for modeling scattered acoustic energy, as described above in Example 1. Any suitable computer language which is compatible with the type of CPU 118 that is used in the electronic system can be used to implement the program illustrated in the diagrams.

Figure 6A:
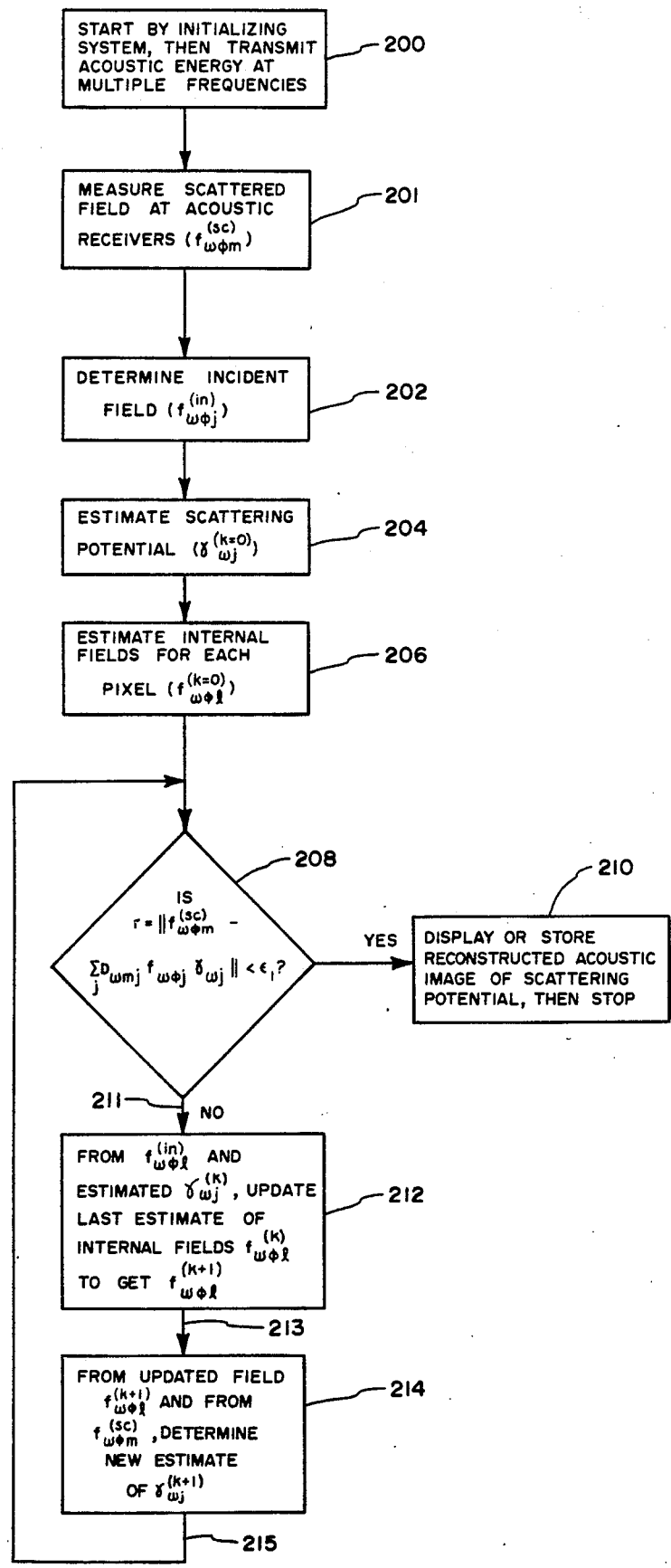

As shown in FIG. 6A, CPU 118 is programmed so that it will first cause the transmitter multiplexer 132 (see FIGS. 4A and 5A) to sequence in turn each acoustic transducer 100-107 (FIGS. 2-3) so that each transmitter will in turn propagate a signal at a selected frequency. In the case of FIG. 4A, for each transmitter position, sequential multiple frequencies may be transmitted by changing the frequency of oscillator 128, whereas in the system of FIG. 5A multiple frequency signals are transmitted by selecting and generating a type of waveform which inherently includes multiple frequencies.

As schematically illustrated in step 201, for each transmitter from which a signal is sent, CPU 118 next causes a receiver multiplexer 134 to sequence each receiver array 108-115 so as to detect the scattered acoustic energy at each position around the ring of transducers 70. The receiver arrays 108-115 detect scattered acoustic energy for each frequency that is transmitted. As described previously, the electronic system then amplifies the detected signals and processes the signals in order to develop the electronic analog of the real and imaginary mathematical components of each signal and in order to digitize each detected signal.

Once the scattered acoustic energy has been detected, processed, and digitized, CPU 118 next determines the incident field $f_{\omega\phi}^{(in)}$, as indicated at step 202. The incident field is determined from the acoustic energy (i.e., frequency and amplitude components of the transmitted wave form) and transducer geometry from which the incident field is transmitted. CPU 118 then estimates the scattering potential $\gamma_{\omega j}^{(k=0)}$ and and the internal fields $f_{\omega\phi}^{(k=0)}$ for each picture element, as indicated at steps 204 and 206. The initial estimate for the scattering potential can be set at either 0 or at an average value which is derived from the average density, acoustic absorption, and speed of sound estimated for the object. When applicable, a lower resolution image of $\gamma$, such as produced by a more approximate method such as the time-of-flight method described in U.S. Pat. No. 4,105,018 (Johnson) may also be used to advantage to help minimize the number of iterations. The initial estimate of the internal fields $f_{\omega\phi}$ may be determined by using the initial estimate of the scattering potential, or the incident field can be used as the initial estimate for the internal fields.

CPU 118 next determines in step 208 whether the norm of the difference between (a), the scattered field $f_{\omega\phi m}^{(sc)}$ as detected and measured at the acoustic receivers, and (b), the predicted scattered field $\Sigma_j D_{\omega mj} f_{\omega\phi j} \gamma_{\omega j}$ as determined by CPU 118 using the estimated scattering potential and estimated internal fields, is less than a selected error value $\epsilon_1$. The difference, or, as it is sometimes called, the residual error or simply the residual r, is given by the equation $$r_{\omega\phi m}^{(sc)} = f_{\omega\phi m}^{(sc)} - \sum_{j=1}^{N} D_{\omega mj} f_{\omega\phi j} \gamma_{\omega j} \qquad (18)$$

Each residual has the physical interpretation of the error in satisfying a physical model equation due to a departure in the trial solution from the exact solution. In the usual case, the internal fields as estimated will not be accurate and the process may proceed from step 208 to step 212. The two norm or total root mean squared (rms) residual error is defined as the square root of the sum over all detector signals at all frequencies and for all source positions, and is given by $$r^{(sc)} = \left( \sum_\omega \sum_\phi \sum_m |r_{\omega\phi m}^{(sc)}|^2 \right)^{\frac{1}{2}} \qquad (19)$$

where $\omega$ corresponds to frequency, $\phi$ corresponds to source positions, and m to detector positions.

If the total root mean squared residual error or two norm of the difference between the measured scattered field and the predicted scattered field is less than the selected error value $\epsilon_1$, CPU 118 uses the scattering potential $\gamma$ to reconstruct and they display or store the acoustic image, as schematically represented at step 210. The acoustic image will include information showing not only the spatial resolution of the object in terms of size and shape, but also showing the internal material properties of density, speed of sound, and acoustic absorption at each scattering point within the object.

If the norm of the difference determined at step 208 is not less than the selected error value, the next step implemented by CPU 118 is to use either the array processor 120 (FIG. 4A) or the parallel processor 146 (FIG. 5A), depending upon which electronic system is used, to prepare a new estimate of the internal fields $f_{\omega\phi}^{(k+1)}$ using the last estimate of the scattering potential $\gamma_{\omega j}^{(k)}$ and the incident field $f_{\omega\phi}^{(in)}$, as represented at step 212. Alternately, step 208 can terminate and pass control to step 210 after a maximum $k_{max}$ number of iterations. For the case where the Helmholtz wave equation (1) is used as the model for representing the scattered acoustic energy, the updated or next estimate for the internal fields $f_{\omega\phi j}^{(k+1)}$, as determined in step 212, is derived from equation (7), which may be implemented by CPU 118, as illustrated in more detail in FIGS. 6B-6C.

Figure 6B:
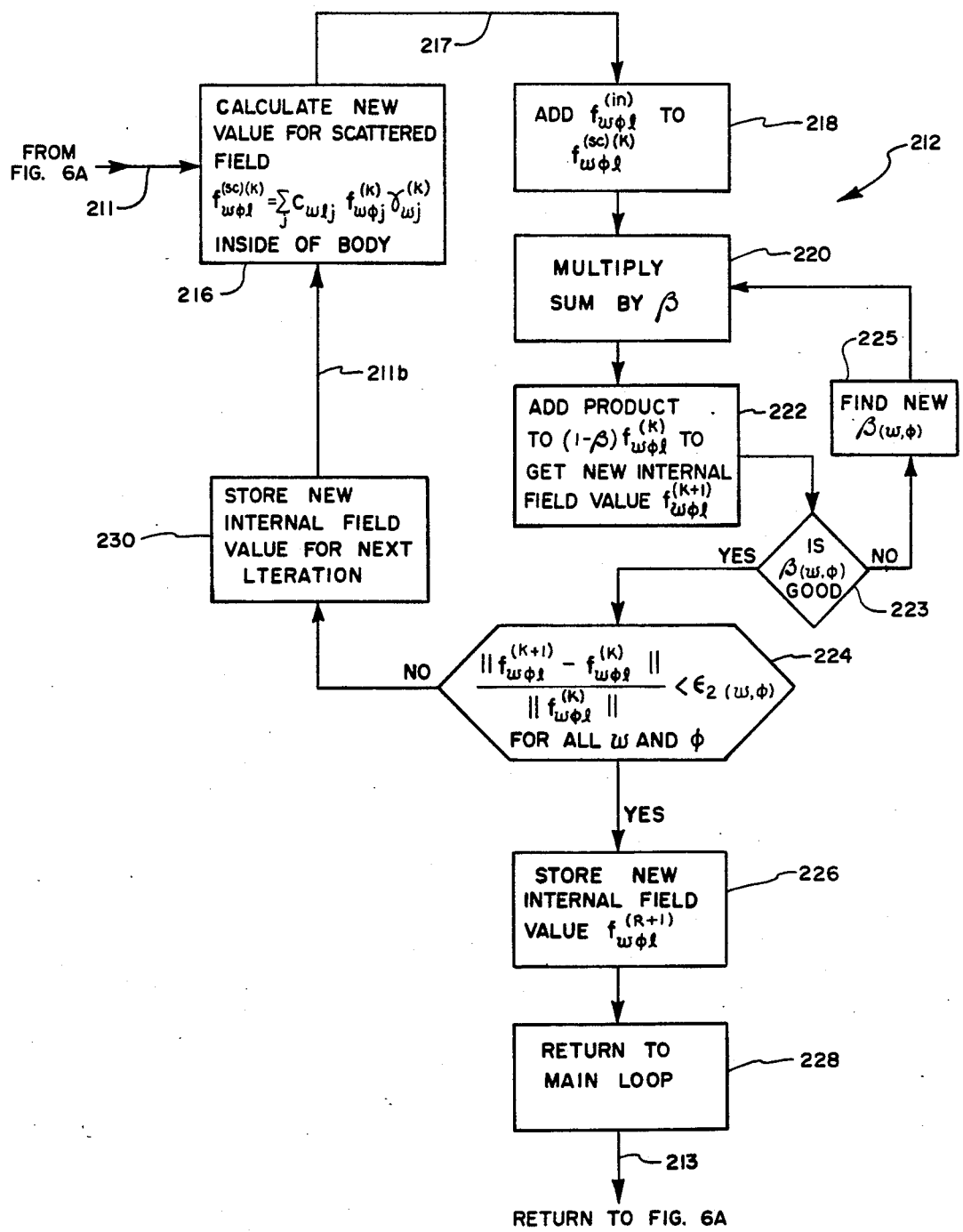

As shown in FIG. 6B, step 212 comprises a series of steps in which CPU 118 first determines a new value for the predicted scattered field by taking the product of the last estimate of the scattering potential $\gamma_{\omega j}^{(k)}$ and the last estimate of the internal field $f_{\omega\phi j}^{(k)}$ and multiplying them by a constant $C_{\omega l j}$, which is determined from equation (6). The resulting product is determined and summed over each scattering point 1 through n in the object, as indicated at step 216.

FIG. 6C illustrates in greater detail the method used to implement step 216, which includes retrieval of the complex fast Fourier transform of the constant $C_{\omega l j}$ that is derived from equation (6), as indicated at step 232, which is then followed at step 234 by taking the complex fast Fourier transform of the product of the last estimate of the internal field $f_{\omega\phi j}^{(k)}$ and the last estimate of the scattering potential $\gamma_{\omega j}^{(k)}$ at each point in the object. At step 236, CPU 118 determines the product of the fast Fourier transforms derived in steps 232 and 234, which is then followed by taking the inverse fast Fourier transform (step 238) to obtain the new value for the scattered field $f_{\omega\phi j}^{(sc)(k)}$. CPU 118 then returns as indicated at step 240 so as to return to the subprogram shown in FIG. 6B, as schematically indicated at the arrow 217.

After the new value for the predicted scattered field $f_{\omega\phi j}^{(sc)(k)}$ has been determined as described in FIG. 6C, it is added to the incident field $f_{\omega\phi j}^{(in)}$, as indicated at step 218. CPU 118 then multiplies the sum determined at step 218 by another constant $\beta$, and then adds the product determined in step 220 to the product of the last estimate of the internal field multiplied by 1 minus the constant $\beta$, which results in the new or updated internal field value $f_{\omega\phi j}^{(k+1)}$, as represented at step 222. As mentioned above, $\beta=1$ will work for most cases of medical ultrasound; however, other applications may require testing $\beta$ to find a value which will result in convergence. Several techniques for optimizing $\beta$ are known, one such technique being the golden section search method. As shown in FIG. 6B at step 223, $\beta$ may be tested to see if it results in convergence by examining the results of step 224; if not, a new value of $\beta$ is selected at step 225 according to the above-described or other known search methods, and the steps leading to step 224 are repeated. The golden section search method constructs a sequence of search intervals that shrink to limiting value that is contained in each search interval. The well known line search method using quadratic interpolation for finding a minima may also be used.

In step 224, CPU 118 determines whether the norm of the difference between the updated internal field $f_{\omega\phi j}^{(k+1)}$ and the last estimate of the internal field $f_{\omega\phi j}^{(k)}$ divided by the norm of this last value of the internal field is less than a selected error value $\epsilon_2$. If the quotient determined in step 224 is less than the selected error value, CPU 118 moves to steps 226 and 228 and stores the new internal field values $f_{\omega\phi j}^{(k+1)}$ and then returns to the main program, as represented at arrow 213. If the quotient determined in step 224 is not less than the selected error value, the new internal field value is stored for the next iteration, and the subroutine of FIG. 6B is then repeated until the quotient becomes less than the selected error value. The field determination, as illustrated in FIGS. 6B and 6C, must be done for each separate pair of $\omega$ (frequency) and $\phi$ (source position) values. Here the use of parallel or special processors could be implemented and would greatly enhance computational speed.

Upon returning to the main program of FIG. 6A, CPU 118 moves to step 214. From the updated internal field $f_{\omega\phi j}^{(k+1)}$ and from the measured scattered field $f_{\omega\phi m}^{(sc)}$, as detected at the acoustic receivers, CPU 118 next determines a new estimate $\gamma_{\omega j}^{(k+1)}$ for the scattering potential.

As illustrated in FIG. 6D, determination of the new estimate for the scattering potential is accomplished in essentially two steps, which are schematically represented at 242 and 244. In step 242, using the measured scattered field $f_{\omega\phi m}^{(sc)}$ CPU 118 backprojects to obtain an approximation $\gamma_j^{(k+1)}$ of the updated scattering potential. CPU 118 then deblurs the approximation so as to obtain the new estimate $\gamma_j^{(k+1)}$ of the scattering potential. The two basic steps 242 and 244 are each illustrated in greater detail in FIGS. 6E and 6F, respectively. In describing the backprojection method in step 242, equation pairs (8a) and (8b) are implemented in FIG. 6E. It should be appreciated that equation pairs (11) and (8b) or equation pairs (13) and (8b) could also be implemented.

Referring first to FIG. 6E, a detailed explanation of the backprojection step 242 of FIG. 6D is given. As schematically indicated at starting step 246, CPU 118 takes the measured scattered field output from step 212 (FIG. 6A) and pads each pixel on the border of the measured scattered field so as to place zeros everywhere except for the detector positions M. CPU 118 then performs a complex fast Fourier transform of the bordered input, as shown at step 248, and then retrieves the complex conjugate of the constant $D_{\omega l j}$ defined by equation (6) above. CPU 118 then moves to step 252 and takes the fast Fourier transform of the complex conjugate and multiplies it by the fast Fourier transform of the measured scattered field, as determined previously in step 248. The CPU 118 takes the inverse fast Fourier transform of the resulting product (step 256), then for each source position $\phi$, the measured scattered field for each point is divided (step 257) by the product of the internal field and a normalizing constant derived by multiplying a constant $k_1$ by the number of detector positions M and the number of source positions $\phi$. $K_1$ may be optimized similar to $\beta$ described in FIG. 6B. The result is summed over each source position to obtain the backprojected estimate of the scattering potential $\gamma_{\omega j}^{(k+1)}$, as indicated at step 258. The CPU 118 then separates $\gamma_{\omega j}^{(k+1)}$ into real and imaginary parts in step 259 in preparation to applying backprojection equation (8b). Next, CPU 118 completes the backprojection by taking a weighted sum over $\omega$, as per equation (8b). This is done in step 260, setting the real part of $\gamma_j^{(k+1)}$ equal to the sum over $\omega$ of the real part of $\gamma_{\omega j}^{(k+1)}$. Also in step 260, the imaginary part of $\gamma_j^{(k+1)}$ is computed by summing over $\omega$ the product of $\omega$ raised to the $(1-n_o)$ power and the imaginary part of $\gamma_{\omega j}^{(k+1)}$. Finally in step 260, the real and imaginary parts of the complex scattering potential estimate $\gamma_j^{(k+1)}$ are combined into a complex vector that is output, as schematically indicated at the arrow 243. CPU 118 then moves to the deblurring process (step 244 of FIG. 6D).

Figure 6F:
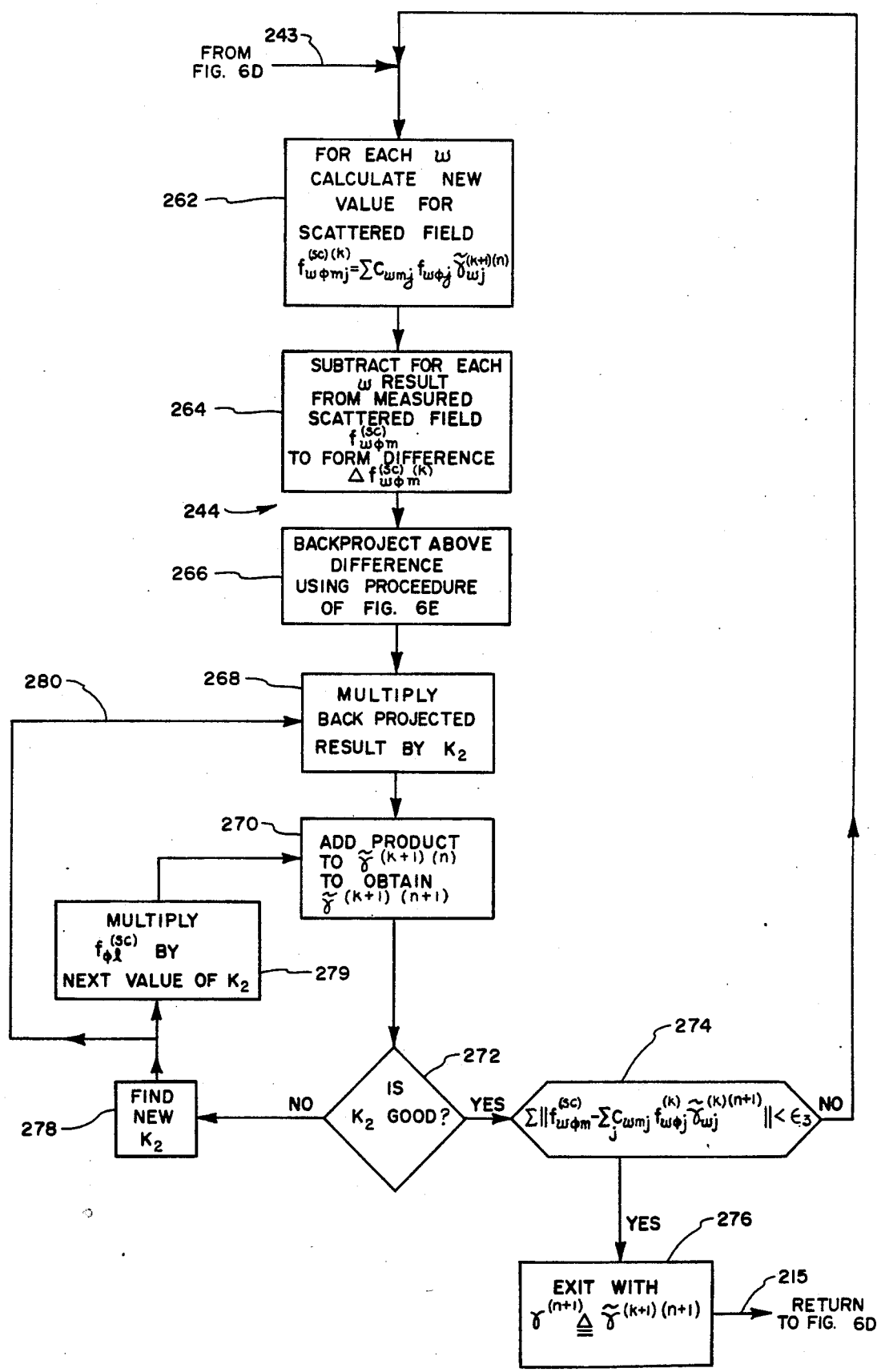

FIG. 6F shows the steps that comprise step 244 of FIG. 6D for deblurring the backprojected estimate of the scattering potential. With reference to FIG. 6F, the backprojected estimate $\gamma_j^{(k+1)}$ for the scattering potential is input, as schematically indicated at arrow 243, and CPU 118 then determines the new value for the predicted scattered field $P_\gamma^{(k+1)(in)}$ by taking the summation over each scattering point j in the object, of the product derived from multiplying the previous estimate $\gamma_j^{(k)(n)}$ of the scattering potential times the internal field $f_{\omega\phi j}$ at the scattering point times the constant $C_{\omega lj}$ at that point. This operation is performed for each frequency $\omega$.

Once the new value for the predicted scattered field is determined from step 262, CPU 118 then subtracts (step 264) the new predicted value from the scattered field measured at the detectors. The difference is then backprojected, as represented at step 266, using the same steps previously illustrated and described in FIG. 6E. The backprojected result is then multiplied by a constant $K_2$ as indicated at step 268 and the resulting product is then added to the backprojected estimate $\gamma^{(k+1)(n)}$ for the updated scattering potential, as indicated at step 270. The CPU 118 then determines at step 272 whether the multiplication constant $K_2$ used in step 268 was appropriate, and if not a new constant is selected at step 278 and the backprojected difference is then multiplied by the new constant, as indicated at step 279, before repeating again steps 268, 270, and 272. The optimum value for $K_2$ is estimated by a search for that value which minimizes the norm of the difference between $f^{(sc)}$ and the predicted scattered field $P[\gamma^{(k+1)}]$ similar to the search method for $\beta$ described above in connection with FIG. 6B. If the multiplication constant is valid, CPU 118 then checks at step 274 to determine whether the norm of the difference between the scattered field measured at the detectors and the predicted scattered field derived by using the updated value of the scattering potential is less than a selected error value $\epsilon_3$. If so, CPU 118 returns to the main program, as schematically indicated at step 276 and line 215, and CPU 118 then repeats steps 208 to determine whether the reconstructed image is ready to be displayed.

EXAMPLE 2

Image Reconstruction for the Case of a General Scattering Potential with Density Dependence from Multiple Frequency Data The inverse scattering technique described in Example 1 may be generalized to reconstruct a scattering potential that includes terms in density, polynomial frequency dependent absorption, and speed of sound. The scattering potential is generalized by adding a density dependent scattering term, and is represented by the following expression:

$$\gamma_\omega(\underline{x}) = 1 - \frac{c_o^2}{c^2(\underline{x})} + \frac{c_o^2}{\omega^2} \rho^{\frac{1}{2}}(\underline{x})\nabla^2 \rho^{-\frac{1}{2}}(\underline{x}) + i2\frac{c_o^2}{\omega c(\underline{x})} \alpha(\underline{x}) \quad (20)$$

This equation can be further generalized to fit almost any material absorption properties by expanding $\alpha(\underline{x})$ as a polynomial $$\alpha(x) = \alpha_o(x) + \omega\alpha_1(x) + \omega^2\alpha_2(x) + \ldots + \omega^n\alpha_n(x), \quad (21)$$

On substitution of equation (21) into equation (20), the scattering potential becomes, when using only the first three terms of equation (21), $$\gamma_\omega(\underline{x}) = 1 - \frac{c_o^2}{c^2(\underline{x})} + \frac{c_o^2}{\omega^2} \rho^{\frac{1}{2}}(\underline{x})\nabla^2 \rho^{-\frac{1}{2}}(\underline{x}) + i2\frac{c_o^2}{c(\underline{x})}\left[\frac{\alpha_o(\underline{x})}{\omega} + \alpha_1(\underline{x}) + \omega\alpha_2(\underline{x})\right] \quad (22)$$

For many materials, $\alpha_o = \alpha_2 \approx 0$ and only the $\alpha_1$ term is necessary. In other materials, use of all terms will increase the accuracy of representation.

The scattering potential, as written in equation (22) above, is frequency dependent. This can be made more clear by writing $\gamma_\omega(\underline{x})$ in the following form:

$$\gamma_\omega(x) = \Gamma_o(x) + \omega^{-2}\Gamma_1(x) + i(\omega^{-1}\Gamma_2(x) + \Gamma_3(x) + \omega\Gamma_4(x)) \quad (23a)$$

or equivalently as the inner product of two vectors:

$$\gamma_\omega(x) = [1, \omega^{-2}, i\omega^{-1}, i, i\omega]\Gamma(x) \quad (23b)$$

where $i = \sqrt{-1}$ and where $r(\underline{x})$ is the column vector given by $$\Gamma = [\Gamma_o, \Gamma_1, \Gamma_2, \Gamma_3, \Gamma_4]^T \quad (24)$$

Here, $[\cdot]^T$ means transpose of row vector $[\cdot]$. Then, the components of $\Gamma$ are given by $$\Gamma_0 = [1 = c_o^2/c^2(x)], \quad (25a)$$

$$\Gamma_1 = c_o^2 \rho^{\frac{1}{2}}(x)\nabla^2 \rho^{-\frac{1}{2}}(x), \quad (25b)$$

$$\Gamma_2 = 2c_o^2\alpha_o(x)/c(x) \quad (25c)$$

$$\Gamma_3 = 2c_o^2\alpha_1(x)/c(x) \quad (25d)$$

$$\Gamma_4 = 2c_o^2\alpha_2(x)\alpha_2(x)/c(x). \quad (25e)$$

It follows that if $\gamma_\omega$ is evaluated at two frequencies, then $\Gamma_0$ and $\Gamma_1$ can be determined. Furthermore, if $\gamma_\omega$ is evaluated at five frequencies, then $\Gamma_0$, $\Gamma_1$, $\Gamma_2$, $\Gamma_3$, and $\Gamma_4$ can be evaluated. If given the set $\Gamma = \{\Gamma_0, \Gamma_1, \Gamma_2, \Gamma_3, \Gamma_4\}$ of frequency independent functions, then the more familiar material properties $\{c, \rho, \alpha_o, \alpha_1, \alpha_2\}$ can be obtained by the following formulas by equating terms of the same power of $\omega$ in equations (22) and (23). Therefore, $c(\underline{x})$ is given by $$c(x) = c_o[1 = \Gamma_o(x)]^{-1}, \quad (26)$$

$\rho(x)$ is the solution of the boundary value problem $$\begin{cases} [\nabla^2 - c_o^{-2}\Gamma_1(\underline{x})]\rho^{-\frac{1}{2}}(\underline{x}) = 0 \\ \rho(\underline{x}) = \rho_B(\underline{x}) \text{ on the boundary} \end{cases}, \quad (27)$$

and $\alpha_0$, $\alpha_1$, and $\alpha_2$ are given, respectively, by $$\alpha_o(x) = c(x)\Gamma_2(x)/(2c_o), \quad (28)$$

$$\alpha_1(x) = c(x)\Gamma_3(x)/(2c_o), \quad (29)$$

$$\alpha_2(x) = c(x)\Gamma_4(x)/(2c_o). \quad (30)$$

It is clear that more terms in the absorption polynomial could be used if higher accuracy is required. Furthermore, the solution $\rho(\underline{x})$ of the boundary value problem given by equation (27) is possible with existing, well-known methods. One well-known method is that of discretizing equation (27) to obtain a system of linear equations that may be solved for $\rho(\underline{x})$. A particular form of this approach that is especially fast is described later in this section in Example 3. Since solving for $\rho(\underline{x})$ by the preceding method requires $\Gamma_1(\underline{x})$, it is necessary to first derive a technique to find $[\Gamma_0, \Gamma_1, \Gamma_2, \Gamma_3, \Gamma_4]$.

In practice, the use of only five frequenices may not produce useful images because of the ill-conditioning of a particular problem. For example, if the sources and receivers can only be placed on one side of a body, e.g., a square body, then only ¼ as many receivers and ¼ as many transmitters can be used, as in the case where the transducer surrounds the body. Thus, at least $(4)^2 = 16$ times more data must be collected in the former case than for the case of the transducer surrounding the body. In practice, the image quality improves as the number of separate frequencies is increased.

The need for data at many frequencies requires that the scattering potential coefficients $\Gamma = [\Gamma_0, \Gamma_1, \Gamma_2, \Gamma_3, \Gamma_4]$ be chosen so that the frequency dependent scattering potential $\gamma_\omega(\underline{x})$ satisfies equations (4) and (5) at all frequencies. This requires least-squares fit of the vector $\Gamma$ to the backprojected and deblurred values of $\gamma_\omega^{(k+1)}$, as given by equations (11) or (12) and as illustrated as output 215 in FIGS. 6D and 6F. The least-squares fit is conveniently obtained by use of the conjugate gradient method because of its speed of convergence and stability, even with noise-contaminated data.

The least-squares problem is formulated as follows: Let $\gamma_\omega^{(k+1)}(\underline{x})$ be the $(k+1)$ trial fit of $\gamma_\omega$ at each frequency $\omega$ obtained by backprojection and deblurring using the methods described in Example 1. In particular, equations (8) or (13) for backprojection and equations (10), (11), or (12) for deblurring may be used. Let $\gamma_\omega^{(k)(n+1)}$ be the result of these operations. A method for obtaining $\Gamma$ from the set $\{\Gamma_\omega^{(k)(n+1)}\}$ is described next.

Considering equation (23b), it is clear that for each $\underline{x}$ and for each $\omega$, equation (23b) is one equation of a larger linear system of equations that may be written as for the h-th value of $\omega$, i.e., $\omega_h$, as $$\gamma_{\omega h}^{(k)(n+1)}(\underline{x}) = \sum_{j=1}^{4} M_{hj}\Gamma_j^{(k)(n+1)}(\underline{x}), \quad h = 1, 2, \ldots, H \tag{31a}$$

or in matrix notation $$\gamma^{(k)} = M\Gamma^{(k)} \tag{31b}$$

The matrix M is defined as follows: for each j, $M_{hj}$ is an element of the row vector $[1, \omega_h^{-2}, i\omega_h^{-1}, i, i\omega_h]$. Since, in general, the number of frequencies H may be greater than five, equation (31) is overdetermined, although each $\gamma_{\omega h}^{(k)(n+1)}$ may be a blurred version of the true $\gamma_{\omega h}$. Thus, the $\Gamma^{(k)(n+1)}$ that best solves equation (31) may be chosen to be the least-squares solution of equation (31). Since the iteration index $(n+1)$ refers to the deblurring step only, it is omitted in equation (31b). If equation (31) is multiplied by $M$, the result is $$M\,M\Gamma^{(k)} = M\,\gamma^{(k)} \tag{31c}$$

The system of equations $(M\,M)\Gamma^{(k)} = (M\,)\gamma^{(k)}$ is at most of rank 5, since $(M\,M)$ is a 5 by 5 matrix. Thus, efficient iterative methods should solve equation (31) in, at most, 5 steps, since equations (31a), (31b), and (31c) are equivalent.

Many methods for finding the least-squares solution of equation (31) are known and a particularly fast method that converges in 5 or less steps is described below.

Least-squares problems may be solved very conveniently by application of the conjugate gradient (c.g.) method. The c.g. method has many advantages over other methods for solving systems of linear equations such as:

1. It converges in a finite number $m \leq n_{rank}$ of steps to the least-squares solution of a rank $n_{rank}$ nonsingular system.
2. The rate of convergence is so rapid that often $m << n_{rank}$ steps lead to a sufficiently accurate results.
3. No matrix inversion is explicitly performed and no inverse matrix is computed stored.
4. The method works well even for ill-conditioned systems of equations.

Convergence in $m << n$ steps occurs when the eigenvalues are distributed in m or fewer tight clusters.

Although many variations of the c.g. method exist, the following version is preferred because of its relative simplicity and its ability to reduce simultaneously both the squared total residual (a measure of range error) and the squared solution error (a measure of domain error) at each iterative step. Given a system of linear equations $Az = y$, the least-squares solution x may be found by forming a new system of equations:

$$(A\,A)z = (A\,y) \tag{32}$$

The new system of equations (32) has the advantage of having a matrix $(A\,A)$, which is Hermitian and square (a matrix M is Hermitian if $M = M$).

For real systems $Ax = y$, the system (32) can be solved without explicitly computing the matrix $(A\,A)$. This method also applies to complex systems $Az = y$. If the number of measurements y exceed the number of unknown z, then the matrix A is rectangular, but $(A\,A)$ is still square with the dimension on a side equal to that of column vector $\underline{z}$. Thus, rectangular overdetermined systems can also be solved by the c.g. method.

Let a range error function $E_R(\underline{z})$ and domain error function $E_D(\underline{z})$ be defined in terms of the residual vector $r = y - Az$, and the solution error vector $\Delta z = z_{soltn} - z$ by the formulas:

$$E_R(z) = r\,r = (y - Az)\,(y - Az), \tag{33a}$$

$$E_D(z) = (z_{soltn} - z)\,(z_{soltn} - z). \tag{33b}$$

$E_R$ and $E_D$ approach zero as $\underline{z}$ approaches the solution $z_{soltn}$ or approaches a global minimum as $\underline{z}$ approaches the least-squares solution $z_{lss}$.

The c.g. method reduces both range and domain error functions in each iterative step. The c.g. method uses the concept of an inner product. The inner product $<u, v<$ of two vectors $u = [u_1, u_2, \ldots], v = [v_1, v_2, \ldots]$ is defined by $$<u, v> = u_1v_1^* + u_2v_2^* + \cdots \tag{34}$$

The complete c.g. method comprises the following steps:

1. Set up the initial conditions. Choose $z^{(0)}$, the starting guess for $\underline{z}$. Choose the stopping criteria $\epsilon$, or alternately, $\epsilon_2$. Set $$r^{(0)} = y - Az^{(0)}, \; s^{(-1)} = 0, \; q^{(-1)} = 0, \; d^{(-1)} = 1. \qquad (35a-35d)$$

Set $$n = 0. \qquad (35e)$$

2. The next series of steps comprises one iteration of the c.g. method. Compute $$g^{(n)} = A + r^{(n)}. \qquad (36a)$$

3. Compute $$h^{(n)} = Ag^{(n)}. \qquad (36b)$$

4. Compute $$e^{(n-1)} = <q^{(n-1)}, h^{(n)}>. \qquad (36c)$$

5. Compute $$b^{(n-1)} = e^{(n-1)}/d^{(n-1)}. \qquad (36d)$$

6. Compute $$s^{(n)} = g^{(n)} + b^{(n-1)}s^{(n-1)}. \qquad (36e)$$

7. Compute $$q^{(n)} = h^{(n)} + b^{(n-1)}q^{(n-1)}. \qquad (36f)$$

8. Compute $$d^{(n)} = |q^{(n)}|^2. \qquad (36g)$$

9. Compute $$c^{(n)} = <\underline{q}^{(n)}, r^{(n)}> \text{ or } c^{(n)} = <g^{(n)}, s^{(n)}>. \qquad (36h)$$

10. Compute $$a^{(n)} = c^{(n)}/d^{(n)}. \qquad (36i)$$

11. Update solution by the step, $$z^{(n+1)} = z^{(n)} + a^{(n)}s^{(n)}. \qquad (36j)$$

12. Compute $$r^{(n+1)} = r^{(n)} - a^{(n)}q^{(n)}. \qquad (36k)$$

(Alternately, the equivalent but more time-consuming step $r^{(n+1)} = y - Az^{(n+1)}$ could be used.)

13. Test for convergence by use of one or more of the following appropriate tests:

a.

If $\|r^{(n+1)}\| < \epsilon_1$, go to step 14, else go to step 2. (36l)

b. An alternate test for convergence is:

If $\|r^{(n+1)} - r^{(n)}\| / \|r^{(n)}\| < \epsilon_2$, go to step 14, else go to step 2. (36m)

c. A further alternate test for convergence is to count the number of iterations n and compare to some upper bound $n_{stop} \leq n_{max}$.

If $n > n_{stop}$, then go to step 14, else go to step 2. (36n)

14. Exit c.g. method.

The vector g behaves like a gradient because, at any point, $z$ the vector $\underline{g}(\underline{z})$ is the steepest descent direction of the error function $\bar{E}(\underline{z})$ and the modulus of g is proportional to the slope of descent. Two vectors $\underline{u}$ and $\underline{v}$ are said to be conjugate with respect to A if the inner product of $\underline{u}$ and $A\underline{v}$ is zero, i.e., $<u, Av> = 0$. The descent correction vectors $s^{(n)}$ and $s^{(j)}$ can be shown to be conjugate if $n < j$. Since $s^{(n)}$ is obtained from gradient vector $g^{(n)}$ by equation (36e), the phrase "conjugate directions from gradients" has been shortened to the now well-known name "conjugate gradient." Also note that $q^{(n)} = Ap^{(n)}$ is an alternate form for determining $q^{(n)}$.

Although $\Gamma_1(\underline{x})$ may be obtained by solving equation (23) for $\Gamma(\underline{x})$, the function $\Gamma_1(\underline{x})$ is proportional to $\rho^{\frac{1}{2}}(\underline{x})\nabla^2\rho^{-\frac{1}{2}}(\underline{x})$ and thus vanishes where $\nabla^2\rho^{-\frac{1}{2}}(x) = 0$. The Laplacian, $\nabla^2$, of $\rho^{-\frac{1}{2}}$ is zero where the gradient of $\rho^{-\frac{1}{2}}$ is constant or where $\rho^{-\frac{1}{2}}$ is constant. Thus, to obtain $\rho^{-\frac{1}{2}}$, and thus $\rho$, it is necessary to solve the combined partial differential equation with bound any conditions given by equation (27). This is done by discretizing equation (27).

The discretization of equation (27) requires that $\nabla^2\rho^{-\frac{1}{2}}$ be also discretized, and this is conveniently accomplished by noting that the $\nabla^2$ operation is a convolution. Although specific standard forms for $\nabla^2$ are given in numerical analysis texts, more satisfactory results are obtained if a special form is chosen to match the characteristics of the data and the imaging system. This choice is made by noting that $\nabla^2\rho^{-\frac{1}{2}}$ may be computed in the Fourier transform domain. Let $F[\cdot]$ be the Fourier transform operation on $[\cdot]$ and $F^{-1}[\cdot]$ the inverse operation. Then, from the theory of Fourier transforms, it follows that $$\nabla^2\rho^{-\frac{1}{2}}(x) = F^{-1}[-4\pi\Lambda^2 F[\rho^{-\frac{1}{2}}(x)]] \qquad (37)$$

But the spatial frequency vector $\Lambda$ cannot be unbounded because of the requirement that the scattering data cannot sample and recover a spatial frequency in the object greater than the highest spatial frequency in the internal field. Thus, $\Lambda^2$ must be multiplied by a high-frequency cutoff filter (i.e., a lowpass spatial filter) $B(\Lambda)$ to avoid aliasing of spatial frequencies and to avoid computing and storing useless spatial frequency data. Thus, for bandlimited systems, equation (37) should be rewritten as $$\nabla^2\rho^{-\frac{1}{2}}(x) = F^{-1}[-4\pi\Lambda^2 B(\Lambda)F[\rho^{-\frac{1}{2}}(x)]] \qquad (38)$$

By application of the convolution theorem and the Fourier transform properties of $\nabla^2$, this is written as a convolution as $$\nabla^2\rho^{-\frac{1}{2}}(\underline{x}) = F^{-1}[-4\pi\Lambda^2\tilde{B}(\underline{\Lambda})F[\rho^{-\frac{1}{2}}(x)]] = \qquad (39)$$
$$\{\nabla^2 F^{-1}[\tilde{B}(\underline{\Lambda})]\} * \rho^{-\frac{1}{2}}(\underline{x})$$

Here, the symbol $*$ means convolution.

Let $F^{-1}[B(\Lambda)] = B(x)$. Then, $\nabla^2\rho^{-\frac{1}{2}}(x) = (\nabla^2 B(x)) * \rho^{-\frac{1}{2}}(x)$. Then equation (27) becomes $$\begin{cases} (\nabla^2 B(\underline{x})) * \rho^{-\frac{1}{2}}(\underline{x}) - C_o^{-2}\Gamma_1(\underline{x})\rho^{-\frac{1}{2}}(\underline{x}) = 0 & (40a) \\ \rho(\underline{x}) = \rho_B(\underline{x}) \text{ on boundary} & (40b) \end{cases}$$

Let $\delta(\underline{x}, \underline{x}_B)$ be a function that is unity if x is a member of the set of boundary points $\underline{x}_B$ and zero otherwise. Then, $[1-\delta(\underline{x}, \underline{x}_B)]$ is zero for all points $\underline{x}$ on the boundary. Thus, equation (40) may be written $$[\nabla^2 B(x)^* \rho^{-\frac{1}{2}}(x) - C_o^2 \Gamma_1(x)\rho^{-\frac{1}{2}}(x)][1-\delta(x, x_B)] = 0 \quad (41a)$$

$$\rho(x)\delta(x, x_B) = \rho_B(x)\delta(x, x_B) \quad (41b)$$

Upon adding equations (41a) and (41b), a convenient linear system of equations containing the boundary information is obtained:

$$[\nabla^2 B(x)^* \rho^{-\frac{1}{2}}(x) - c_o^{-2}\Gamma_1(x)\rho^{-\frac{1}{2}}(x)][1-\delta(x-x_B)] + \delta(x, x_B)\rho^{-\frac{1}{2}}(x) = \rho_B^{-\frac{1}{2}}(x)\delta(x, x_b) \quad (42)$$

Let the operator $\nabla^2 B(\underline{x}) * [\cdot]$ be replaced with the matrix operator H given by $$[H_{ij}][\rho_j^{-\frac{1}{2}}] = \nabla^2 B(x_j)^* \rho_j^{-\frac{1}{2}} = H_{i-j}\rho_j^{-\frac{1}{2}} \quad (43)$$

Let $\Gamma_1(x_j)=(\Gamma_1)_j$ and let $[1]_k$ be the row vector $[1, 1, 1, \ldots, 1]$, then the diagonal operation $\Gamma_1(\underline{x})\rho^{-\frac{1}{2}}(\underline{x})$ has its equivalent in tensor notation, namely, $(\Gamma_1)_{ik}(\rho^{-\frac{1}{2}})_k$, where $(\Gamma_1)_{ik}$ is given by $$(\Gamma_1)_{ik} = \sum_j \sigma_{ij}(\Gamma_1)_j[1]_k^T. \quad (44)$$

When equations (43) and (44) are combined with equation (42), a simplified linear equation is obtained:

$$\sum_j V_{nj}\rho^{-\frac{1}{2}}(\underline{x}_j) = \delta(\underline{x}_n, \underline{x}_B)\rho^{-\frac{1}{2}}(\underline{x}_n) \quad (45a)$$

where $V_{nj} = V(x_n, x_j)$ is an element of the matrix V and is given by $$V_{nj} = [(H_{n,j} - c_o^{-2}(\Gamma_1)_{n,j})(1-\delta(x_n, x_B)) + \delta_{n,j}\delta(x_n, x_B)]. \quad (45b)$$

Thus, solving the partial differential equation and associated boundary value problem in equation (27) has been reduced to solving the linear system of equations (45).

For the more general case as described above in Example 2, the CPU 118 or combination of CPU 118 and array processor 120 or parallel processor 146 may be programmed as illustrated in the flow charts of FIGS. 7A–7E. Starting at step 200, the operation of CPU 118 is the same as in FIG. 6A, except that the scattered fields in step 201, the incident field in step 202a, the scattering potential in step 204a, and the internal fields in step 206a are obtained at each frequency $\omega$. The residual test in step 208 is done by CPU 118, with the norm summing over $\phi$, m, and $\omega$, as per equations (18) and (19). The estimation of internal fields in step 212a is done by CPU 118 for all $\omega$ using the same approach as described in Example 3. The backprojection and deblurring in step 214a is done by CPU 118 separately at each $\omega$ according to equations (9) through (13), as described in Example 1. The output of step 214a consists of a backprojected and deblurred image $\gamma_\omega$ at each frequency $\omega$. This set of images is then operated upon by CPU 118 in step 304 to produce the vector $\Gamma$ which consists of the set of five separate frequency independent material images $[\Gamma_0, \Gamma_1, \Gamma_2, \Gamma_3, \Gamma_4] = \Gamma$. The vector $\Gamma$ is then used by CPU 118 to determine in step 305 the $\gamma$ image by equation (31b). Thus, vector $\gamma$ consists of an image for each $\omega$, i.e., $\gamma = [\gamma_{\omega 1}, \gamma_{\omega 2}, \ldots]^T$. The vector $\gamma$ is the output that is reintroduced into residual test 208 as represented at line 215a. The test 208a will require further steps 212a, 214a, and 304 until the residual r is less than $\epsilon_1$, or until the iteration index k exceeds some programmable upper limit $k_{max}$. If either test is passed, then test step 208a passes the latest version of vector $\gamma^{(k)}$ to step 300, where images of the material properties $[c, \rho, \alpha_0, \alpha_1, \alpha_2]$ are prepared by CPU 118. The result is passed to step 210a, where the final result is stored or displayed.

Figure 7A:
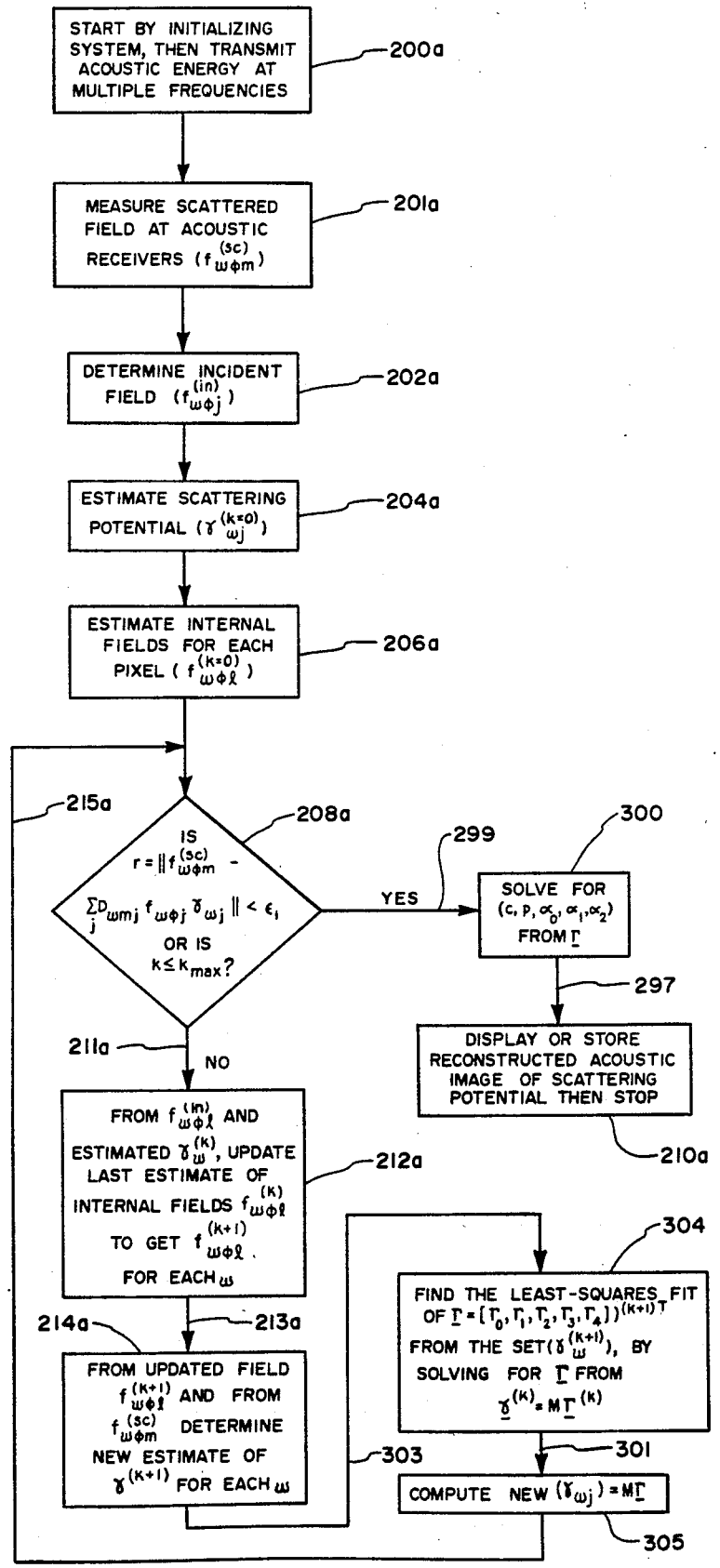
FIGS. 7A-7E schematically illustrate another method by which the electronic systems of FIGS. 4 or 5 may implement inverse scattering techniques to acoustically image an object.
Figure 7B:
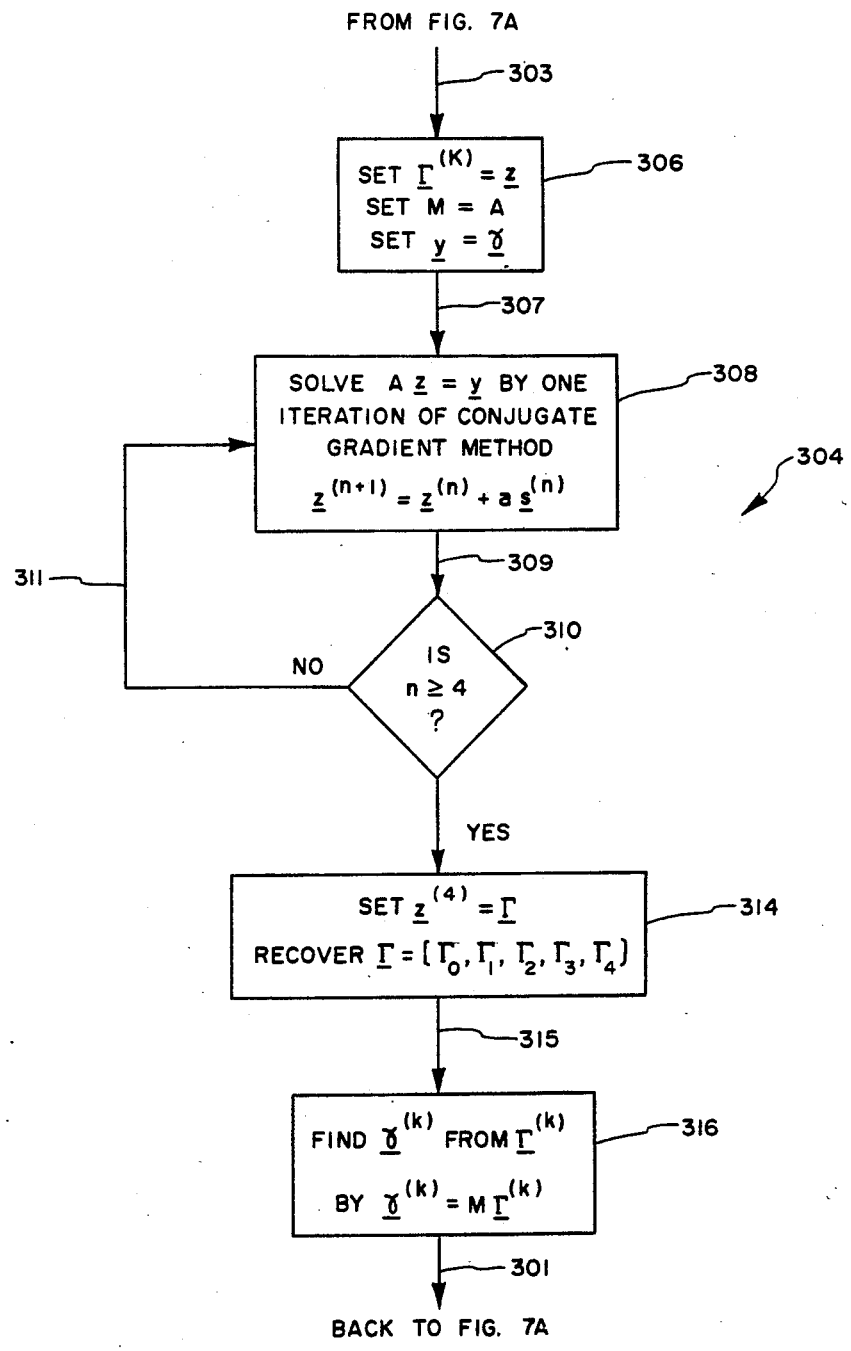

FIG. 7B illustrates in detail the operation performed by CPU 118 in step 304. The input on line 303 consists of the vector $\Gamma^{(k)}$ and the matrix M defined by equation (31). The CPU assigns $\Gamma^{(h)}$, M, and $\gamma$ to general variables z, A, and y, respectively, that are used by the conjugate gradient linear equation used in step 308. The updated value of z, here shown as $\underline{z}^{(n+1)}$, is determined by CPU 118, and the value of n is set to 0 in the first pass through step 308. In test step 310, CPU 118 checks to see if n is greater than or equal to 4. On the fifth pass through (after all 5 components of $\Gamma$ are calculated), this condition is met and the completed value of $\underline{z}^{(4)}$ is available and control passes to step 314. However, at step 310, if n is less than 4, the vector $\underline{z}^{(n+1)}$ is passed back to the c.g. step 308. The final vector $\underline{z}^{(4)}$ is reassigned the name $\Gamma$ in step 314 by CPU 118. The output $\Gamma$ is passed to step 316, where CPU 118 determines the image of the scattering potential at each frequency by use of equation (31). Control then passes back to the main program, as illustrated at line 301.

Figure 7C:
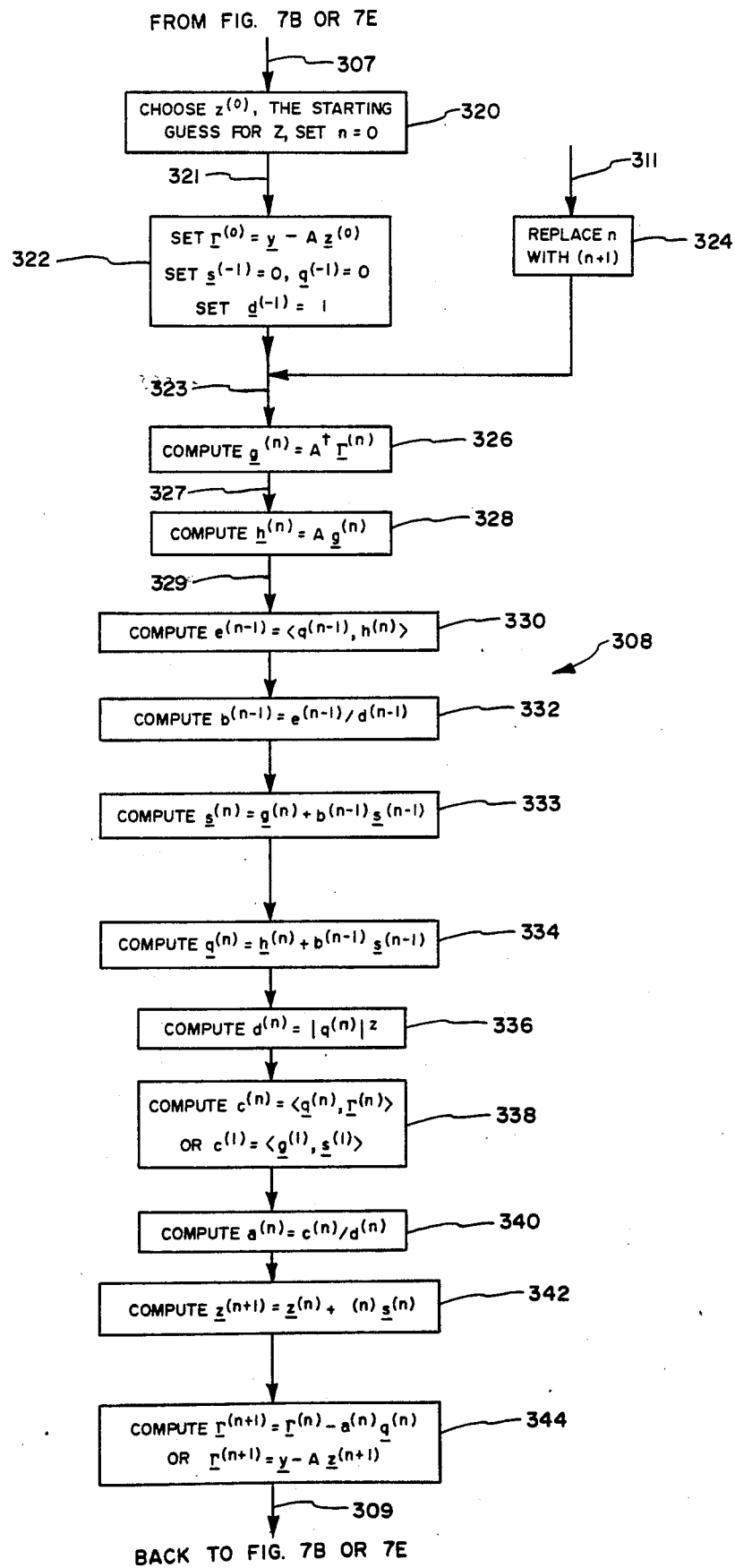

FIG. 7C illustrates the detailed steps of the c.g. step labeled 308. The values of column vector z and the matrix A are passed from step 306 (FIG. 7B) by operation of CPU 118. In step 320, the CPU 118 sets the iterative index to zero and chooses a starting value of $z^{(0)}$. As a default condition, the starting value of $\underline{z}^{(0)}$ may always be selected as zero. In some cases, faster convergence will be obtained by a value closer to the final z. For the case of 5 iterations to find the 5 components of $\Gamma$, the starting value could be any value but zero, or even the frequency average of $\Gamma$ is a reasonable choice.

The result of step 320 is passed by CPU 118 to step 322, where the residual vector $\underline{r}^{(0)}$ is computed by use of equation (35). The temporary calculation vectors $\underline{s}^{(-1)}$ and $\underline{q}^{(-1)}$ are set equal in value to zero and the constant $d^{(-1)}$ is set equal to unity also by CPU 118 in step 322. The result of step 322 is passed to step 326, and CPU 118 increments n, as illustrated at step 324. In step 326, CPU 118 computes $\underline{g}^{(n)}$ via equation (36a). In step 328, the temporary vector $\underline{h}^{(n)}$ is computed by CPU via equation (36b). In step 330, CPU 118 computes the inner product of $\underline{q}^{(n-1)}$ and $\underline{h}^{(n)}$ is taken and assigned to temporary scalar $e^{(n-1)}$ via equation (36c). In step 332, CPU 118 computes the new descent direction scalar weight $b^{(n-1)}$ by dividing $e^{(n-1)}$ by $d^{(n-1)}$ as per equation (36d). CPU 118 then computes in step 332 the new descent $\underline{s}^{(n)}$ from the sum of the previous descent direction $\underline{s}^{(n-1)}$ weighted by $b^{(n-1)}$ and the present gradient $\underline{g}^{(n)}$ as per equation (36e). In step 334, CPU 118 uses equation (36f) to compute the updated value of $\underline{q}^{(n)}$ from $\underline{h}^{(n)}$, $b^{(n-1)}$, and $\underline{q}^{(n-1)}$. In step 336, CPU 118 computes a new value of scalar $d^{(n)}$ from $\underline{q}^{(n)}$ via equation (36g). In step 338, CPU 118 computes a new value of scalar $c^{(n)}$ from either the inner product of $\underline{q}^{(n)}$ and $\underline{r}^{(n)}$ and $\underline{q}^{(n)}$ and $\underline{p}^{(n)}$ via equation (36h). In step 340, CPU 118 computes a new value of descent length scalar weight $a^{(n)}$ by dividing $c^{(n)}$ by $d^{(n)}$, as per equation (36i). In step 342, CPU 118 computes the new and more accurate solution vector $z^{(n+1)}$ by adding the product of descent weight $a^{(n)}$ and descent vector $p^{(n)}$ to previous solution vector $z^{(n)}$, as per equation (36j). In step 344, CPU 118 updates the residual vector $r^{(n)}$ to $r^{(n+1)}$ by use of equation (36k). The output of step 344 is labeled output path 309, which returns control to the subroutine shown in FIG. 7B. Note that a second input path 311 allows entry into the c.g. subroutine for a second, third, or multiple improvements in $z^{(n)}$. Input path 311 leads to step 324, where the value of n is increased by one in preparation for another pass through the c.g. subroutine.

Figure 7D:
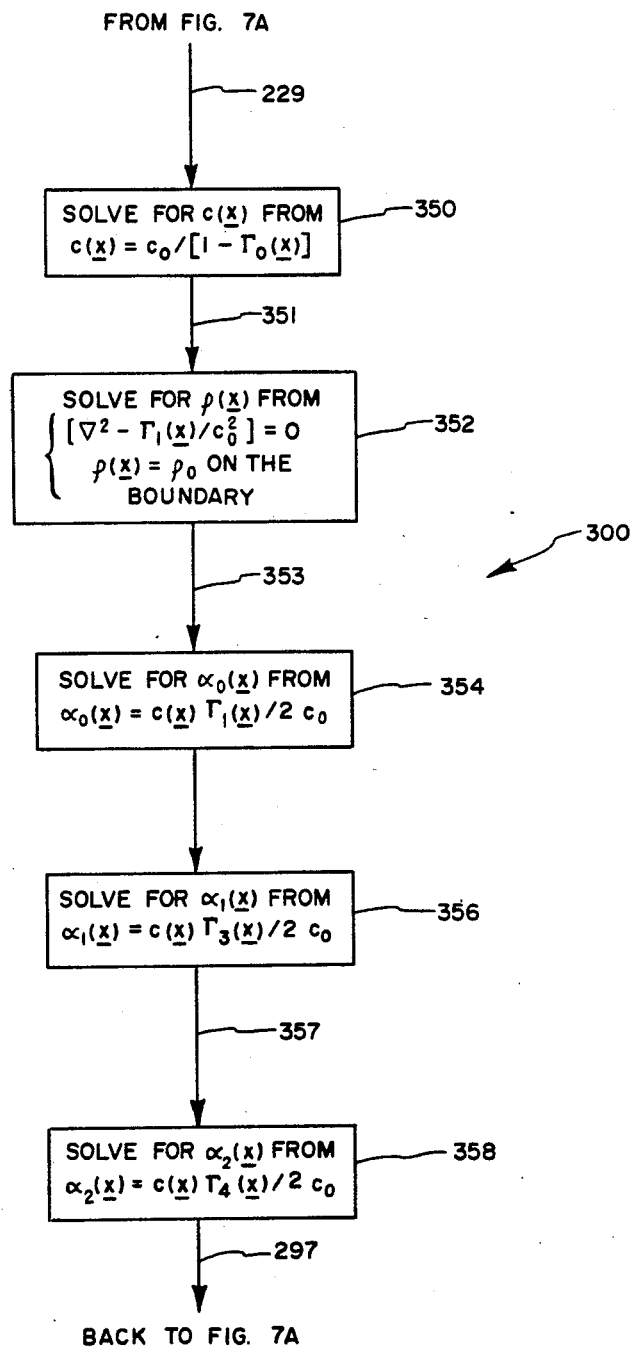

FIG. 7D illustrates the specific detailed steps that comprise general step 300 of FIG. 7A that reconstructs the material parameters $[c(\underline{x}), \rho(\underline{x}), \alpha_o(\underline{x}), \alpha_1(\underline{x}), \alpha_2(\underline{x})]$ from the frequency independent vector $\Gamma(x) = [\Gamma_0(x), \Gamma_1(x), \Gamma_2(x), \Gamma_3(x), \Gamma_4(x)]$. Input path 229 frm convergence test 208a (FIG. 7A) enters at step 350, where $c(\underline{x})$ is obtained from $\Gamma_o$ by use of equation (26). Then, CPU 118 stores the result $c(\underline{x})$ and proceeds to step 352, where $\rho^{-\frac{1}{2}}$ is computed by solving the partial differential equation with associated boundary values described by equation (27). After calculating $\rho^{-\frac{1}{2}}(\underline{x})$, the reciprocal of the square of $\rho^{-\frac{1}{2}}(\underline{x})$ is computed by CPU 118 to obtain $\rho(\underline{x})$. A more detailed explanation of step 352 is given in FIG. 7E. The result from step 352 is stored by CPU 118 and control proceeds to step 354, where CPU 118 computes $\alpha_o(\underline{x})$ from $\Gamma_2(\underline{x})$, $c_o$, and the result $c(\underline{x})$ from step 350 above. CPU 118 uses equation (28) to compute $\alpha_o(x)$ and then stores the result and exists step 354. In step 356, CPU 118 computes $\alpha_1(\underline{x})$ from equation (29), then stores the result and exits to step 358. In step 358, CPU 118 computes $\alpha_2(\underline{x})$ from equation (30), then stores the result and exists via control output path 297 back to step 210a (FIG. 7A) of the main program.

Figure 7E:
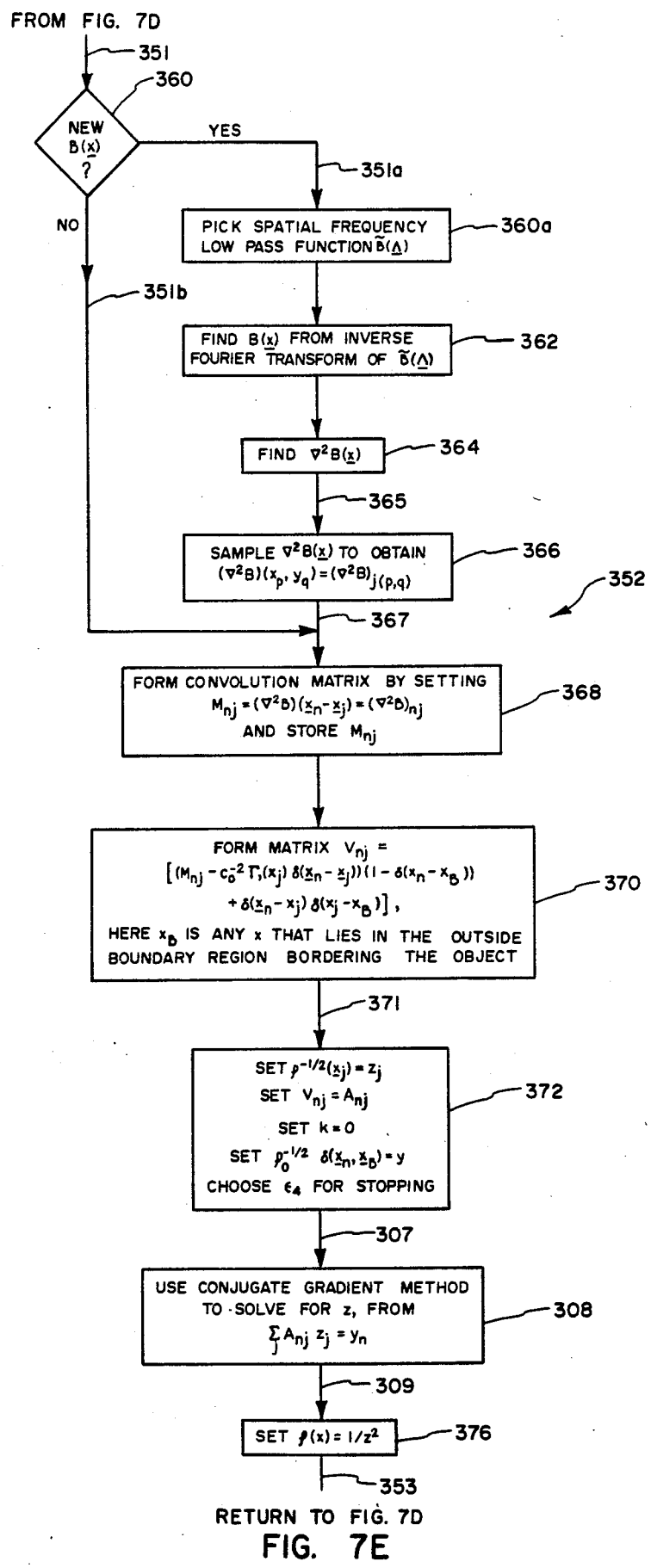

FIG. 7E illustrates the specific detailed steps that comprise general step 352 in FIG. 7D, where the material parameter $\rho(\underline{x})$ is calculated. The input control path 351 under control of CPU 118 passes the image $\Gamma_1(\underline{x})$, the scalar $c_o$, and the boundary values $\rho(\underline{x}_b)$ for $\underline{x}_b$ on the boundary, into step 360. In step 360, a test is made to determine whether a stored Laplacian operator $M_{nj}$ may be used or whether a new Laplacian operator should be calculated. If the stored Laplacian operator is used, then control passes along path 351b to step 368; otherwise control passes along path 351a to step 360a. In step 360a, a lowpass filter function $B(\Lambda)$ in the spatial frequency domain is selected that will pass all spatial frequencies without or almost without attenuation up to a transition band where the attenuation drops to zero or nearly zero. The width of these two bands are chosen to match the potential spatial frequencies of the images, as determined by the data and the system hardware. The final choice $B(\Lambda)$ is passed to step 362, where the inverse Fourier transform of $B(\Lambda)$ is taken by CPU 118 to obtain $B(\underline{x})$. The function $B(\underline{x})$ is delivered to step 364. In step 364, the Laplacian of $B(\underline{x})$ is computed in the spatial frequency domain. The result of step 364 is passed by CPU 118 to step 366. In step 366, the Laplacian of B is sampled on a two-dimensional grid to match the image that is desired and the result is passed on to step 368. In step 368, the sampled Laplacian of B is renamed matrix M for future computation.

From step 368 control passes to step 370, where a new matrix $\{V_{nj}\}$ is formed by CPU 118 from $M_{nj}$ and $\Gamma$ by use of equations (42), (43), and (44). The form of $V_{nj}$ is givne by equation (45b). The matrix $\{V_{nj}\}$ is passed to step 372, where CPU 118 renames the variables $\rho^{-\frac{1}{2}}(\underline{x}_j)$ as $z_j$, $V_{nj}$ as $A_{nj}$, $\rho_o^{-\frac{1}{2}}\delta(\underline{x}_n, \underline{x}_B)$ as $\underline{y}$, and sets the iteration index $k=0$ in preparation for application of the conjugate gradient method. At the completion of step 372, CPU 118 passes control to step 308 which comprises the c.g. program of FIG. 7C described above. Thus, in step 308, the solution vector $\underline{z} = \{z_j\}$ is obtained by CPU 118 applying the conjugate gradient method. The result of step 308 is passed by CPU 118 via control path 309 to step 376. In step 376, CPU 118 determines the density $\rho(\underline{x})$ by the formula $\rho(x_j) = 1/(z_j)^2$ where $z_j$ is the $z_j$ component of vector $\underline{z}$ that is computed by previous step 308. The density $\rho(\underline{x}_j)$ for all j computed by step 376 is passed via path 353 to step 356 of FIG. 7D, described earlier.

CPU 118 and array processor 120 may be programmed in accordance with the foregoing description of FIGS. 7A-7E using any suitable language that is adapted for the particular type of CPU used. Furthermore, it will, of course, be appreciated that the program may be implemented and written in any one of several forms without departing from the basic methodology described.

EXAMPLE 3

Image Reconstruction Using a Fast, Complete Conjugate Gradient Implementation of Backprojection Concepts The foregoing examples each illustrate programs which use models for image reconstruction based on inverse scattering techniques and application of a mathematical implementation of the concept of backprojection. The implementation (equation 8) was straightforward for the case of single frequency data or data with simple linear frequency-dependent absorption and no density-dependent scattering potential, e.g., equation (2a). For the case of a density dependent and/or general frequency dependent scattering potential, as described, for example, by equations (2b), (20), and (21), backprojection at each frequency, but not over all frequencies, was possible; and thus the frequency independent components of scattering $[\Gamma_0, \ldots, \sigma_4]$ were obtained by a least-squares technique.

A more straightforward method of determining $\Gamma$ directly from equations (4) (with $f_{\omega\phi j}$ fixed) would be more appealing because of its simplicity.

In this example, the c.g. method is applied by applying it alternately to equation (4) to determine $\Gamma_j$, with $\gamma_{\omega j}$ set equal to $M\Gamma_j$, and equation (5) to determine $f_{\omega\phi}l$. Thus equations (4) and (5) are replaced with $$f_\omega^{(sc)}\phi m = \sum_j D_{\omega mj}[M_0\Gamma_{0j} + M_1\Gamma_{2j} + M_2\Gamma_{2j} + M_3\Gamma_{3j} + \quad (46)$$

$$M_4\Gamma_{4j}]f_{\omega\phi j}$$

$$f_{\omega\phi l}^{(in)} = \sum_j [\gamma l_j - C_{\omega l}(M_0\Gamma_{0j} + M_1\Gamma_{1j} + M_2\Gamma_{2j} + M_3\Gamma_{3j} + \quad (47)$$

$$M_4\Gamma_{4j})]f_{\omega\phi l}$$

The c.g. method of equations (35-36) when applied alternately to equations (46) and (47) is straight forward and requires that z be solved alternately for $z = [\Gamma_0, \Gamma_1, \Gamma_2, \Gamma_3, \Gamma_4]$ and $\bar{z} = \{f_\omega\phi l\}$ respectively. The result of repetitive applications of the c.g. method to equations (46) and (47) is a least-squares solution $$r(x_j) = [\Gamma_0(x_j), \Gamma_1(x_j), \Gamma_3(x_j), \Gamma_4(x_j)].$$

From $\Gamma(\underline{x}_j)$ the constants $$[c(\underline{x}_j), \rho(\underline{x}_j), a_0(\underline{x}_j), a_1(\underline{x}_j), a_2(\underline{x}_j)]$$

are obtained as previously described by use of equations (26) through (30), where $\Gamma_1(\underline{x})$ is obtained by solving equations (45a) and (45b).

The computation of $g$ in equation (36a) and $\underline{h}$ in step (36b) requires the multiplication of a vector by a matrix A. When solving equation (47) for $f_{\omega\phi j}$, this matrix A is called $A^{(\ )} = \{\gamma_{lj} - C_{\omega lj}\gamma_{\omega j}\}$ but, when solving equation (46) for $\Gamma$, this matrix A is the product of the matrix $\{D_{\omega nj}f_{\omega\phi j}\}$ with the row vector $[M_{0\omega}, M_{1\omega}, M_{2\omega}, M_{3\omega}, M_{4\omega}]$ and is called $A^{(\gamma)}$. This factorization of the matrices shown above is useful in fast computation of the matrix produced by use of the fast Fourier transform (FFT). Such factorization is used for example in the implementation shown in FIG. 6c for determining the $C_{\omega lj}\gamma_{mj}f_{\omega\phi j}$ term in $A^{(\gamma)}\{f_{\omega\phi j}\}$. This is done by the formula FFT$^1$[(FFT[$\omega\phi j$])·FFT[$l\omega jf_{\omega\phi j}$])]. A similar technique can be also applied by analogy for determining the product $A^{(\ )}\{\gamma_{\omega j}\}$ by use of fast Fourier transforms.

Reference is next made to FIGS. 8A–8I which schematically illustrate an alternate flow diagram for programming CPU 118 and any processor 129 or parallel process 146, or said combination to control the electronics systems of FIGS. 4 or 5 and the apparatus of FIGS. 1–3 in accordance with a presently preferred method of the invention. It is understood that FIG. 8A–8I constitute an alternative but related method to those shown in FIGS. 7A–7E and in FIGS. 6A–6F. Like steps will be designated with like numerals to simplify the following explanation.

Steps 200$b$ through 210$b$ are identical to these same numbered steps in FIGS. 6A and 7A. Also, steps 300$b$ and 305$b$ are identical to these same numbered steps in FIG. 7A. Thus the essential difference between FIG. 8A and the previous FIGS. 7A and 6A lies in steps 212$b$ and 214$b$ in FIG. 8A. Notwithstanding this difference, step 212$b$ has the same effect as step 212 or 212$a$ in FIGS. 6A and 7A, which effect is to determine a new estimate of the internal field. Also, step 214$b$ determines the scattering potential by the conjugate gradient method through the generalization of backprojection embodied in equations (46)–(48). Thus, step 214$b$ is similar in effect to step 214$a$ in FIG. 7A or step 214 in FIG. 6A.

In step 212$b$, CPU 118 determines the next estimate of the internal fields $f_{\omega\phi l}^{(in)}$ by solving equation (57) for $f_{\omega\phi l}$ with $\Gamma$ fixed by the conjugate gradient method described by equation (36) and FIG. 7$b$. Here the conjugate gradient variables vector $\underline{z}$, matrix A, and vector $\underline{y}$ are set respectively equal to vector $f_{\omega\phi l}^{(n)}$, matrix $$\left\{ \gamma_{lj} - C_{\omega lj} \sum_{n=0}^{4} M_n \Gamma_n \right\},$$

and vector $\{f_{\omega\phi m}^{(in)}\}$ according to equations (5) and (31). The result from the conjugate gradient method is passed from step 212$b$ via path 213$b$ to step 214$b$. In step 214$b$, the conjugate gradient method is again used to solve equation (56) for $\Gamma$ with $f_{\omega\phi j}$ fixed by the substitutions $\underline{z} = \Gamma$, $\underline{y} = \gamma f_{\omega\phi m}^{(sc)}$, and $A = \{D_{\omega\phi j}f_{\omega\phi j}^{(k+1)}\}M$. The result of this step is passed to step 305$b$ where the vector $\{\gamma_{\omega j}\}$ is computed from $M\Gamma$ by equation (23). The result of step 305$b$ is passed via path 215$b$ to the test step 208$b$. In step 208$b$, if either the norm of $$\left( f_{\omega\phi m}^{(sc)} - \sum_j D_{\omega mj}f_{\omega\phi j}\gamma_{\omega j} \right)$$

is less than $\epsilon_1$ or if the number of passes is greater than some upper number $k_{max}$, then control is passed to step 300$b$. Step 300$b$ has been described in FIGS. 7A, 7D, and 7E. From step 300$b$, control passes to step 210$b$ where the results are stored, displayed, or otherwise utilized, and the total reconstruction of the scattering potential terminates. Additional details of the operation of the steps shown in FIG. 8A may be seen in FIGS. 8B through 8L.

Figure 8A:
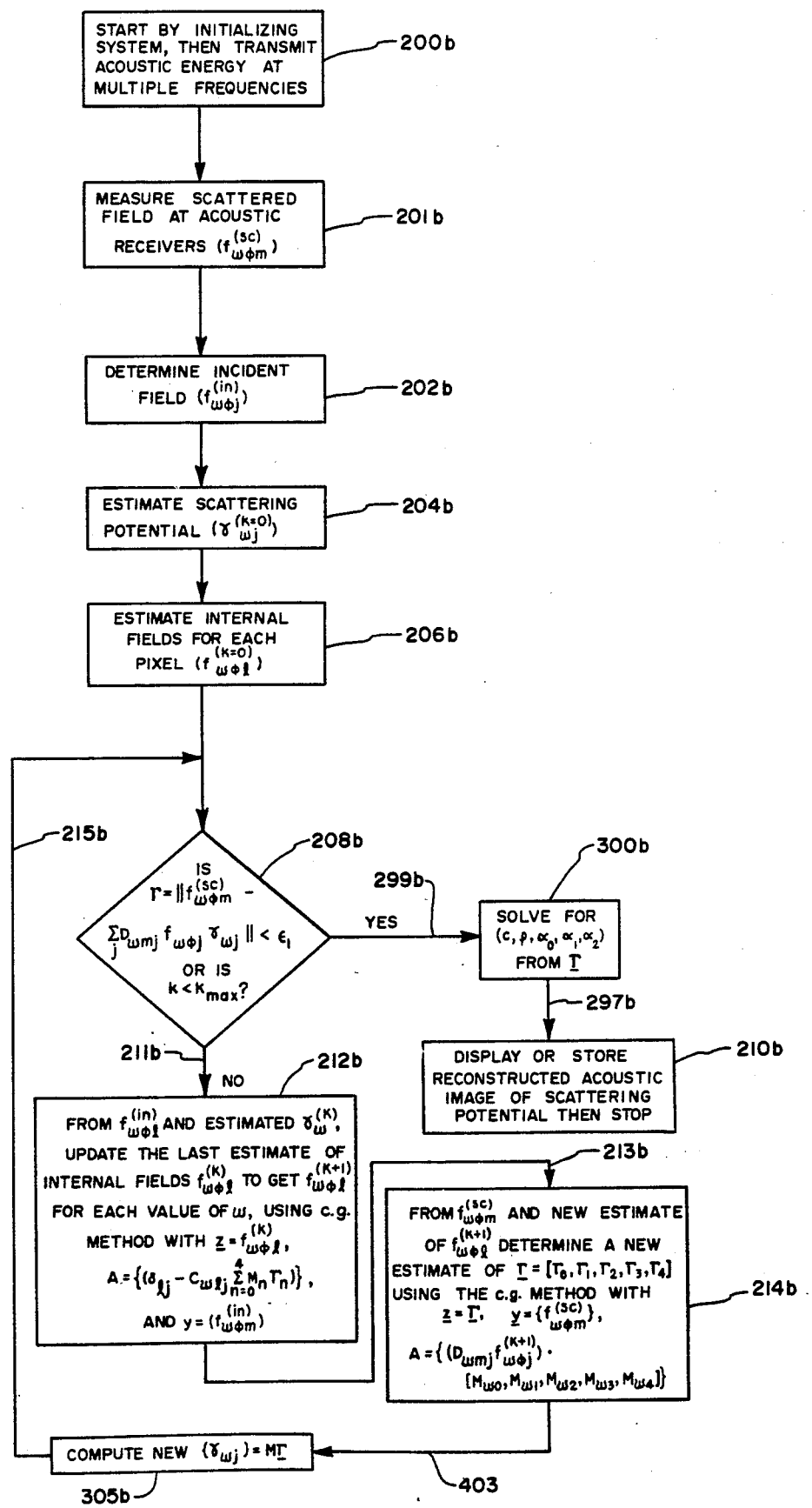
Figure 8B:
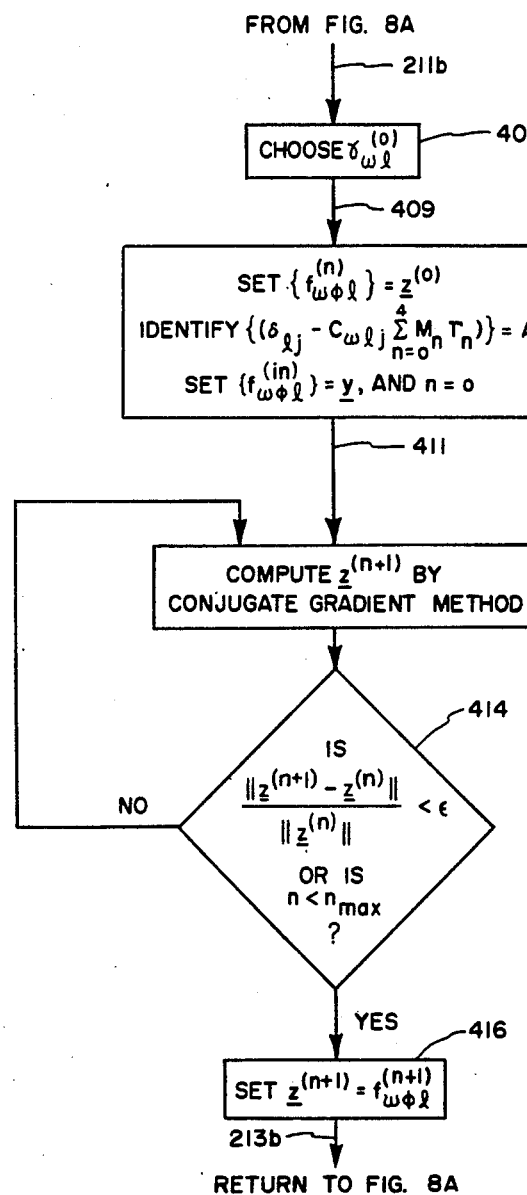

FIG. 8B describes in greater detail the substeps which comprise step 212$b$ of FIG. 8A. Control is passed via path 211$b$ to step 408 in which $\gamma_{\omega l}$ is initialized to zero or any other suitable starting value. In step 410, the present estimate of the internal field $f_{\omega\phi l}^{(n)}$ is set equal to $\underline{z}^{(0)}$, the first interation of $\underline{z}$. Also the matrix $$\left\{ \delta_{lj} - C_{\omega lj} \sum_{n=0}^{4} M_n \Gamma_n \right\}$$

is set equal to matrix A, the known incident field $f_{\omega\phi l}^{(in)}$ is set equal to $\underline{y}$, and the iteration index $n$ is set equal to zero. Control is then passed as represented at path 411 to step 308$b$. In step 308$b$, one iteration of the conjugate gradient method (see FIG. 7C) is performed and control is passed to step 414. In step 414, the fractional change in the norm of the residual is measured and if either it, or the number of passes though the conjugate gradient routine exceeds a maximum number $k_{max}$, then control is passed to step 416; otherwise control is passed back to step 308$b$ for additional iterations of the conjugate gradient method. In step 416, $\underline{z}^{(n+1)}$ is set equal to $f_{\omega\phi l}^{(n+1)}$, the new estimate of $f_{\omega\phi l}$ and control then returns to step 400$b$ of FIG. 8A.

Figure 8C:
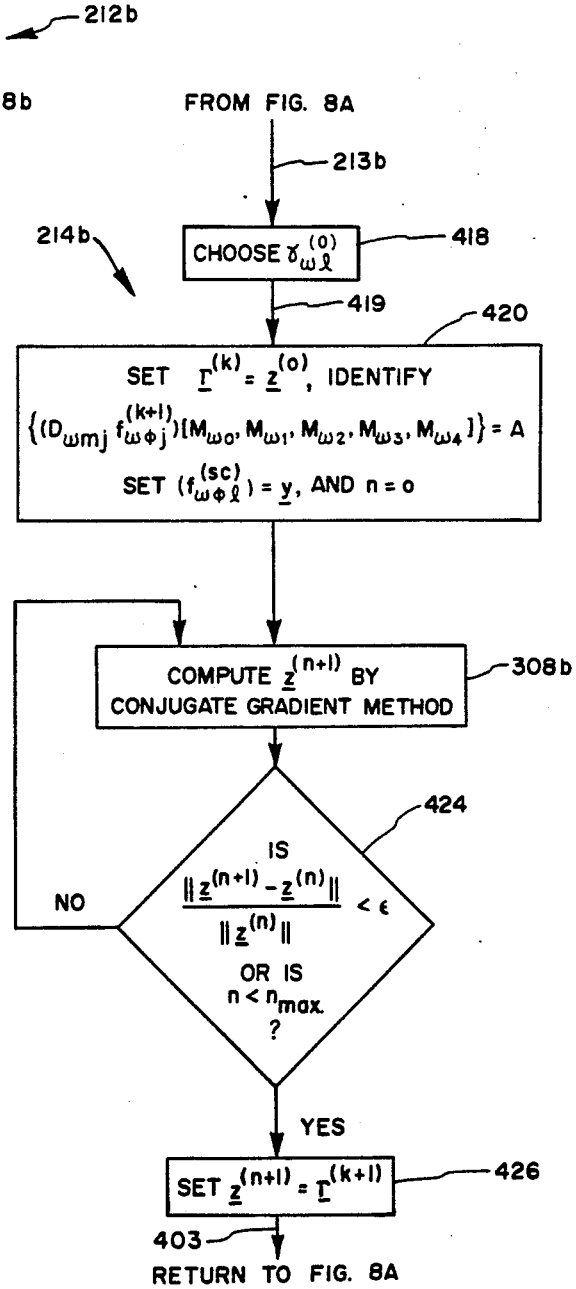

FIG. 8C describes in detail the substeps comprising step 214$b$ from FIG. 8A. In step 418, $\gamma_{\omega l}$ is initialized to zero or any suitable value which forms an initial final guess. In step 420, $\Gamma^{(k)}$, the present estimate of $\Gamma$, is set equal to $\underline{z}^{(0)}$, the initial estimate of $\underline{z}$. Also matrix A is set equal to the matrix given by $\{(D_{\omega mj}f_{\omega\phi j}^{(k+1)})[M_{\omega 0}, M_{\omega 1}, M_{\omega 2}, M_{\omega 4}]\}$ and the vector $\{f_{\omega\phi}^{(sc)}\}$ is set equal to $\underline{y}$. Then control is passed to step 308$b$ where the next estimate of $\underline{z}^{(n)}$ is computed by the conjugated gradient method. The results of step 308$b$ are passed to step 424 where the fractional change in the norm of $\underline{z}^{(n)}$ is computed. If rapid convergence is still being made, then the fractional change is larger than $\epsilon$ and control is returned to step 308$b$. If rapid convergence is not being made, the fractional change in $\underline{z}$ given by $\| \underline{z}^{(n+1)} - \underline{z}^{(n)} \| / \| \underline{z}^{(n)} \|$ is less than $\epsilon$ or the iteration index $n$ is greater than $n_{max}$ and control is passed to step 426. In step 426, the conjugate gradient solution vector $\underline{z}^{(n+1)}$ is set equal to $\Gamma^{(n+1)}$ and control exits back to step 305$b$ of FIG. 8A.

Figure 8D:
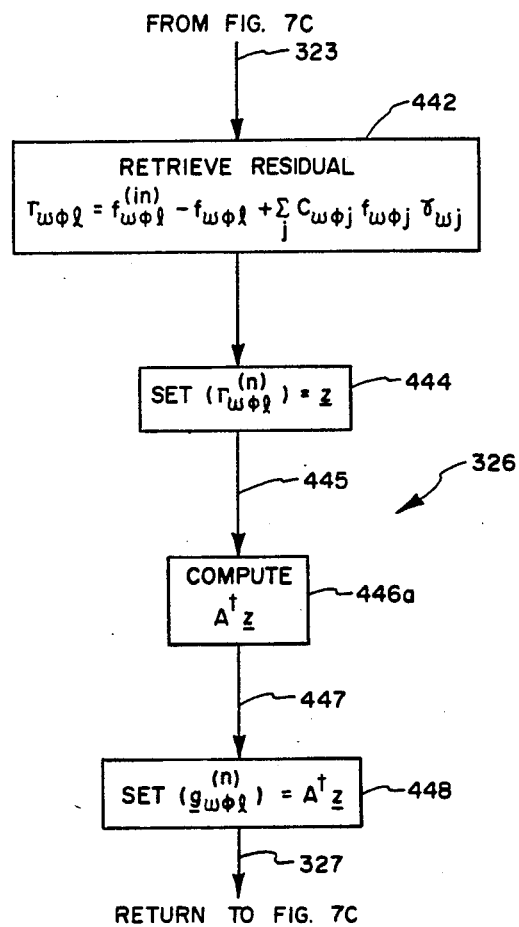
Figure 8E:
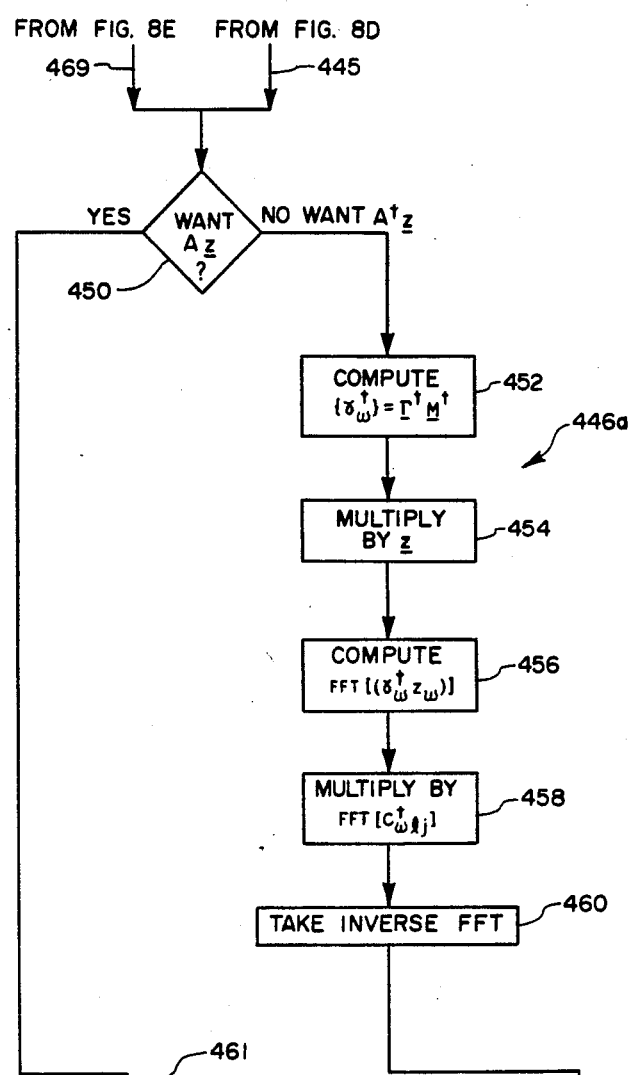
Figure 8E:
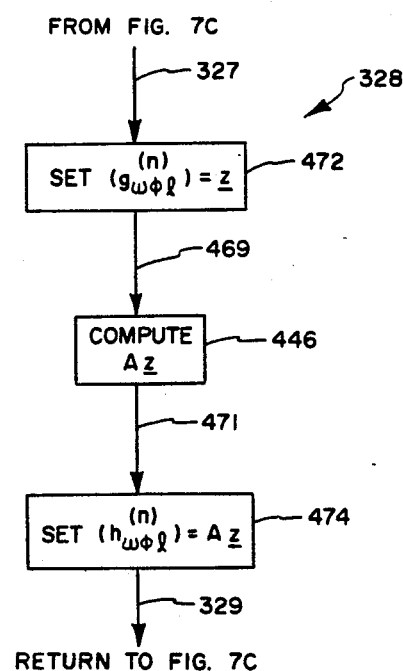
Figure 8F:
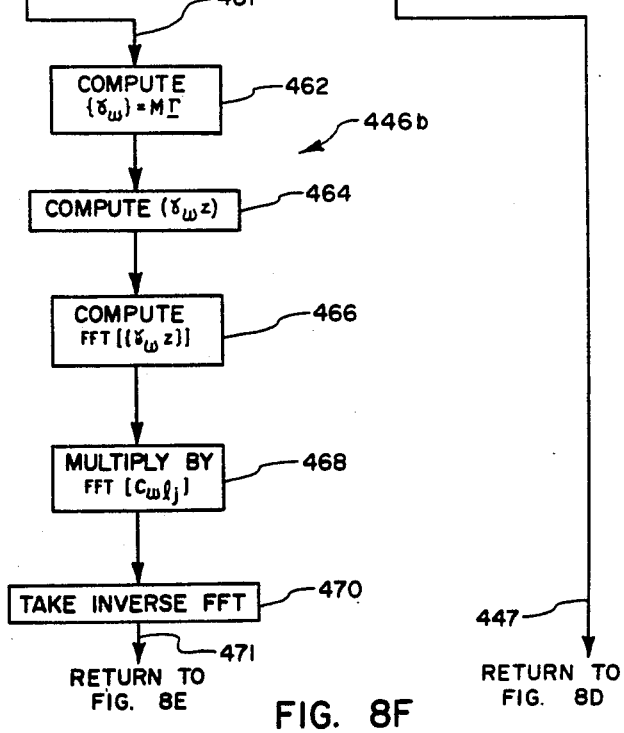

FIGS. 8D–8I show how the conjugate gradient methods of equation (36) may be implemented to determine new field values in a time proportional to ($n^3 \cdot \log n$) for each iteration. FIG. 8D illustrates a rapid method for implementing step 326 of FIG. 7C. When the conjugate gradient method is employed at step 38$b$ in FIG. 8B, step 326 of FIG. 7C is implemented by passing control to step 442 (FIG. 8D) where the residual $\underline{r}_{\omega\phi l}$ is retrieved from storage. The output of step 442 passes to step 444 where the vector z is set equal to the residual. Control then passes to step 446a where z is multiplied by A. In order for this multiplication to be performed rapidly, FFT convolution methods are used as shown in FIG. 8F. The output of step 446 is passed to step 448 where the result of previous step 446 is set equal to $g^{(n)}$ and the result then is returned to step 328 of the conjugate gradient program of FIG. 7C.

FIG. 8E is a more detailed description of a fast method of implementing step 328 in FIG. 7C. Control is passed to step 472 where vector z is set equal to the vector g. Control is then passed to step 446b where z is multiplied by the vector A. Control is then passed to step 474 where the vector h is set equal to Az. Control then exits via path 329 back to the next step in FIG. 7C.

FIG. 8F is a diagram of how steps 446a and 446b of FIGS. 8D to 8E are implemented, respectively. Control enters either via path 469 (from FIG. 8E) or path 445 (from FIG. 8D) to step 450 where a determination is made whether A z or Az is requested. If A z is sought, then control passes from step 450 to step 452. In step 452 $\Gamma M = \gamma_\omega$ is computed. Control then passes to step 454 where the result is multiplied by z. Control then passes to step 456 where the fast Fourier transform is taken, and then to step 458 where the result is multiplied by the fast Fourier transform of $C_{\omega lj}$. Control then passes to step 460 where the inverse fast Fourier transform is taken, and then back to step 448 of FIG. 8D. If Az is requested, then control passes from step 450 to step 462 where $M\Gamma = \gamma_\omega$ is computed. In step 464, the result of the previous step is multiplied by z and passed to step 466. In step 466, the fast Fourier transform is taken and the result passed to step 468, and then multiplied by the fast Fourier transform of $C_{\omega lj}$. In step 470, the inverse fast Fourier transform is taken and control is then returned to step 474 of FIG. 8E.

Figure 8G:
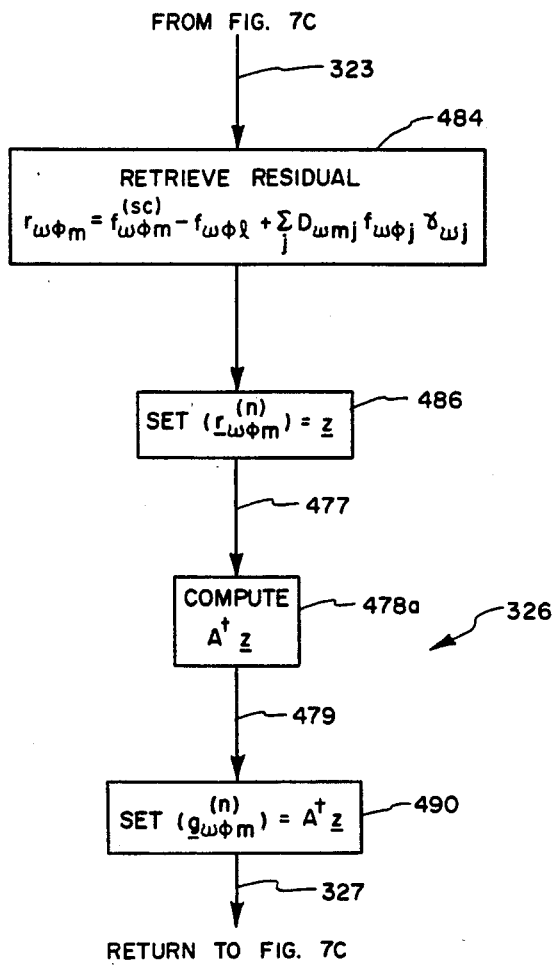
Figure 8H:
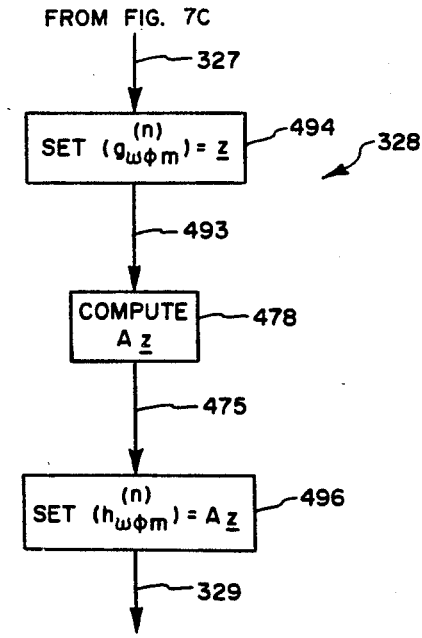
Figure 8I:
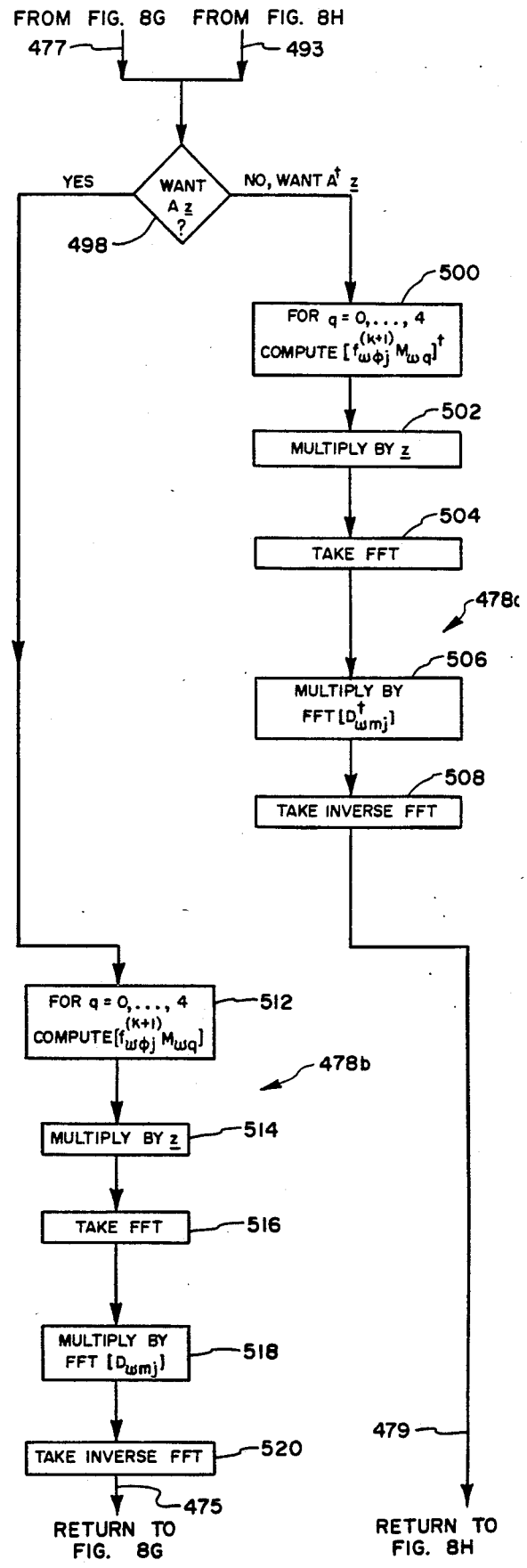

FIGS. 8G, 8H, and 8I are similar to FIGS. 8D, 8E, and 8F in function. FIGS. 8G–8I show how the conjugate gradient methods of equation 36 may be implemented to determine new $\Gamma$ values in a time proportional to ($n^3 \cdot \log n$) for each iteration. FIG. 8G illustrates a rapid method for calculating A z in step 326 of FIG. 7C when the conjugate gradient method is employed in FIG. 8C. Control passes from path 323 of FIG. 7C to step 484 where the residual $r_{\omega\phi m}$ is retrieved from storage. In step 486, the vector z is set equal to the residual obtained from the previous step. The value of z is then passed to step 478a, where A z is computed. The result of step 478 is passed to step 490 where the result is set equal to g. Control then exits step 490 back to step 328 of FIG. 7C.

FIG. 8H shows a fast method for computing Az in step 328 of FIG. 7C. Control enters via path 327 to step 494 where the vector g is set equal to z. Control then passes to step 478 where Az is computed. Control then passes to step 496 where the vector h is set equal to Az calculated in the previous step, and then back to the next step of FIG. 7C.

FIG. 8I is a diagram of how steps 478a and 478b of FIGS. 8G and 8H are determined. Step 98 is entered either via path 477 from FIG. 8G or via path 493 from FIG. 8H. In step 498, a decision is made whether A z or Az is required. If A z is required, then control is passed to step 500, where $\bar{f}_{\omega\phi j}$ is multiplied by $M_{\omega q}$ and the complex conjugate transpose is taken. Then control passes to step 502 where the result of the previous step is multiplied by z. The result is passed to step 504 where the fast Fourier transform is taken, and then to step 506 where it is multiplied by the fast Fourier transform of $D_{\omega mj}$. The result is passed to step 508 where the inverse fast Fourier transform is taken. The result of step 508 exits via path 479 back to step 490 of FIG. 8G. If, however, the result requested in step 498 is Az, then control passes from step 498 to step 512, where $f_{\omega\phi j}$ is multiplied by $M_{\omega q}$. The result of step 512 is multiplied in step 514 by z. This result is passed to step 516 where the fast Fourier transform is taken. The result of step 516 is passed to step 518, where it is multiplied by the fast Fourier transform of $D_{\omega mj}$, and then to step 520, where the inverse fast Fourier transform is taken. The result of step 520 is the vector Az which is returned via path 475 to step 496 of FIG. 8H.

FIG. 8J illustrates in more detail the step 408 in FIG. 8B. In step 530, a decision is made whether a new residual $r_{\omega\phi l}^{(0)}$ is to be computed. For the first few passes through step 400 of FIG. 8A, computing a new residual may help convergence. After two or three passes through step 400, it may be advantageous in time savings to save either the residuals $r_{\omega\phi l}$ or $r_{\omega\phi m}$ or the previous descent vector s or both. No rigor is lost if new residuals and descent vector s are computed for each pass through steps 400 and 402. The reduction in the residuals per pass through steps 400 and 402 will decrease if either the least-squares solution to $\Gamma$ is approached or if the starting residuals and descent directions are not recomputed for each pass. Thus a compromise between reducing the number of passes through steps 400 and 402 and shortening the time spent in each step may be reached that may improve overall time to convergence by a small but significant percentage. If recomputing is not required, control passes to step 536 and the existing residual is retained. If a new residual is required, then control passes to step 532. In step 532, the value of $\gamma_{107} M\Gamma$ is retrieved from memory and the sum $$\sum_j C_{\omega lj} f_{\omega\phi j} \gamma_{\omega j}$$

is then determined in step 216b as per FIG. 6C. Control passes from step 216b to step 534 in which the value of $f_{\omega\phi j}^{(in)}$ minus $f_{\omega\phi l}$ is added to the results of previous step 216b. The result is the new residual and is passed to step 536 where it is stored.

FIG. 8K illustrates a fast method for computing the initial residual $r_{\omega\phi m}^{(0)}$ and is similar in purpose to FIG. 8J (where the residual $r_{\omega\phi l}^{(0)}$ was computed). FIG. 8K shows in detail the step 418 of FIG. 8C. In step 540, a decision is made whether the present residual is to be used or whether a new residual is to be calculated. If the present residual is satisfactory, then control is passed to step 548 and the present residual is stored. If a new residual is desired, then control is passed to step 542 where the present value of $\gamma_\omega$ is retrieved from storage. In step 544, a fast method for computing $\Sigma D_{\omega mj} f_{\omega\phi j} \gamma_{\omega j}$ is implemented. After completion of this task, control is passed to step 546 where the sign of the result is changed and the value of $f_{\omega\phi m}^{(sc)}$ is added to form the desired residual $r_{\omega\phi m}^{(0)}$. Control then passes to step 548 in which the residual is stored for future use.

FIG. 8L shows the detailed substeps which comprise step 544 of FIG. 8K. In step 550, the present value of $f_{\omega\phi j}$ is multiplied by the present value of $\gamma_{\omega j}$. Control is then passed to step 552, where the fast Fourier transform is taken. The result of step 552 is passed to step 554, where it is multiplied by the fast Fourier transform of $D_{\omega mj}$. Control is then passed to step 556, where the inverse Fourier transform is taken. The resulting value is then returned to step 546 of FIG. 8K.

Figure 9:
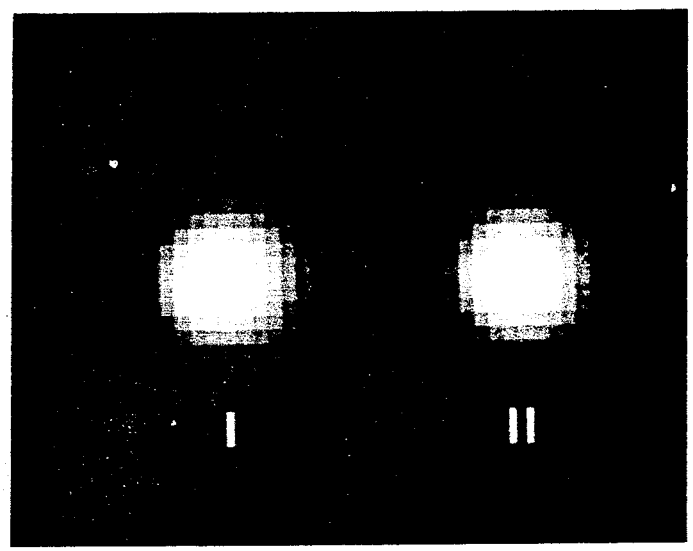
FIG. 9 is a photograph of a television display screen showing an image that simulates a cancer and an actual image obtained as the inverse scattering solution using the method and a computer simulation of the apparatus of the present invention.

FIG. 9 illustrates the operation of the invention using the methods of Example 3 to produce an actual image from scattering data. FIG. 9 is composed of two images, each labeled, respectively, by a Roman numeral I or II placed directly below. This composit image was photographed directly from a television display screen. The image on the left labeled by I is a 15 by 15 pixel image of a simulated tumor. The separation of each pixel is one-fourth wavelength of the incident field. The tumor is simulated by a Gaussian distribution of both speed of sound and absorption. Only the speed of sound function component is shown, since the absorption image is so similar. The function shown is $U(x) = 10,000(1 - c_o^2/c^2(x)) = 10,000\ \Gamma_1(x)$ where $c_o = 1500$ m/s. Then the 15 values of $U(\underline{x})$, for example, along the diagonal from top left to bottom right as displayed in the image I are (10, 34, 95, 222, 429, 687, 910, 1000, 910, 687, 429, 222, 95, 34, 10). Thus, since $(\Delta c/c_o) \approx (\frac{1}{2})\Delta\Gamma$, and since $10,000\ \Delta\Gamma_1 = (1000-10) \approx 1000$, it follows that $(\Delta c/c_o) \approx (\frac{1}{2})(1/10) = 0.5$ in image I. In other words, image I represents a 5 percent change in speed of sound over a region about $15/4 \approx 4$ wavelength in diameter. For 3 MHz ultrasound in the human body, this corresponds to a tumor of 2 wavelengths in average diameter or of 1 mm average diameter. Image I was used to generate scattering data to test the reconstruction method of Example 3. The image I was used to generate 15 separate scattering data records at a single frequency for 15 respective incident plane waves distributed every $360/15 = 24$ degrees around a circle. 56 detectors surrounding the object were used. Thus, $(56)(15) = 840$ scattered field measurements were obtained.

The image labeled II on the right in FIG. 9 was reconstructed (using scattering data generated from image I) by the application of the particular inverse scattering method of this invention described in method 3. The scaling is identical to that in Image I. The 15 values of the reconstructed function $U(\underline{x})$ along the diagonal from top left to bottom right are (10, 34, 95, 223, 431, 687, 910, 1001, 911, 687, 430, 223, 96, 34, 10). Thus, the maximum deviation from the correct values of image I along this diagonal is 1.0 percent, and the average deviation is about 0.2 percent. The maximum deviation divided by the peak value is about 0.2 percent. As FIG. 9 demonstrates, the fidelity, accuracy, and quality of reconstruction of the actual object is remarkably high. The image quality of FIG. 9-II is so good that the eye can detect no difference between the image of the original object I and the reconstruction II. The reconstruction of absorption is of similar accuracy, quality, and fidelity. An example of one presently preferred program listing which uses a simplified c.g. method from that described in the flow chart is included in Appendix A hereto. The program listing is in ANSI FORTRAN. This program was used to produce the scattering data from image I in FIG. 9 and to reconstruct image II in FIG. 9. It should be recognized that the invention lies in the apparatus and method defined by the claims, and is not intended to be limited by the representative program listing set forth in Appendix A.

EXAMPLE 4

Image Reconstruction Using a Descent Direction Containing both Scattering Potential Components and Field Components and Using an Objective Function Containing All Detector Measurement Equations and All Internal Field Equations The foregoing Examples 1, 2, and 3 described how the inverse scattering problem may be solved by various iterative techniques that had the following feature in common: They all alternately solved the internal field equations (5) for an improved field while holding the scattering potential fixed and then solved the detector or measurement equations (4) for an improved scattering potential while holding the internal fields fixed. These two steps are shown, respectively, as 212 and 214 in FIG. 6A. In FIG. 7A, improving the solutions for the fields is shown as step 212a and for the scattering potential as steps 214a, 304, and 305. In FIG. 8A, determination of the internal fields is shown as steps 212b and the determination of the scattering potential as steps 214b and 305b. It would be an advantage to develop a procedure that combined the two steps of obtaining fields and scattering potential into one step in order to obtain a more rapid convergence to the solution. Such a procedure is possible and is explained in this example.

Obtaining an iterative procedure that updates both the internal fields and the scattering potential at each iterative step can be accomplished by defining a new total objective function that is the sum of the norm of the field equation residuals and the measurement detector residuals. Let F be that total objective function. Then F is given by $$F = \|\{r_{\omega\phi l}^{(fld)}\}\|_2^2 + \|\{r_{\omega\phi m}^{(sc)}\}\|_2^2 \tag{48}$$

$$= \sum_{\omega\phi l} |r_{\omega\phi l}^{(fld)}|^2 + \sum_{\omega\phi m} |r_{\omega\phi m}^{(sc)}|^2$$

where $r_{\omega\phi l}^{(fld)}$ is given by equation (7b) and $r_{\omega\phi m}^{(sc)}$ is given by equation (18). Let $\underline{v}$ be the column vector that contains all of the field and scattering potential components. Then $\underline{v}$ is the transpose of $\underline{v}^T$ where $\underline{v}^T$ is a row vector given by $$\underline{v}^T = [\Gamma, \underline{f}] = [\{\Gamma_h\}, \{f_\omega\}]. \tag{49a}$$

where $$\Gamma_h = \{\Gamma_{hj}\} \tag{49b}$$

$$f_\omega = \{f_{\omega\phi}\} \tag{49c}$$

$$f_{\omega\phi} = \{f_{\omega\phi j}\} \tag{49d}$$

Using this notation, $r_{\omega\phi}^{(fld)}$ and $r_{\omega\phi m}^{(sc)}$ are functions of $\underline{v}$ and thus F is a function of $\underline{v}$. i.e., $F = F(\underline{v})$. Thus, the value of $\underline{v}$ that minimizes $F(\underline{v})$, where F is given by equation (48), is the least-squares solution for $\gamma$ and $\underline{f}$ to equations (46) and (47). To minimize $F(\underline{v})$, an estimate for $\underline{v}$ is chosen and a correction $\Delta\underline{v} \equiv \underline{s}$ is found that reduces the value of $F(\underline{v})$. This may be written as $$\underline{v}^{(k+1)} = \underline{v}^{(k)} + \Delta\underline{v}^{(k)} \tag{50}$$

Then, $$F(\underline{v}^{(k+1)}) < F(\underline{v}^{(k)}) \tag{51}$$

except at the minimum of F.

The vector $s = \Delta v^{(k)} = v^{(k+1)} - v^{(k)}$, since it reduces the value of $F(\underline{v})$, is called a "descent direction." Clearly, if $s = \Delta v^{(k)}$ were chosen perfectly, then the minimum of $\bar{F}(\underline{v})$ could be found in one step. Finding such a perfect descent direction is unlikely, so more structured and formal techniques to find good but not perfect descent directions are used. Three such versions for finding a good or useful but not perfect descent directions will be given and are:

4.a Method of steepest descent version of Example 4.
4.b Method of accelerated steepest descent version of Example 4.
4.c The conjugate gradient method version of Example 4.

Versions 4.a, 4.b, and 4.c of method 4 are here ranked in order of increasing speed of convergence (require fewer iteratives of obtaining equal closeness of convergence) and increasing order of complexity.

The steepest descent version (version 4.a) is described by the iterative step $$v^{(k+1)} = v^{(k)} + \alpha_2 \nabla F(v^{(k)}) \quad (52)$$

where $\alpha_2$ minimizes $F(v^{(k)} + \alpha_2 \nabla F(v^{(k)}))$. The descent direction is thus given by $-\nabla F$, i.e., along the negative gradient of F, and the length of the descent direction is $\alpha |\nabla F|$. Finding $\alpha_2$ is thus equivalent to finding the minimum of F along the line of direction $-\nabla F$ and such a procedure is called a "line search" along a descent direction.

The gradient of F may be written $$g = \nabla F = \nabla_\Gamma F + \nabla_f F = g_\Gamma + g_f \cdot \quad (53a)$$

where $\nabla_\Gamma$ means the gradient operator with respect to the scattering potential $\Gamma$ and $\nabla_f$ means the gradient operator with respect to all of the field variables $f = \{f_{\omega\phi j}\}$. Thus, $$g_\Gamma = \nabla_\Gamma F = \nabla_\Gamma \| r_{\omega\phi}^{(fld)} \|^2 + \nabla_\Gamma \| r_{\omega\phi m}^{(sc)} \|^2 \quad (53b)$$

and $$g_f = \nabla_f F = \nabla_f \| r_{\omega\phi}^{(fld)} \|^2 + \nabla_f \| r_{\omega\phi m}^{(sc)} \|^2 \quad (53c)$$

It is noted that $\nabla_\Gamma \| r_{\omega\phi m}^{(sc)} \|^2$ and $\nabla_f \| r_{\omega\phi}^{(fld)} \|^2$ are the same gradients used previously in Example 3 and illustrated in FIG. 8 as components of steps 214b, 305b, and 212b. Thus, only two procedures to compute the additional gradient terms need to be described to implement the total gradient of F as given by equations (53a), (53b), and (53c). Fortunately, the same general fast Fourier transform procedures, as illustrated in Examples 2 and 3 above, may be used to compute the two additional gradient terms $\nabla_\Gamma \| r_{\omega\phi}^{(fld)} \|^2$ and $\nabla_f \| r_{\omega\phi m}^{(sc)} \|^2$. Thus, all terms in equations (53a–53c) may be computed rapidly using the fast Fourier transform.

The minimum of F with respect to $\alpha$ in the line search direction $-\nabla F(\underline{v}^{(k)})$ is estimated by the quadratic interpolating functions $q(\alpha)$. Therefore, let $$q(\alpha) = A\alpha^2 + B\alpha + C \approx F[\underline{v}^{(k)} + \alpha \nabla F(\underline{v}^{(k)})] \quad (53)$$

Three conditions on $q(\alpha)$ allow A, B, and C to be determined:

a. $q(0) = F(v^{(k)}) = C$ \hfill (54a)

b. $q'(0) = -<\nabla F(v^{(k)}),$
$\nabla F(v^{(k)})> = -|\nabla F(v^{(k)})|^2 = B$ \hfill (54b)

c. At a second value of $\alpha$, say $\alpha_1$, $q(\alpha_1)$ is determined. \hfill (54c)

Thus, $$q(\alpha_1) = F[v^{(k)} + \alpha_1 \nabla F(v^{(k)})] = A\alpha_1^2 + B\alpha_1 + C \quad (55)$$

Thus, $$A = [F(v^{(k)} + \alpha_1 \nabla F(v^{(k)})) + \alpha_1 |\nabla F(v^{(k)})|^2 - F(v^{(k)})]/\alpha_1^2 \quad (56)$$

The minimum of $q(\alpha)$ occurs at $\alpha_2$ when $$2A\alpha_2 + B = \frac{dq(d)}{d\alpha} = 0,$$

therefore, $$\alpha_2 = \frac{-B}{2A} \quad (57)$$

This algorithm has been implemented and tested and convergence is linear in rate.

The accelerated steepest descent version (version 4.b) uses an accelerating extrapolation step, alternating with a steepest descent step. The extrapolation step determines each even point in terms of the most recent two odd points in the sequence. The steepest descent step determines each odd point in the sequence, starting from the previous even point. However, the first two steps are steepest descent to establish the first two odd points, assuming the procedure starts from point one. The procedure often greatly accelerates the convergence of steepest descent because it tends to damp oscillations and find the trend toward the minimum. This method may be written $$v^{(2)} = v^{(1)} \alpha \nabla F(v^{(1)}) \quad (58a)$$

$$v^{(k+1)} = v^{(k)} + \alpha^{(k)} s^{(k)}, \quad k = 2, 3, 4, \ldots \quad (58b)$$

$$s^{(k)} = -\nabla F(v^{(k)}), \quad k = 2, 4, 6, \ldots \quad (58c)$$

$$s^{(k)} = (v^{(k)} - v^{(k-2)}), \quad k = 3, 5, 7, \ldots \quad (58d)$$

where $\alpha^{(k)}$ is found by the line search formula given for the steepest descent method above.

The conjugate gradient method can be extended to find the minimum of the complete objective function given by equation (48); this procedure shall be called version 4.c of method 4.

The conjugate gradient version of method 4 then shares some features with those of Examples 2 and 3. This new method may be written $$v^{(k+1)} = v^{(k)} + a^{(k)} p^{(k)} \quad (59a)$$

where $$a^{(k)} \text{ minimizes } F(v^{(k)} + ap^{(k)}) \quad (59b)$$

and where $p^{(k)}$ is the descent direction defined by by $$p^{(k)} = -g^{(k)} + b^{(k)} p^{(k-1)} \quad (59c)$$

```
      print *,'Want to print the pix-pix coeff.? (1/0)'
      read *,ippix
      if (ippix.eq.1) call cpprnt(iJmax,pix)
c.
      print *,'Enter remin and maxit:'
      read *, remin, maxit
c
      print *,'Assigning AP memory and transferring data to AP...'
c
c -------------------------------------------------------------
c        Assign the AP memories
c -------------------------------------------------------------
c
      kertk  = 46
      kerin  = 47
      kesn   = 48
      kr1kn  = 49
      kr2kn  = 50
      ks1kn  = 51
      khpkn  = 52
      kalpha = 53
      kbeta  = 54
      krelek = 55
      ktotn  = 56
      keskn  = 57
      ks2kn  = 58
      krele  = 59
      kpix   = 100
      kxi    = kpix + iJm2
      kyj    = kxi + iJmax
      kes    = kyj + iJmax
      kinc   = kes + iJm2
      ktot   = kinc + nam2
      kef    = ktot + nam2
      kcf    = kef + nam2
      kcnv   = kcf + nsa2
      kesm   = kcnv + nsa2
      ktmp   = kesm + iJm2
      ktf    = ktmp + nam2
      ksk    = ktf + nsa2
      kp1k   = ksk + nam20
      kp2k   = kp1k + iJm2
      kesk   = kp2k + nam2
      khp1k  = kesk + iJm2
      khp2k  = khp1k + nam2
c
c -------------------------------------------------------------
c              Transfer data to AP
c -------------------------------------------------------------
c
      call apclr
      call vclr(0,1,65000)
      call apput(aim,kim,1,2)
      call apput(aJm,kJm,1,2)
      call apput(sim,kmim,1,2)
      call apput(sJm,kmJm,1,2)
      call apput(psm,kpsm,1,2)
      call apput(cor,kcor,1,2)
      call apput(coi,kcoi,1,2)
      call apput(one,kone,1,2)
      call apput(two,ktwo,1,2)
      call apput(dela,kdela,1,2)
```

```
      call apput(stph,kmtph,1,2)
      call apput(rnsa,krnsa,1,2)
      call apput(pix,kpix,ijm2,2)
      call apput(half,khalf,1,2)
      call apwd
c
c     ----------------------------------------------------------------
c         Define the test object and internal filed
c     ----------------------------------------------------------------
c
      print *,'Defining object and incident field usig AP ...'
      call edefinc(imax,Jmax,nand,n,1)
      call apwr
c
      print *,'Want to print the true sama? (1/0)'
      read *,ires
      if(ires.eq.1) then
      call apget(etmp,keg,ijm2,2)
      print *,'The sama!'
      call cmprnt(ijmax,etmp)
      endif
c
      print *,'Want to print the incident field? (1/0)'
      read *,ipinc
      if(ipinc.eq.1) then
      call apget(etmp,kinc,nam2,2)
      call apwd
      print *,'The incident field:'
      call cmprnt(nam,etmp)
      endif
      print *,'want to check the computed internal field ?(1/0)'
      read *,icheck
c
c     ----------------------------------------------------------------
c     Calculate the scattered field using the true object
c     ----------------------------------------------------------------
c
      print *,'Computing the scattered field using AP ...'
      call sctfld(xi,uj,etmp,icheck)
      call apwr
c
      print *,'Want to print the true internal field? (1/0)'
      read *,iptot
      if(iptot.eq.1) then
      call apget(etmp,ktot,nam2,2)
      print *,'The true internal field:'
      call cmprnt(nam,etmp)
      endif
c
      print *,'Want to print the scattered field? (1/0)'
      read *,ipsct
      if(ipsct.eq.1) then
      call apget(etmp,kef,nam2,2)
      call apwd
      print *,'The scattered field:'
      call cmprnt(nam,etmp)
      endif
c
c     ----------------------------------------------------------------
c     Solving the inverse and forward problems alternately using
c     conjugate gradient method
c     ----------------------------------------------------------------
```

```
c
        print *,'How many iterations for inv. sys. each step? (>2)'
        read *,ninv
        print *,'Solving the projection problem using C-G and AP ...'
        call altncg(etmp,remin,maxit,ninv)
        call apwr
c
        print *,'Want to print the estimated dama? (1/0)'
        read *,ipede
        if(ipede.eq.1) then
        call apget(etmp,kesk,iJm2,2)
        print *,'The estimated dama:'
        call cmprnt(iJmax,etmp)
        endif
c
        print *,'Want to print the estimated internal field? (1/0)'
        read *,iptote
        if(iptote.eq.1) then
        call apget(etmp,ktot,nam2,2)
        call apwd
        print *,'The estimated internal field:'
        call cmprnt(nam,etmp)
        endif
c
        call apget(etmp,kes,iJm2,2)
        call apwd
        print *,'Want to plot the object? (1/0)'
        read *,ipobJ
        if(ipobJ.eq.1) then
        write(6,10)
10      format(///,'The original image of Gaussian test object:',//)
        endif
        call image(ib,Jb,iJmax,iJm2,etmp,ipobJ,2)
c
        call apget(etmp,kesk,iJm2,2)
        call apwd
        print *,'Want to plot the reconstruction? (1/0)'
        read *,irrec
        if(irrec.eq.1) then
        write(6,20)
20      format(///,'The reconstructed image of the object:',//)
        endif
        call image(ib,Jb,iJmax,iJm2,etmp,irrec,3)
c
        close(1)
        close(2)
        close(3)
        stop
        end subroutine image(ib,Jb,iJmax,iJm2,etmp,ipobJ,nfile)
        integer imgr(225),imgi(225)
        complex etmp(1),eJunk(225)
c
4       continue
        do 5 i = 1, iJmax
           rel = real(etmp(i))
           aim = aimag(etmp(i))
           if(rel.ge.0.) then
              oddr = 0.5
```

```
          else
            oddr = -0.5
          endif
          if(aim.gt.0.) then
            oddi = 0.5
          else
            oddi = -0.5
          endif
          imsr(i) = rel*10000. + oddr
          imsi(i) = aim*10000. + oddi
   5    continue
c
        ips = iJmax - ib + 1
        ipe = iJmax
        do 10 J = 1, Jb
          if(iprobJ.eq.1) then
          write(6,20) (imsr(i),i=ips,ipe)
          write(6,20) (imsi(i),i=ips,ipe)
          print *,' '
          endif
          do 15 i = 1,ib
            kt = (J-1)*ib + i
            kJ = (Jb -J)*ib + i
  15        eJunk(kJ) = etmp(kt)
          ipe = ips - 1
          ips = ips - ib
  10    continue
  20    format(15i5)
c
        write(nfile,30) (eJunk(i),i=1,iJmax)
  30    format(8f10.5)
        return
        end c -------------------------------------------------------------
        subroutine altncs(etmp,remin,maxit,ninv)
c
c       This is a subroutine to solve the inverse scattering
c       problem by solving the forward and inverse problem
c       alternately using c-g iterations.
c -------------------------------------------------------------
c
        complex etmp(1),btn
        common /const/imax,Jmax,nang,n,ib,Jb,ic,iJmax,iJm2,
     *       nam,nam2,nsa,nsa2
        common /saddr/ks1kn,ks2kn,khpkn,kalpha,
     *       kbeta,krelok,krele,ktotn,kesn,keskn,kerin,kertk
        common /vaddr/kpix,kxi,kuJ,kes,kinc,ktot,kef,kcf,kcnv,
     *       kesm,ktmp,ktf,ksk,kp1k,kp2k,kesk,khp1k,khp2k
c
        kbtn = 42
        kr1kn = 49
        print *,'C-G iterations for solving the projection problem:'
        k = 0
  10    k = k + 1
        if(k.eq.1) goto 15
        call fwcsap(imax,Jmax,nang,n,k,kesk)
        call apwr
  15    continue
c       print *,'before solving inverse system:'
        inv = 0
```

```
 16    inv = inv + 1
       if(inv.lt.ninv.or.(ninv.eq.1.and.k.eq.1)) then
          ier = 0
       else
          ier = 1
       endif
       if(k.eq.1.and.inv.eq.1) then
          itype = 1
       else
          itype = 2
       endif
       call ivcsar(imax,jmax,nans,n,k,itype,ier)
       call arwr
       if(inv .lt. ninv) goto 16
c
       call arset(ertk,kertk,1,2)
       call arset(relek,krelek,1,2)
       call arset(rele,krele,1,2)
       ertk = sart(ertk)
       relek = sart(relek)
       rele = sart(rele)
       print 20,k,ertk,relek,rele
 20    format(1x,'k=',i3,' erfk=',e9.3,' ersk=',e9.3,' erts=',e9.3)
       if(k.eq.1) goto 10
       if(rele.gt.remin.and.k.lt.maxit) goto 10
c
       return
       end
c
c ------------------------------------------------------------
c
       subroutine setfld(xi,yj,etmr,icheck)
c
c      This is a subroutine to compute the true internal
c      filed and the scattered field from the true object
c      and the incident field, using c-g method.
c
c ------------------------------------------------------------
c
       real xi(1),yj(1)
       complex etmr(1),beta
       common /const/imax,jmax,nans,n,ib,jb,ic,ijmax,ijm2,
      #        nam,nam2,nsa,nsa2
       common /saddr/ks1kn,ks2kn,khrkn,kalpha,kbeta,
      #        krelek,krele,ktotn,kesn,kesdkn,kerin,kertk
       common /vaddr/krix,kxi,kyj,kes,kinc,ktot,kef,kcf,kenv,
      #        kesm,ktmr,ktf,ksk,kp1k,kp2k,kesk,khp1k,khp2k
c
       kone = 5
       kbtn = 42
c
       aim = float(imax)
       ajm = float(jmax)
       remin = 1.e-8
       maxit = 100
c
c initialize the internal field
c
       call cvmov(kinc,2,ktot,2,nam)
       call arwr print *,'C-G iterations for solving the internal field:'
       k = 0
```

```
   10    k = k + 1
         call fwcsar(imax,Jmax,nans,n,k+1,kes)
         call apwr
         call apset(ertk,kertk,1,2)
         call apwd
         ertk = sqrt(ertk)
         print 20,k,ertk
   20    format(1x,'k=',i3,2x,'erfk=',e10.4)
         if(k.eq.1) goto 10
         if(ertk.gt.remin.and.k.lt.maxit) goto 10M
c
c  Check if the internal field computed is correct
c
         if(icheck .eq.1) then
         call fwcsar(imax,Jmax,nans,n,-1,kes)
         call apwr
         call apset(erin,kerin,1,2)
         call apwd
         erin = sqrt(erin)
         print *,'|| H f - f(in) ||:',erin
         endif
c
c   compute the scatterred field
c
         call fwcsar(imax,Jmax,nans,n,0,kes)
         call apwr
c
         return
         end
c
c
c ----------------------------------------------------------------
         subroutine cprrnt(n,e)
c
c    A subroutine to print the complex arrays
c ----------------------------------------------------------------
c
         complex e(1)
         nline=n/3
         i=1
         do 10 J=1,nline
         print 20, real(e(i)),aimag(e(i)),real(e(i+1)),aimag(e(i+1)),
       #  real(e(i+2)),aimag(e(i+2))
   10    i=i+3
         i=n-nline*3
         if(i.eq.2) then
         print 30,real(e(n-1)),aimag(e(n-1)),real(e(n)),aimag(e(n))
         else
         if (i.eq.1) print 40,real(e(n)),aimag(e(n))
         end if
   20    format(3('(',e9.3,',',e10.3,') '))
   30    format(2('(',e9.3,',',e10.3,') '))
   40    format('(',e9.3,',',e10.3,') ')
         return
         end
/* ---------------------------------------------------------------- */ convol(imax,Jmax,nans,n,kv1,kv2,kcf,kcnv,ktmp,ktf,iconJ,iprod)

/* This is an apc subroutine to compute convolution using
   2-D FFT on AP. */
/* ---------------------------------------------------------------- */
```

```
int imax,Jmax,nans,n,kv1,kv2,kcf,kcnv,ktap,ktf,iconJ,iprod;
{

/* Type declaration */
        int imax1,ib,Jb,iJmax,iJm2,n2,nsa,nsa2;
        int i,i2,nam,nam2,na,itad,kone,kxi,krnsa,kv2n;
        int ih,ktih,ktJb,ktfn,iib,ktri,ktmi,ktfi,ktfni;
        int ktrpi,ktrmi,ktfri,ktfrni,kalkn,kefn,kefn1;
        int ktapn,ktapn1,ktihn,ktJbn,ndif;

/* set constants */
        imax1 = imax + 1;
        ib = 2 * imax;
        ib = ib + 1;
        Jb = 2 * Jmax;
        Jb = Jb + 1;
        iJmax = ib * Jb;
        iJm2 = 2 * iJmax;
        nam = nans * iJmax;
        nam2 = 2 * nam;
        n2 = 2 * n;
        nsa = n * n;
        nsa2 = 2 * nsa;
        kone = 5;
        krnsa = 11;
        ih = iJmax / 2;
        ktih = 2 * ih;
        ktJb = Jmax * ib;
        ktJb = 2 * ktJb;
        ktfn = n - imax;
        ktfn = ktfn * n2;
        ktfn = ktfn + ktf;

if(iprod <= 0) goto lab2;

/* multiply the object and the internal field before
   convolution */
        na = 0;
        ndif = 0;
lab1:   kv2n = kv2 + ndif;
        ktapn = ktap + ndif;
        cvmul(kv1,2,kv2n,2,ktapn,2,iJmax);
        na = na + 1;
        ndif = ndif + iJm2;
        if(na < nans) goto lab1;
lab2:   na = 0;
lab4:
        ndif = na*iJm2;
        ktapn = ktap + ndif;
        ktihn = ktih + ktapn;
        ktJbn = ktJb + ktapn;

/* copy the convolution arrays */
        vclr(kcnv,1,nsa2);
        if(iconJ == 0) goto lab11;
        cvconJ(kcf,2,kcnv,2,nsa);
        goto lab12;
lab11:  cvmov(kcf,2,kcnv,2,nsa);
lab12:
```

```
/*  Transfer the product array to be a 2-D array before
    2-D convolution. */
        vclr(ktf,1,nsa2);
        i = 0;
lab5:   i2 = i + i;
        iib = i2 * ib;
        ktpi = ktihn + iib;
        ktmi = ktihn - iib;
        ktfi = ktf + i2;
        ktfni = ktf + n2;
        ktfni = ktfni - i2;
        ktrpi = ktjbn + iib;
        ktrmi = ktjbn - iib;
        ktfri = ktfn + i2;
        ktfrni = ktfn + n2;
        ktfrni = ktfrni + i2;
        i = i + 1;
        cvmov(ktmi,2,ktfi,n2,imax1);
        cvmov(ktrmi,2,ktfri,n2,imax);
        if (i == 1) goto lab5;
        cvmov(ktpi,2,ktfni,n2,imax1);
        cvmov(ktrpi,2,ktfrni,n2,imax);
        if (i <= Jmax) goto lab5;

/*  Perform the convolution using FFT */
        cfft2d(kcnv,n,n,1);
        cfft2d(ktf,n,n,1);
        cvmul(kcnv,2,ktf,2,ktf,2,nsa);
        cvsmul(ktf,2,krnsa,ktf,2,nsa);
        cfft2d(ktf,n,n,-1);

/*  read off the one dimensional convolution array. */ i = 0;
lab6:   i2 = i + i;
        iib = i2 * ib;
        ktpi = ktihn + iib;
        ktmi = ktihn - iib;
        ktfi = ktf + i2;
        ktfni = ktf + n2;
        ktfni = ktfni - i2;
        ktrpi = ktjbn + iib;
        ktrmi = ktjbn - iib;
        ktfri = ktfn + i2;
        ktfrni = ktfn + n2;
        ktfrni = ktfrni - i2;
        i = i + 1;
        cvmov(ktfi,n2,ktmi,2,imax1);
        cvmov(ktfri,n2,ktrmi,2,imax);
        if (i == 1) goto lab6;
        cvmov(ktfni,n2,ktpi,2,imax1);
        cvmov(ktfrni,n2,ktrpi,2,imax);
        if (i < imax) goto lab6;

na = na + 1;
        if (na < nanu) goto lab4;

return;
}
```

```
/* ---------------------------------------------------------- */ eseinc(imax,Jmax,nang,n,itrun)

/*      This is an arc subroutine to generate the Gaussian
        test object and the incident field using the array
        processor. */
/* ---------------------------------------------------------- */ int imax,Jmax,nang,n,itrun;
{
/* declaration */
        int i,m,ib,Jb,iJmax,iJm2,nam2,ib1,Jb1,nsa2;
        int i2,n2,kci,keni,kpix,kpixi,kcf;
        int kmim,kmJm,kone,kxi,kyJ,kest,kfvt,kes,kes1;
        int kpsm,kcor,kcoi,kmtrh,kdela,khalf,kim;
        int kinc,kinc1,kincm,kinc1m,kesn;
        int kars,kars1,karsm,kars1m;

/* assign the AP memory */
        ib1 = 2 * imax;
        Jb1 = 2 * Jmax;
        ib = ib1 + 1;
        Jb = Jb1 + 1;
        iJmax = ib * Jb;
        iJm2 = 2 * iJmax;
        nam2 = nang * iJm2;
        n2 = 2 * n;
        nsa2 = n2 * n;
        kmim = 0;
        kmJm = 1;
        kpsm = 2;
        kcor = 3;
        kcoi = 4;
        kone = 5;
        kdela = 6;
        kmtrh = 7;
        kim = 8;
        khalf = 12;
        kesn = 48;
        kpix = 100;
        kxi = kpix + iJm2;
        kyJ = kxi + iJmax;
        kes = kyJ + iJmax;
        kes1 = kes + 1;
        kinc = kes + iJm2;
        kinc1 = kinc + 1;
        kars = kinc + nam2;
        kars1 = kars + 1;
        kcf = kars + nam2;
        kcf = kcf + nam2;

/* compute the coordinates of the points in the one-dimensional
   array */
        vramp(kmim,kone,kxi,1,ib);
        vramp(kmJm,kone,kyJ,ib,Jb);
        i = 0;
        kest = kxi;
ix:     kfvt= kest + ib;
        vfill(kest,kfvt,ib,Jb1);
        kest = kest + 1;
        i = i + 1;
```

```
            if (i < ib1) goto ix;

i = 0;
            kest = kyJ;
Jy:         kfyt = kest + 1;
            vfill(kest,kfyt,1,ib1);
            kest = kest + ib;
            i = i + 1;
            if (i < Jb) goto Jy;

/*  generate the ture dama ed: */ vmma(kxi,1,kxi,1,kyJ,1,kyJ,1,ked,2,iJmax);
            vsmul(ked,2,krsm,ked,2,iJmax);
            vexp(ked,2,kcd,2,iJmax);
            vmov(ked,2,ked1,2,iJmax);
            vsmul(ked,2,kcor,ked,2,iJmax);
            vsmul(ked1,2,kcoi,ked1,2,iJmax);
            cvmags(ked,2,kinc,2,iJmax);
            sve(kinc,2,kedn,iJmax);

/*  generate the incident field */
            vramp(kone,kone,kard,2,nans);
            vsmul(kard,2,kdela,kard,2,nans);
            vsin(kard,2,kard1,2,nans);
            vcos(kard,2,kard,2,nans);

m = 0;
            karsm = kars;
            kincm = kinc;
lab1:       karslm = karsm + 1;
            kinc1m = kincm + 1;
            vsmul(kxi,1,karsm,kincm,2,iJmax);
            vsmul(kyJ,1,karslm,kinc1m,2,iJmax);
            vadd(kincm,2,kinc1m,2,kinc1m,2,iJmax);
            vsmul(kinc1m,2,katrh,kinc1m,2,iJmax);
            vcos(kinc1m,2,kincm,2,iJmax);
            vsin(kinc1m,2,kinc1m,2,iJmax);
            m = m + 1;
            if (m > nans) goto lab2;
            karsm = karsm + 2;
            kincm = kincm + iJm2;
            goto lab1;

lab2:
            if(itrun == 0) goto lab3;
/* compute the truncation array  */
            vmaxmg(kxi,1,kyJ,1,kxi,1,iJmax);
            vlim(kxi,1,kim,khalf,kyJ,1,iJmax);
            vsadd(kyJ,1,khalf,kxi,1,iJmax);
            goto lab6;
lab3:       vfill(kone,kxi,1,iJmax);

/*  Form the Green's coef. convolution array */ lab6:       vclr(kcf,1,nsq2);
            i = 0;
lab4:       i2 = i + i;
            kci = kcf + i2;
            kcni = kcf + n2;
            kcni = kcni - i2;
            kpixi = i2 * ib;
```

```
                kpixi = kpixi + kpix;
                i = i + 1;
                cvmov(kpixi,2,kci,n2,ib);
                if (i == 1) goto lab4;
                cvmov(kci,n2,kcni,n2,ib);
                if (i < Jb) goto lab4;

i = 0;
lab5:       kci = i * n2;
            kci = kci + kcf;
            kcni = n - i;
            kcni = kcni * n2;
            kcni = kcni + kcf;
            i = i + 1;
            cvmov(kci,2,kcni,2,n);
            if (i < ib) goto lab5;

return;
}
/* ---------------------------------------------------------------- */ fwcsap(imax,Jmax,nans,n,iter,kest)

/* This is an apc subroutine to solve the forward problem using
   c-s iterations on AP. */
/* ---------------------------------------------------------------- */
int imax,Jmax,nans,n,iter,kest;
{
        int imax1,ib,Jb,iJmax,iJm2,n2,nsa,nsa2,nans3;
        int nam,nam2,na,itas,kone,Jstep,keskn,kertk,kbtn,kbtd;
        int krnsa,kpix,kt,kcf,ktf,i,i2,kci,kcni,kpixi,kr2km;
        int ih,ktih,ktJb,ktfn,iib,ktri,ktmi,ktfi,ktfni,ktotm;
        int ktrpi,ktrmi,ktfri,ktfrni,kski,krik,nclr,kerin;
        int kinc,ktot,kcnv,kes,ktmr,ktmrn,kesm,ktotn;
        int kr2k,ksk,kp1k,kr2k,khpk,kef,ndif,ktihn,ktJbn,kesk;
        int kr2kn,ks2kn,khpkn,kalpha,kbeta,krele,iconJ;
        int kxi,ktmrn1,krelek,khr1k,khr2k,khr1m,khr1m1,kskm;
        int kr2k1,kbtn1,ktmr1,kefn,kofn1;

/* Assign the AP memory */
        imax1 = imax + 1;
        ib = 2 * imax;
        ib = ib + 1;
        Jb = 2 * Jmax;
        Jb = Jb + 1;
        iJmax = ib * Jb;
        iJm2 = 2 * iJmax;
        nam = nans * iJmax;
        nam2 = 2 * nam;
        n2 = 2 * n;
        nsa = n * n;
        nsa2 = 2 * nsa;
        kone = 5;
        krnsa = 11;
        kbtn = 42;
        kbtd = 44;
        kertk = 46;
        kerin =47;
        kr2kn = 50;
        khpkn = 52;
        kalpha = 53;
        kbeta = 54;
```

```
        krelck = 55;
        ktotn = 56;
        keskn = 57;
        ks2kn = 58;
        krelc = 59;
        kpix = 100;
        kxi = kpix + iJm2;
        kes = kxi + iJmax;
        ked = kes + iJmax;
        kinc = kes + iJm2;
        ktot = kinc + nam2;
        kef = ktot + nam2;
        kcf = kef + nam2;
        kcnv = kcf + nsa2;
        kesm = kcnv + nsa2;
        ktmp = kesm + iJm2;
        ktf = ktmp + nam2;
        ksk = ktf + nsa2;
        kp1k = ksk + nam2;
        kp2k = kp1k + iJm2;
        kesk = kp2k + nam2;
        khp1k = kesk + iJm2;
        khp2k = khp1k + nam2;
        nclr = khp2k - kesm;
        nclr = nclr + nam2;
        ktmp1 = ktmp + 1;
        kbtn1 = kbtn + 1;

if(iter == -1) goto lab20;
        if(iter == 0) goto lab10;

/* compute the r2k = H f - f(in); */
        convol(imax,Jmax,nans,n,kest,ktot,kcf,kcnv,ktmp,ktf,0,1);
        cvsub(ktot,2,ktmp,2,ktmp,2,nam);
        cvsub(ktmp,2,kinc,2,ksk,2,nam);

/* compute s2k = H* r2k */
        cvconj(kest,2,kesm,2,iJmax);
        cvmov(ksk,2,ktmp,2,nam);
        convol(imax,Jmax,nans,n,kesm,ksk,kcf,kcnv,ktmp,ktf,1,-1);
        ns = 0;
        ndif = 0;
lab7:   ktmpn = ktmp + ndif;
        cvmul(kesm,2,ktmpn,2,ktmpn,2,iJmax);
        ns = ns + 1;
        ndif = ndif + iJm2;
        if(ns < nans) goto lab7;
        cvmass(ksk,2,ktmp,2,nam);
        cvmass(ksk,2,ktmp,2,nam);
        if( iter == 2) goto lab8;

/* compute <H s(k), H p(k-1)> */
        convol(imax,Jmax,nans,n,kest,ksk,kcf,kcnv,ktmp,ktf,0,1);
        cvsub(ksk,2,ktmp,2,ktmp,2,nam);
        cvconj(ktmp,2,ktmp,2,nam);
        cdotpr(ktmp,2,khp2k,2,kbtn,nam);

/* compute <H p(k-1), H p(k-1)> */
        convol(imax,Jmax,nans,n,kest,kp2k,kcf,kcnv,ktmp,ktf,0,1);
        cvsub(kp2k,2,ktmp,2,ktmp,2,nam);
        cvconj(ktmp,2,ktmp,2,nam);
        cdotpr(ktmp,2,khp2k,2,kbtd,nam);
```

```
/* compute beta */
        cvrcip(kbtd,2,kbtd,2,1);
        cvmul(kbtn,2,kbtd,2,kbtn,2,1);

/* update p2k */
        cvsmul(kp2k,2,kbtn,ktmp,2,nam);
        cvconj(kp2k,2,kp2k,2,nam);
        kp2k1= kp2k + 1;
        vsma(kp2k,2,kbtn1,ktmp1,2,ktmp1,2,nam);
        vsma(kp2k1,2,kbtn1,ktmp,2,ktmp,2,nam);
        cvmov(ktmp,2,kp2k,2,nam);
        cvsub(kp2k,2,ksk,2,kp2k,2,nam);

goto lab9;
lab8:   cvneg(ksk,2,kp2k,2,nam);
lab9:
/* compute alpha */
        convol(imax,jmax,nans,n,kest,kp2k,kcf,kcnv,ktmp,ktf,0,1);
        cvsub(kp2k,2,ktmp,2,khp2k,2,nam);
        cvmags(khp2k,2,ktmp,2,nam);
        sve(ktmp,2,khpkn,nam);
        vdiv(khpkn,1,ks2kn,1,kalpha,1,1);

/* compute new internal field and its norm */
        vsmul(kp2k,1,kalpha,ktmp,1,nam2);
        vadd(ktmp,1,ktot,1,ktot,1,nam2);

if(iter == 2) goto lab70;
/* compute relative error for forward system */
        cvmags(khp2k,2,ktmp,2,nam);
        sve(ktmp,2,kertk,nam);
        vdiv(ktotn,1,kertk,1,kertk,1,1);

lab70:
/* compute the norm of the new field */
        cvmags(ktot,2,ktmp,2,nam);
        sve(ktmp,2,ktotn,nam);
        return;

lab20: /* check to see if the computed internal field is correct */
        convol(imax,jmax,nans,n,kest,ktot,kcf,kcnv,ktmp,ktf,0,1);
        cvsub(ktot,2,ktmp,2,ktmp,2,nam);
        cvsub(ktmp,2,kinc,2,ktmp,2,nam);
        cvmags(ktmp,2,ktmp,2,nam);
        sve(ktmp,2,kerin,nam);
        return;

lab10: /* compute scattered field ef = A es */
        convol(imax,jmax,nans,n,kest,ktot,kcf,kcnv,ktmp,ktf,0,1);
        na = 0;
        ndif = 0;
lab13:  ktmpn = ktmp + ndif;
        kefn = kef + ndif;
        ktmpn1 = ktmpn + 1;
        kefn1 = kefn + 1;
        vmul(ktmpn,2,kxi,1,kefn,2,ijmax);
        vmul(ktmpn1,2,kxi,1,kefn1,2,ijmax);
        na = na + 1;
        ndif = ndif + ijm2;
        if(na < nans) goto lab13;

return;
}
```

```
/* -------------------------------------------------------- */ ivcsap(imax,Jmax,nang,n,iter,iture,ier)

/* This is an arc subroutine to solve the inverse problem
   using c-s method on AP. */
/* -------------------------------------------------------- */ int imax,Jmax,nang,n,iter,iture,ier;
{
        int imax1,ib,Jb,iJmax,iJm2,n2,nsa,nsa2,nang3;
        int nam,nam2,na,itag,kone,keskn,kertk,kbtn,kbtd;
        int krnsa,kpix,kt,kcf,ktf,i,i2,kci,kcni,krixi,kp2km;
        int ih,ktih,ktJb,ktfn,iib,ktri,ktmi,ktfi,ktfni,ktotm;
        int ktrni,ktrmi,ktfri,ktfrni,kski,kr1kn,kr1k,nclr;
        int kinc,ktot,kcnv,kes,ktar,ktarn,kesm,kesn,ktotn;
        int kr2k,ksk,kr1k,kp2k,khpk,kef,ndif,ktihn,ktJbn,kcsk;
        int ks1kn,khpkn,kalpha,kbeta,krele,iconJ;
        int kxi,ktarn1,krelek,khr1k,khp1m,khr1m1,kskm;
        int kr1k1,kp2k1,kbtn1,ktar1;
/* set constants and assign AP memories */
        imax1 = imax + 1;
        ib = 2 * imax;
        ib = ib + 1;
        Jb = 2 * Jmax;
        Jb = Jb + 1;
        iJmax = ib * Jb;
        iJm2 = 2 * iJmax;
        nam = nang * iJmax;
        nam2 = 2 * nam;
        n2 = 2 * n;
        nsa = n * n;
        nsa2 = 2 * nsa;
        kone = 5;
        krnsa = 11;
        kbtn = 42;
        kbtd = 44;
        kertk = 46;
        kesn = 48;
        kr1kn = 49;
        ks1kn = 51;
        khpkn = 52;
        kalpha = 53;
        kbeta = 54;
        krelek = 55;
        ktotn = 56;
        keskn = 57;
        krele = 59;
        kpix = 100;
        kxi = kpix + iJm2;
        kes = kxi + iJmax;
        kes = kes + iJmax;
        kinc = kes + iJm2;
        ktot = kinc + nam2;
        kef = ktot + nam2;
        kcf = kef + nam2;
        kcnv = kcf + nsa2;
        kesm = kcnv + nsa2;
        ktar = kesm + iJm2;
        ktf = ktar + nam2;
        ksk = ktf + nsa2;
        kr1k = ksk + nam2;
```

```
             kp2k = kp1k + iJm2;
             kesk = kp2k + nsm2;
             khr1k = kesk + iJm2;
             nclr = khr1k - kesm;
             nclr = nclr + nsm2;

if (iter > 1) goto lab3;
             if(itype = 1) goto lab3;

/* initialization */
/* set initial internal field */
             cvmov(kinc,2,ktot,2,nsm);

/* clear the memory */
             vclr(kr1kn,1,10);
             vclr(kesm,1,nclr);

/* set initial residual r1k = - ef */
             cvneg(kef,2,ksk,2,nsm);

goto lab20;

lab3:    /* compute new residual r1k = A esk - ef */
             convol(imax,Jmax,nans,n,kesk,ktot,kef,kcnv,ktmp,ktf,0,1);
             na = 0;
             ndif = 0;
lab63:   ktmpn = ktmp + ndif;
             ktmpn1 = ktmpn + 1;
             vmul(ktmpn,2,kxi,1,ktmpn,2,iJmax);
             vmul(ktmpn1,2,kxi,1,ktmpn1,2,iJmax);
             na = na + 1;
             ndif = ndif + iJm2;
             if(na < nans) goto lab63;
             vsub(ktmp,2,kef,2,ksk,2,nsm);
             cvmass(ksk,2,ktmp,2,nsm);
             sve(ktmp,2,kr1kn,nsm);

lab20:   /* compute sik = A* r1k */
             convol(imax,Jmax,nans,n,kesk,ktmp,kef,kcnv,ksk,ktf,1,0);
             cvconj(ktot,2,ktmp,2,nsm);
             cvmul(ksk,2,ktmp,2,ktmp,2,nsm);

i = 0;
lab21:   ktmpn = ktmp + i;
             kski = ksk + i;
             sve(ktmpn,iJm2,kski,nans);
             i = i + 1;
             if(i < iJm2) goto lab21;
             cvmass(ksk,2,ktmp,2,iJmax);
             sve(ktmp,2,ks1kn,iJmax);

if(itype == 1) goto lab23;

/* compute <A(k+1) d(k), A(k) p(k-1)> */
             convol(imax,Jmax,nans,n,ksk,ktot,kef,kcnv,ktmp,ktf,0,1);
             cvconj(ktmp,2,ktmp,2,nsm);
             cdotpr(ktmp,2,khr1k,2,kbtn,nsm);

/* compute <A(k+1) p(k-1), A(k) p(k-1)> */
             convol(imax,Jmax,nans,n,kr1k,ktot,kef,kcnv,ktmp,ktf,0,1);
             cvconj(ktmp,2,ktmp,2,nsm);
             cdotpr(ktmp,2,khr1k,2,kbtd,nsm);
```

```
/* compute beta */
        cvrcip(kbtd,2,kbtd,2,1);
        cvmul(kbtn,2,kbtd,2,kbtn,2,1);
        cvconj(kbtn,2,kbtn,2,1);

/* update p1k */
        cvsmul(kp1k,2,kbtn,ktmp,2,ijmax);
        cvconj(kp1k,2,kp1k,2,ijmax);
        kp1k1= kp1k + 1;
        vsma(kp1k,2,kbtn1,ktmp1,2,ktmp1,2,ijmax);
        vsma(kp1k1,2,kbtn1,ktmp,2,ktmp,2,ijmax);
        cvmov(ktmp,2,kp1k,2,ijmax);
        cvsub(kp1k,2,ksk,2,kp1k,2,ijmax);
        goto lab24;
lab23:  cvneg(ksk,2,kp1k,2,ijmax);
lab24:
/* compute alpha */
        convol(imax,jmax,nans,n,kp1k,ktot,kcf,kcnv,khp1k,ktf,0,1);
        na = 0;
        ndif = 0;
lab26:  khp1m = khp1k + ndif;
        khp1m1 = khp1m + 1;
        vmul(khp1m,2,kxi,1,khp1m,2,ijmax);
        vmul(khp1m1,2,kxi,1,khp1m1,2,ijmax);
        na = na + 1;
        ndif = ndif + ijm2;
        if (na < nans) goto lab26;

cvmags(khp1k,2,ktmp,2,nam);
        sve(ktmp,2,khpkn,nam);
        vdiv(khpkn,1,ks1kn,1,kalpha,1,1);

/* compute new sams */
        vsmul(kp1k,1,kalpha,ksk,1,ijm2);
        vadd(ksk,1,kesk,1,kesk,1,ijm2);

if(ier != 1) goto lab30;

/* compute the relative error */
        cvmags(ksk,2,ktmp,2,ijmax);
        sve(ktmp,2,krelek,ijmax);
        vdiv(keskn,1,krelek,1,krelek,1,1);
        cvsub(kesk,2,kes,2,ktmp,2,ijmax);
        cvmags(ktmp,2,ktmp,2,ijmax);
        sve(ktmp,2,krele,ijmax);
        vdiv(kesn,1,krelo,1,krele,1,1);

lab30:
/* compute the norm of the sams */
        cvmags(kesk,2,ktmp,2,ijmax);
        sve(ktmp,2,keskn,ijmax);

return;
}
```

What is claimed and desired to be secured by U.S. Letters Patent is as follows:

1. A method of producing an image of an object from acoustic energy that has been transmitted through and scattered by the object, said image comprising a high and acoustic absorption at all points within the object, and said method comprising the steps of:

electronically transmitting an electric signal at multiple frequencies and transducing said electric signal at each said frequency into acoustic energy propagated toward said object from a plurality of transducer transmitter positions;

electronically processing said electrical signal to determine from said transmitter positions an incident field corresponding to said propagated acoustic energy, said incident field being stored in the memory of a central processing unit (CPU) in the form of digitized electric signals;

detecting at a plurality of transducer receiver positions said acoustic energy transmitted through and scattered by said object;

electronically processing said detected acoustic energy so as to transform said detected energy into a plurality of digitized electric signals stored in said memory of said CFU and corresponding to a scattered field detected at said transducer receiver positions;

said CPU preparing an initial estimate of the scattering potential for said object and an initial estimate of the internal field of said object at each pixel of a display screen on which said acoustic image is to be displayed and storing each said estimate in said memory;

said CPU determining at each said frequency and storing in said memory a scattered field derived at said frequency from said initial estimates of the scattering potential and internal field, and thereafter comparing at said frequency said scattered field detected at said receiver positions to said scattered field determined by said CPU;

said CPU determining at each said frequency and storing in said memory a new estimate of said internal field at each said pixel derived from said incident field, the last estimate of the internal field at each said pixel, and the last estimate of said scattering potential at each said pixel, said new estimate of the internal field at said frequency comprising all orders of scattering;

said CPU determining and storing in said memory a new estimate of said scattering potential derived from said new estimate of said internal field and said scattered field detected at said receiver positions;

said CPU continuing to update the estimate for said internal field and scattering potential until said scattered field determined by said CPU approximates said scattered field detected at said receiver positions within a selected range of tolerance; and said CPU thereafter using the determined scattering potential to reconstruct and store said image in said CPU memory.

2. A method as defined in claim 1 wherein said step of electronically transmitting said electric signal at multiple frequencies comprises the steps of:

positioning a transducer array adjacent said object, said array comprising a plurality of acoustic transmitters and acoustic receivers;

sending said electric signal at a first frequency to each said transmitter so that each said transmitter will in turn propagate acoustic energy at said first frequency; and thereafter changing the frequency of said signal and sending said electrical signal at said changed frequency to each said transmitter so as to sequentially propagate acoustic energy from said said transmitter at said changed frequency.

3. A method as defined in claim 1 wherein said step of electronically transmitting an electric signal at multiple frequencies comprises the steps of:

positioning a transducer array adjacent to said object, said array comprising a plurality of acoustic transmitters and a plurality of acoustic receivers;

generating said electric signal in the form of a waveform which is characterized by a plurality of different frequencies; and sending said generated waveform in turn to each said transmitter so as to propagate acoustic energy at said multiple frequencies from each said transmitter.

4. A method as defined in claims 2 or 3 wherein said transducer array is configured to encircle said object.

5. A method as defined in claim 1 wherein said step of detecting at a plurality of transducer-receiver positions said acoustic energy transmitted through and scattered by said object comprises the steps of:

positioning a transducer array adjacent said object, said array comprising a plurality of transmitters and a plurality of receivers; and after acoustic energy is transmitted from one of said transmitters, sequencing each said receiver so as to detect said scattered acoustic energy at each said receiver in turn.

6. A method as defined in claim 5 wherein said step of electronically processing said detected acoustic energy comprises the steps of:

transducing the acoustic energy detected by each said receiver transducer into a corresponding electric signal; amplifying said corresponding electric signal; and thereafter processing each said amplified signal so as to generate two signals which correspond to mathematical real and imaginary representations of each said amplified signal.

7. A method as defined in claim 6 wherein the step of processing said amplified signal from each said receiver transducer so as to generate said signals corresponding to said mathematical real and imaginary representations of said amplified signal comprises the steps of:

inputting the amplified signal detected at said receiver transducer to first and second multiplier circuits and multiplying the amplified signal input to said first multiplier circuit by the electric signal sent to said transmitter transducers;

shifting the phase of said electric signal sent to said transmitter transducers by 90° and thereafter multiplying the amplified signal input to said second multiplier circuit by said signal that is shifted by 90°; and filtering the output of each said multiplier circuit with a low-pass filter circuit and thereafter integrating and digitizing the output of each said low-pass filter circuit.

8. A method as defined in claim 6 wherein said step of processing said amplified signals from each said receiver transducer so as to generate said signals corresponding to said mathematical real and imaginary representations of each said amplified signal comprises the steps of:

inputting each said amplified signal to a high speed analog-to-digital converter so as to digitize each said amplified signal; and inputting each said digitized signal from said high speed analog-to-digital converter into a parallel processor programmed to take the complex fast Fourier transform of each said digitized signal.

9. A method as defined in claim 5 wherein said transducer array is configured to encircle said object.

10. A method as defined in claim 1 wherein said initial estimate of said scattering potential is zero.

11. A method as defined in claim 1 wherein said initial estimate of said scattering potential is an average value determined by an estimated average of density, acoustic speed and acoustic absorption of said object.

12. A method as defined in claim 1 wherein said incident field is used as said initial estimate of the internal field of said object at each said pixel.

13. A method as defined in claim 1 wherein said estimate of the internal field of each said object at each said pixel is determined by said CPU from said initial estimate of said scattering potential.

14. A method as defined in claim 1 wherein said step of determining said new estimate of said scattering potential comprises the steps of:

backprojecting said scattered field detected at said transducer-receiver positions to obtain a blurred image of said scattering potential of said object; and deblurring said blurred image of said scattering potential to obtain said new estimate of the scattering potential.

15. A method as defined in claim 14 wherein said incident field, said scattered field detected at said transducer-receiver positions, each said initial and new estimate of said internal field and each said initial and new estimate of said scattering potential are obtained separately by said CPU at each said frequency.

16. A method as defined in claim 15 wherein said scattering potential is formulated using a plurality of frequency-independent components represented as a vector $\Gamma$ multiplied by a frequency-dependent matrix M, and wherein a least-squares method is applied by said CPU to the product $M\Gamma$ so as to derive therefrom a scattering potential comprised of frequency-dependent terms whose sum represents a best fit to said deblurred image of said scattering potential.

17. A method as defined in claim 16 wherein said least-squares method is applied by said CPU using a conjugate gradient method.

18. A method as defined in claim 1 wherein said incident field, said scattered field detected at said transducer-receiver positions, and each said initial and new estimate of said internal field are obtained separately by said CPU at each said frequency.

19. A method as defined in claim 18 wherein said new estimate of said internal field and said new estimate of said scattering potential are obtained by said CPU according to a conjugate gradient method.

20. A method as defined in claim 19 wherein said scattering potential obtained by said CPU comprises a plurality of frequency-independent components represented as a vector $\Gamma$.

21. A method as defined in claim 19 wherein said conjugate gradient method is used by said CPU to determine said new estimates of said internal field and said scattering potential by computing a descent direction wherein each variable from a set of variables taken from a first vector equation defining said internal field and a second vector equation defining said scattered field detected at said receiver positions is allowed to vary simultaneously.

22. A method of reconstructing an acoustic image of an object using a central processing unit (CPU) programmed to process data derived from acoustic energy that has been transmitted at multiple frequencies and scattered by said object, said method comprising the steps of:

propagating multiple frequency acoustic energy waves toward said object from a plurality of transmitters positions;

electronically storing a plurality of digitized electronic signals derived by said CPU from said propagated acoustic energy and said transmitter positions, said digitized electronic signals representing an incident field obtained at each said frequency detecting at a plurality of receivers multiple frequency acoustic energy waves scattered by said object;

electronically storing a plurality of digitized electronic signals representing all orders of a scattered field obtained at each said frequency and derived by said CPU from the scattered acoustic energy waves detected at said receivers;

said CPU determining (a) an estimate of an internal field at each said frequency and at each scattering point within said object, and (b) an estimate of a scattering potential characterized by density, acoustic speed and acoustic absorption at each said frequency and at each scattering point within said object, and said CPU electronically storing a plurality of digitized electronic signals representing said estimates of said internal field and said scattering potential;

said CPU determining from said estimated internal field and scattering potential a predicted scattered field at all orders of scattering and at each said frequency, and said CPU comparing said predicted scattered field to said scattered field derived from the scattered acoustic energy waves detected at said receivers;

said CPU updating said estimates of said internal field and said scattering potential until said comparison results in a predicted scattered field which approximates said scattered field derived from the scattered acoustic energy waves detected at said receivers within a selected range of tolerance; and said CPU thereafter reconstructing from said estimated scattering potential an acoustic image of said object, and outputting a visually perceptible display of said image.

23. A method as defined in claim 22 wherein said step of said CPU updating said estimate of said internal field comprises the step of said CPU deriving said updated estimate of said internal field from said incident field and from said estimate of said scattering potential.

24. A method as defined in claim 23 wherein said step of said CPU updating said estimate of said scattering potential comprises the step of said CPU deriving said updated estimate of said scattering potential from said updated estimate of said internal field and from said scattered field derived from the scattered acoustic energy waves detected at said receivers.

25. A method as defined in claim 24 wherein said step of said CPU updating said estimate of said scattering potential further comprises the steps of:
  backprojecting said scattered field derived from the scattered acoustic energy waves detected at said receivers to obtain a blurred image of said updated scattering potential; and
  deblurring said blurred image.

26. A method as defined in claim 25 further comprising the steps of:
  said CPU formulating a frequency-independent vector $\Gamma$ comprised of a plurality of frequency-independent components;
  said CPU setting said updated estimate of said scattering potential equal to the product of said vector and a frequency-dependent matrix M; and
  said CPU applying a least-squares method to said product $M\Gamma$ so as to derive therefrom a product comprising a plurality of frequency-dependent terms whose sum represents a best fit to said deblurred image.

27. A method as defined in claim 23 wherein said updated estimate of said internal field is obtained by said CPU according to a conjugate gradient method.

28. A method as defined in claim 27 further comprising the steps of:
  said CPU formulating a frequency-independent vector $\Gamma$ comprised of a plurality of frequency-independent components;
  said CPU applying a conjugate gradient method to obtain an updated estimate of said vector from said updated internal field and from said scattered field derived from the scattered acoustic energy waves detected at said receivers; and
  said CPU determining said updated estimate of said scattering potential from the product of said updated vector and a frequency-dependent matrix M.

29. A method as defined in claim 28 wherein said conjugate gradient method is used by said CPU to determine said updated estimates of said internal field and said vector by computing a descent direction wherein each variable from a set of variables defined by (a) a first set of equations defining said internal field and (b) a second set of equations defining said scattered field detected at said receivers is allowed to simultaneously vary.

30. A method as defined in claim 22 wherein said step of propagating said multiple frequency acoustic energy waves comprises the step of electronically transmitting an electric signal at multiple frequencies and transducing said electric signal at each set frequency into said acoustic energy waves.

31. A method as defined in claim 30 wherein said step of electronically transmitting said electric signal at multiple frequencies comprises the steps of:
  positioning a transducer array adjacent said object, said array comprising a plurality of acoustic transmitters;
  sending said electric signal at a first frequency to each said transmitter so that each said transmitter will in turn propagate acoustic energy at said first frequency; and
  thereafter changing the frequency of said signal and sending said electrical signal at said changed frequency to each said transmitter so as to sequentially propagate acoustic energy from each said transmitter at said changed frequency.

32. A method as defined in claim 30 wherein said step of electronically transmitting an electric signal at multiple frequencies comprises the steps of:
  positioning a transducer array adjacent to said object, said array comprising a plurality of acoustic transmitters;
  generating said electric signal in the form of a waveform which is characterized by a plurality of different frequencies; and
  sending said generated waveform in turn to each said transmitter so as to propagate acoustic energy at said multiple frequencies from each said transmitter.

33. A method as defined in claims 30 or 31 wherein said transducer array is configured to encircle said object.

34. A method as defined in claim 22 wherein said step of detecting at said plurality of receivers said multiple frequency acoustic energy waves scattered by said object comprises the steps of:
  positioning a transducer array adjacent said object, said array comprising a plurality of acoustic receivers;
  sequencing each said receiver so as to detect said scattered acoustic energy waves at each said receiver in turn; and
  electronically processing said detected acoustic energy waves so as to transform said detected acoustic energy waves into a plurality of digitized electric signals.

35. A method as defined in claim 34 wherein said step of electronically processing said detected acoustic energy waves comprises the steps of:
  transducing said acoustic energy waves detected by each said receiver into a corresponding electrical signal;
  amplifying said corresponding electric signal; and
  thereafter processing each said amplified signal so as to generate two signals which correspond to mathematical real and imaginary representations of each said amplified signal.

36. A method as defined in claim 35 wherein said step of processing each said amplified signal so as to generate said signals corresponding to said mathematical real and imaginary representations of said amplified signal comprises the steps of:
  inputting each said amplified signal to first and second multiplier circuits and multiplying the amplified signal input to said first multiplier circuit by the electric signal sent to said transmitter transducers;
  shifting the phase of said electric signal sent to said transmitter transducers by 90° and thereafter multiplying the amplified signal input to said second multiplier circuit by said signal that is shifted by 90°; and
  filtering the output of each said multiplier circuit with a low-pass filter circuit and thereafter integrating and digitizing the output of each said low-pass filter circuit.

37. A method as defined in claim 35 wherein said step of processing each said amplified signals so as to generate said signals corresponding to said mathematical real and imaginary representations of each said amplified signal comprises the steps of:

inputting each said amplified signal to a high speed analog-to-digital converter so as to digitize each said amplified signal; and inputting each said digitized signal from said high speed analog-to-digital converter into a parallel processor programmed to take the complex fast Fourier transform of each said digitized signal.

38. A method as defined in claim 34 wherein said transducer array is configured to encircle said object.

* * * * *

UNITED STATES PATENT AND TRADEMARK OFFICE
CERTIFICATE OF CORRECTION

PATENT NO. : 4,662,222

DATED : May 5, 1987

INVENTOR(S) : STEVEN A. JOHNSON

It is certified that error appears in the above-identified patent and that said Letters Patent is hereby corrected as shown below:

Column 1, line 8, after the heading "BACKGROUND" insert the following paragraph:

--This invention was made with government support under Grant numbers R01 HL 34995 and R01 CA 29728 awarded by the Department of Health & Human Services. The government has certain rights in the invention.--

Signed and Sealed this

Sixth Day of April, 1993

Attest:

STEPHEN G. KUNIN

*Attesting Officer*     Acting Commissioner of Patents and Trademarks